US011125743B2

(12) United States Patent
Green et al.

(10) Patent No.: US 11,125,743 B2
(45) Date of Patent: Sep. 21, 2021

(54) DETECTION OF NOROVIRUS USING NOROVIRUS-SPECIFIC TOEHOLD SWITCHES

(71) Applicant: Arizona Board of Regents on behalf of Arizona State University, Scottsdale, AZ (US)

(72) Inventors: Alexander Green, Scottsdale, AZ (US); Duo Ma, Tempe, AZ (US); Luhui Shen, Tempe, AZ (US); Chris Diehnelt, Chandler, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

(21) Appl. No.: 16/279,045

(22) Filed: Feb. 19, 2019

(65) Prior Publication Data
US 2019/0285620 A1  Sep. 19, 2019

Related U.S. Application Data

(60) Provisional application No. 62/632,792, filed on Feb. 20, 2018.

(51) Int. Cl.
| G01N 33/543 | (2006.01) |
| G01N 33/53 | (2006.01) |
| G01N 33/569 | (2006.01) |
| C07K 19/00 | (2006.01) |

(52) U.S. Cl.
CPC ....... *G01N 33/54306* (2013.01); *C07K 19/00* (2013.01); *G01N 33/5308* (2013.01); *G01N 33/5434* (2013.01); *G01N 33/569* (2013.01); *C07K 2317/569* (2013.01); *C07K 2317/60* (2013.01); *C07K 2318/00* (2013.01)

(58) Field of Classification Search
None
See application file for complete search history.

(56) References Cited

U.S. PATENT DOCUMENTS

| 2016/0153991 | A1* | 6/2016 | Gupta | G01N 33/56983 506/9 |
| 2017/0088828 | A1* | 3/2017 | Quake | C12N 9/22 |
| 2017/0349939 | A1* | 12/2017 | Metzker | C12Q 2531/125 |
| 2019/0071737 | A1 | 3/2019 | Green | |
| 2019/0185856 | A1 | 6/2019 | Green | |
| 2019/0218624 | A1 | 7/2019 | Green | |
| 2019/0256898 | A1 | 8/2019 | Green | |
| 2019/0276901 | A1 | 9/2019 | Green | |
| 2019/0382746 | A1 | 12/2019 | Green | |

FOREIGN PATENT DOCUMENTS

| WO | 2017147585 A1 | 8/2017 |
| WO | 2017205668 A1 | 11/2017 |
| WO | 2018026762 A1 | 2/2018 |
| WO | 2018026765 A1 | 2/2018 |
| WO | 2018027177 A1 | 2/2018 |
| WO | 2018075502 A1 | 4/2018 |
| WO | 2018093898 A1 | 5/2018 |
| WO | 2018112350 A1 | 6/2018 |
| WO | 2018187687 A1 | 10/2018 |

OTHER PUBLICATIONS

Gupta et al., Anal. Chem., 2017, 89(13):7174-7181. (Year: 2017).*
Ahmed, S.M., et al, "Global prevalence of norovirus in cases of gastroenteritis: a systematic review and meta-analysis," Lancet Infect Dis 14, 725-730 (2014).
Ambert-Balay K. et al, "Evaluation of 4 immunochromatographic tests for rapid detection of norovirus in faecal samples," Journal of clinical virology : the official publication of the Pan American Society for Clinical Virology 56, 194-198 (2013).
Bartsch, S.M., et al, "Global Economic Burden of Norovirus Gastroenteritis," PLoS ONE 11, e0151219 (2016).
De Graaf, M., et al, "Human norovirus transmission and evolution in a changing world," Nat Rev Microbiol 14, 421-433 (2016).
Scallan, E., et al, "Foodborne Illness Acquired in the United States—Major Pathogens," Emerging Infectious Disease journal 17, 7 (2011).
Fukuda, S. et al, "Rapid and Sensitive Detection of Norovirus Genomes in Oysters by a Two-Step Isothermal Amplification Assay System Combining Nucleic Acid Sequence-Based Amplification and Reverse Transcription-Loop-Mediated Isothermal Amplification Assays," Applied and Environmental Microbiology 74, 3912-3914 (2008).
Fukuda, S. et al, "Rapid Detection of Norovirus from Fecal Specimens by Real-Time Reverse Transcription-Loop-Mediated Isothermal Amplification Assay," Journal of Clinical Microbiology 44, 1376-1381 (2006).
Furuya, D., et al. "Age, viral copy number, and immunosuppressive therapy affect the duration of norovirus RNA excretion in inpatients diagnosed with norovirus infection." Jpn J Infect Dis 64.2 (2011): 104-8.
Gibson, D. G., et al. "Enzymatic assembly of DNA molecules up to several hundred kilobases." Nature methods6.5 (2009): 343.
Green, A. A. "Construction and in vivo testing of prokaryotic riboregulators." RNA Nanostructures. Humana Press, New York, NY, 2017. 285-302.
Green, A. A., et al. "Complex cellular logic computation using ribocomputing devices." Nature 548.7665 (2017): 117.
Green, A. A., et al. "Toehold switches: de-novo-designed regulators of gene expression." Cell 159.4 (2014): 925-939.

(Continued)

*Primary Examiner* — Nicole Kinsey White
(74) *Attorney, Agent, or Firm* — Quarles & Brady LLP

(57) ABSTRACT

Provided herein are methods and systems for low-cost, low-equipment detection of pathogens in biological sample. In particular, provided herein is a low-cost method for detecting norovirus that provides reliable, visible test with femtomolar, attomolar, and zeptomolar detection limits and that uses materials suitable for deployment of the methods in the field.

16 Claims, 27 Drawing Sheets

Specification includes a Sequence Listing.

(56) References Cited

OTHER PUBLICATIONS

Greene, S.R. et al, "Evaluation of the NucliSens Basic Kit assay for detection of Norwalk virus RNA in stool specimens," Journal of virological methods 108, 123-131 (2003).

Guatelli, J. C., et al, "Isothermal, in vitro amplification of nucleic acids by a multienzyme reaction modeled after retroviral replication," Proc Natl Acad Sci U S A 87, 7797 (1990).

Gupta, N., et al, "Cross-Reactive Synbody Affinity Ligands for Capturing Diverse Noroviruses," Anal Chem 89, 7174-7181 (2017).

Gupta, N., et al, "Whole-Virus Screening to Develop Synbodies for the Influenza Virus," Bioconjugate Chemistry 27, 2505-2512 (2016).

Hall, A.J. et al, "Norovirus Disease in the United States," Emerging Infectious Disease journal 19, 1198 (2013).

Henningsson, A. J., et al. "Rapid diagnosis of acute norovirus-associated gastroenteritis: evaluation of the Xpert Norovirus assay and its implementation as a 24/7 service in three hospitals in Jönköping County, Sweden." European Journal of Clinical Microbiology & Infectious Diseases 3610 (2017): 1867-1871.

Iturriza-Gomara, M. et al, "Evaluation of the Loopamp (loop-mediated isothermal amplification) kit for detecting Norovirus RNA in faecal samples," Journal of clinical virology : the official publication of the Pan American Society for Clinical Virology 42, 389-393 (2008).

Jeon, S.B. et al, "Development of one-step reverse transcription loop-mediated isothermal amplification for norovirus detection in oysters," Food Control 73, 1002-1009 (2017).

Khamrin, P. et al, "Evaluation of immunochromatography tests for detection of novel GII.17 norovirus in stool samples," Euro surveillance : bulletin Europeen sur les maladies transmissibles= European communicable disease bulletin 20 (2015).

Kroneman, A., et al. "Proposal for a unified norovirus nomenclature and genotyping." Archives of virology 158.10 (2013): 2059-2068.

Lamhoujeb, S. et al, "Real-time molecular beacon NASBA for rapid and sensitive detection of norovirus GII in clinical samples," Canadian journal of microbiology 55, 1375-1380 (2009).

Lopman, B. A., et al. "The vast and varied global burden of norovirus: prospects for prevention and control." PLoS medicine 13.4 (2016): e1001999.

Moore M.D., et al, "Development of a Recombinase Polymerase Amplification Assay for Detection of Epidemic Human Noroviruses," Scientific Reports 7, 40244 (2017).

Moore, C., et al. "Evaluation of a broadly reactive nucleic acid sequence based amplification assay for the detection of noroviruses in faecal material." Journal of Clinical Virology 29.4 (2004): 290-296.

Musso, D., et al. "Molecular detection of Zika virus in blood and RNA load determination during the French Polynesian outbreak." Journal of medical virology 89.9 (2017): 1505-1510.

Ng, AHC, et al. "Digital microfluidic magnetic separation for particle-based immunoassays." Analytical chemistry 84.20 (2012):8805-8812.

Notomi, T. et al, "Loop-mediated isothermal amplification of DNA," Nucleic Acids Research 28, e63-e63 (2000).

Pardee, K. et al, "Paper-based synthetic gene networks," Cell 159, 940-954 (2014).

Pardee, K. et al, "Rapid, Low-Cost Detection of Zika Virus Using Programmable Biomolecular Components," Cell 165, 1255-1266 (2016).

Patterson, S.S., et al, "A nucleic acid sequence-based amplification assay for real-time detection of norovirus genogroup II," Journal of applied microbiology 101, 956-963 (2006).

Payne, D. C., et al. "Norovirus and medically attended gastroenteritis in US children." New England journal of medicine 368.12 (2013): 1121-1130.

Piepenburg, O., et al, "DNA Detection Using Recombination Proteins," PLOS Biology 4, e204 (2006).

Puri, L. et al, "Xpert MTB/RIF for tuberculosis testing: access and price in highly privatised health markets," The Lancet Global Health 4, e94-e95 (2016).

Rabinowitz, J. A., et al. "Non-natural amino acid peptide microarrays to discover Ebola virus glycoprotein ligands." Chemical Communications 54.12 (2018): 1417-1420.

Rutjes, S.A., et al, "Real-time detection of noroviruses in surface water by use of a broadly reactive nucleic acid sequence-based amplification assay," Appl Environ Microbiol 72, 5349-5358 (2006).

Shah, M. et al, "Comparison of laboratory costs of rapid molecular tests and conventional diagnostics for detection of tuberculosis and drug-resistant tuberculosis in South Africa," BMC Infectious Diseases 13, 352 (2013).

Siebenga, J.J. et al, "Norovirus Illness Is a Global Problem: Emergence and Spread of Norovirus GII.4 Variants, 2001-2007," The Journal of Infectious Diseases 200, 802-812 (2009).

Vinjé J., "Advances in Laboratory Methods for Detection and Typing of Norovirus," Journal of Clinical Microbiology 53, 373-381 (2015).

Vyas, K, et al, "Comparison of five commercially available immunochromatographic tests for the detection of norovirus in faecal specimens," The Journal of hospital infection 91, 176-178 (2015).

Naggoner, J.J. et al, "Viremia and Clinical Presentation in Nicaraguan Patients Infected With Zika Virus, Chikungunya Virus, and Dengue Virus," Clinical Infectious Diseases 63, 1584-1590 (2016).

Yaren, O., et al, "A norovirus detection architecture based on isothermal amplification and expanded genetic systems," Journal of virological methods 237, 64-71 (2016).

Yoda, T., et al, "Application of a modified loop-mediated isothermal amplification kit for detecting Norovirus genogroups I and II," Journal of medical virology 81, 2072-2078 (2009).

Zadeh, J.N. et al, "Nucleic acid sequence design via efficient ensemble defect optimization," Journal of computational chemistry 32, 439-452 (2011).

Zadeh, J.N. et al, "NUPACK: Analysis and design of nucleic acid systems," Journal of computational chemistry 32, 170-173 (2011).

* cited by examiner

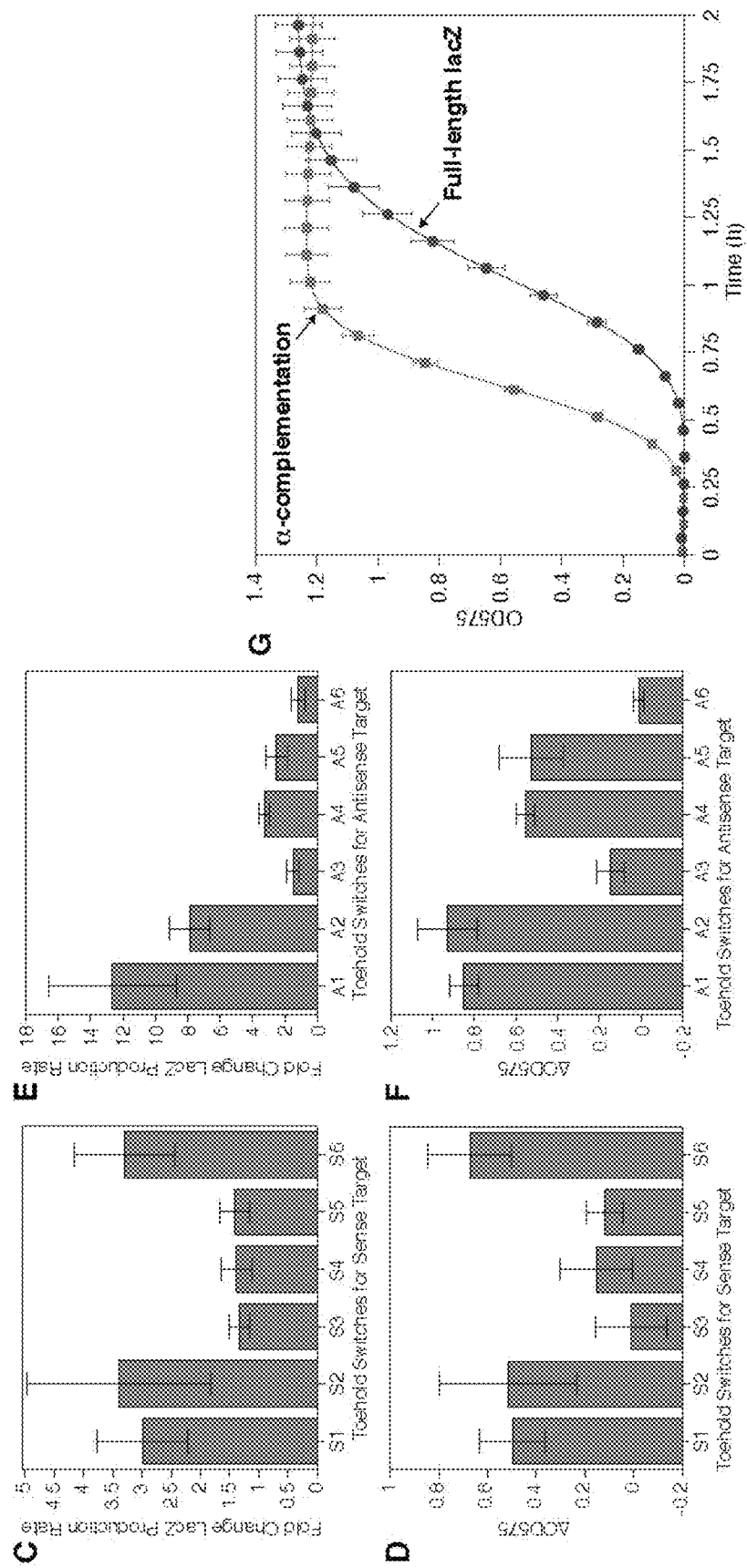
FIGS. 2A-2G, CONTINUED

FIGS. 7A-7L, CONTINUED
Devices for Sense Target
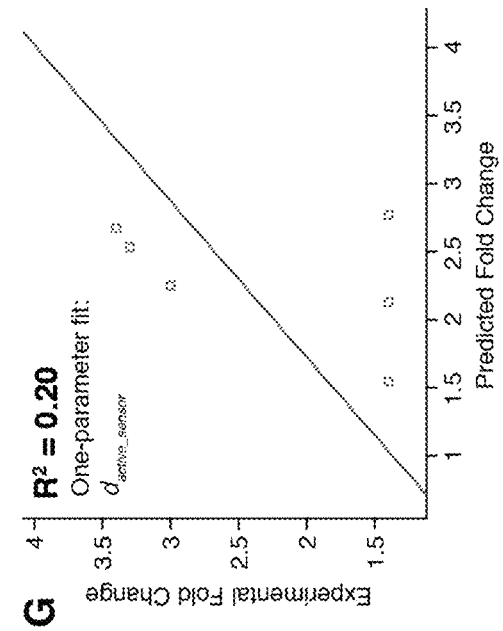
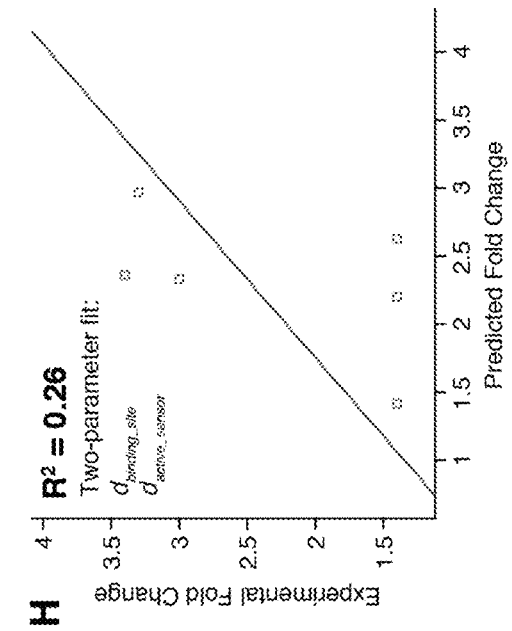
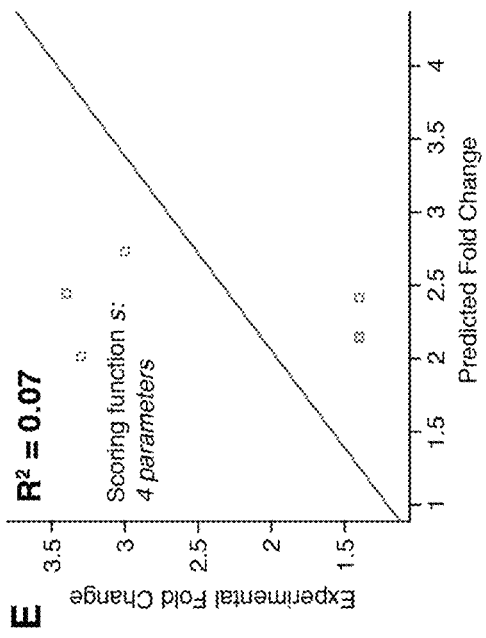
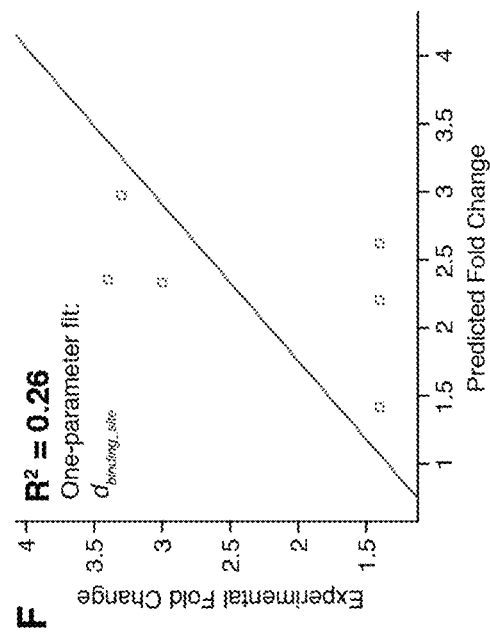

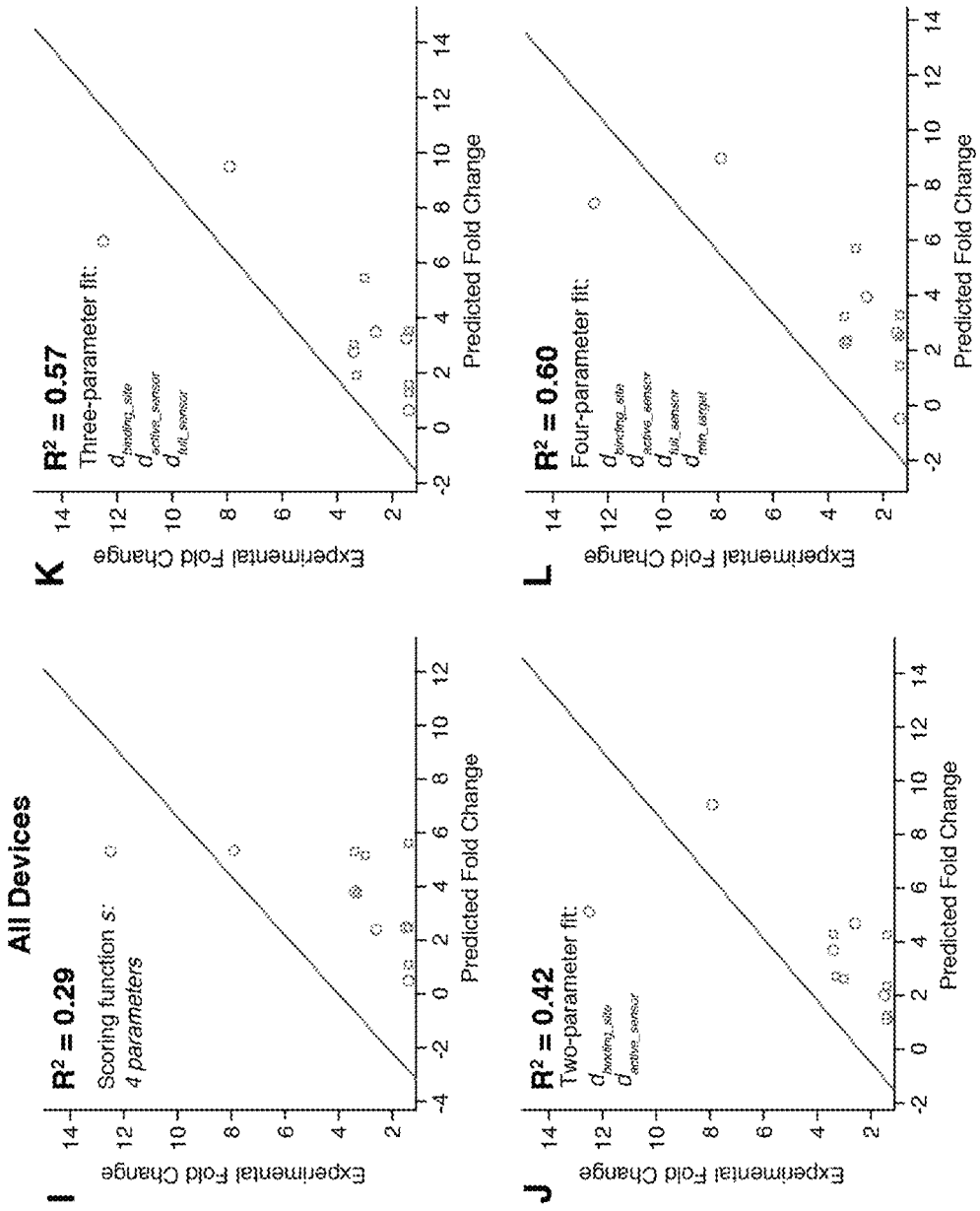
FIGS. 7A-7L, CONTINUED

DETECTION OF NOROVIRUS USING NOROVIRUS-SPECIFIC TOEHOLD SWITCHES

CROSS-REFERENCE TO RELATED APPLICATIONS

This application claims the benefit of U.S. Provisional Application No. 62/632,792, filed Feb. 20, 2018, which is incorporated in its entirety herein by reference.

STATEMENT REGARDING FEDERALLY SPONSORED RESEARCH

This invention was made with government support under GM126892 awarded by the National Institutes of Health and 2011-68003-30395 awarded by USDA/NIFA. The government has certain rights in the invention.

BACKGROUND

Noroviruses are a primary cause of gastroenteritis and foodborne illness with cases that affect millions of people worldwide each year. At present, the most commonly used methods to detect norovirus are immunochromatographic lateral flow assays and PCR-based tests. Immunochromatographic lateral flow assays employ antibodies that recognize viral surface proteins and can be advantageous since they do not require specialized equipment and provide test results in 15 minutes. However, these tests provide limited sensitivity and their results can be strongly genotype dependent. Real-time quantitative reverse transcriptase PCR (qRT-PCR) is currently the gold standard for detection of norovirus. qRT-PCR assays can be targeted to conserved regions of the norovirus genome and they provide high specificity and sensitivity. These assays, however, require expensive thermal cycling equipment and are typically run in centralized laboratories. Shipment of samples can delay test results and specialized laboratory equipment is often not available in developing countries or in remote settings, such as ships at sea, where outbreaks frequently occur. Highly automated commercial instruments such as the Cepheid GeneXpert have been developed for decentralized use. However, these instruments are expensive. Even with negotiated prices for low- and middle-income countries, the GeneXpert instrument, for instance, costs $17,000 and has cartridges available at a concessional price of $9.98. These factors lead to an overall per test cost of $14.93 once labor, consumable, and other costs are included. In the absence of discounts, GeneXpert costs rise substantially to $30.26-$155.44 per test depending on the country. Accordingly, there remains a need in the art for inexpensive tests for pathogens such as norovirus that do not require sophisticated laboratory equipment and that provide timely results for disease containment.

SUMMARY

This disclosure is related to methods of detecting pathogen infection using paper-based cell-free transcription-translation reactions. More particularly, the embodiments provided herein relate to methods in which a sample is enriched for the pathogen using synbodies and isothermal amplification followed by detection of pathogen nucleic acids using sequence-specific toehold switches and cell-free transcription and translation reactions.

In a first aspect, provided herein is a method of detecting a target pathogen nucleic acid in a sample. The method can comprise or consist essentially of the steps of (a) contacting a biological sample obtained from a subject to a pathogen detection agent under conditions that promote binding of the pathogen detection agent to the target pathogen if present in the sample; (b) isolating nucleic acids from pathogen bound by the pathogen detection agent; (c) amplifying the isolated nucleic acids using isothermal amplification; and (d) contacting the amplified nucleic acid to a toehold switch, where the toehold switch encodes at least a portion of a reporter protein and comprises one or more single-stranded toehold sequence domains that are complementary to a target pathogen nucleic acid or the reverse complement thereof, where the contacting occurs under conditions that allow translation of the coding domain in the presence of the target nucleic acid but not in the absence of the target nucleic acid, and detecting the reporter protein as an indicator that the target pathogen nucleic acid is present in the amplified nucleic acids. The pathogen detection agent can be a norovirus detection agent and the target pathogen nucleic acid is norovirus RNA. The norovirus detection agent can be a synbody. The synbody can comprise biotin. The biotin-containing synbody can be bound to a streptavidin-coated magnetic bead. Isolating can comprise a magnetic capture assay. The toehold switch can encode at least a portion of lacZ. The toehold switch can encode lacZ$\alpha$ and the amplified nucleic acids are contacted under conditions which promote formation of a lacZ tetramer. LacZ$\omega$ can be provided on a substrate to which the amplified nucleic acids are contacted. Target pathogen nucleic acid can be detected at concentrations in a range of zeptomoles/liter (zM). Target pathogen nucleic acid can be detected at concentration between about 270 zM to about 270 aM.

In another aspect, provided herein is a device for identifying a pathogen-associated nucleic acid, comprising a preserved paper test article, where a method provided herein is performed using the preserved paper test article. The paper test article can be preserved by freeze-drying.

In another aspect, provided herein is a synthetic norovirus-specific toehold switch sensor comprising a fully or partially double-stranded stem domain, a loop domain, a toehold domain, and at least a portion of a coding sequence of a reporter gene, where the toehold domain and at least a portion of the stem domain are complementary to a target norovirus RNA sequence. The sensor can comprise a RNA sequence selected from SEQ ID NOs:1-12.

In a further aspect, provided herein is a kit for detecting a pathogen-associated nucleic acid, comprising a plurality of preserved paper test articles, a pathogen detection agent, a plurality of toehold switches that encode at least a portion of a reporter protein and comprise one or more single-stranded toehold sequence domains that are complementary to a target pathogen nucleic acid or the reverse complement thereof, and an electronic optical reader. The pathogen detection agent can be a synbody.

In another aspect, provided herein is a kit for detecting a pathogen-associated nucleic acid, comprising a plurality of preserved test tube test articles, a pathogen detection agent, a plurality of toehold switches that encode at least a portion of a reporter protein and comprise one or more single-stranded toehold sequence domains that are complementary to a target pathogen nucleic acid or the reverse complement thereof, and an electronic optical reader. The pathogen detection agent can be a synbody. In some cases, the kit further comprises instructions for performing a method as provided herein.

INCORPORATION BY REFERENCE

All publications, patents, and patent applications mentioned in this specification are herein incorporated by reference in their entirety as if each individual publication, patent, and patent application was specifically and individually indicated to be incorporated by reference.

This application includes a sequence listing in computer readable form (a "txt" file) that is submitted herewith. This sequence listing is incorporated by reference herein.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

DETAILED DESCRIPTION

Figure 1:
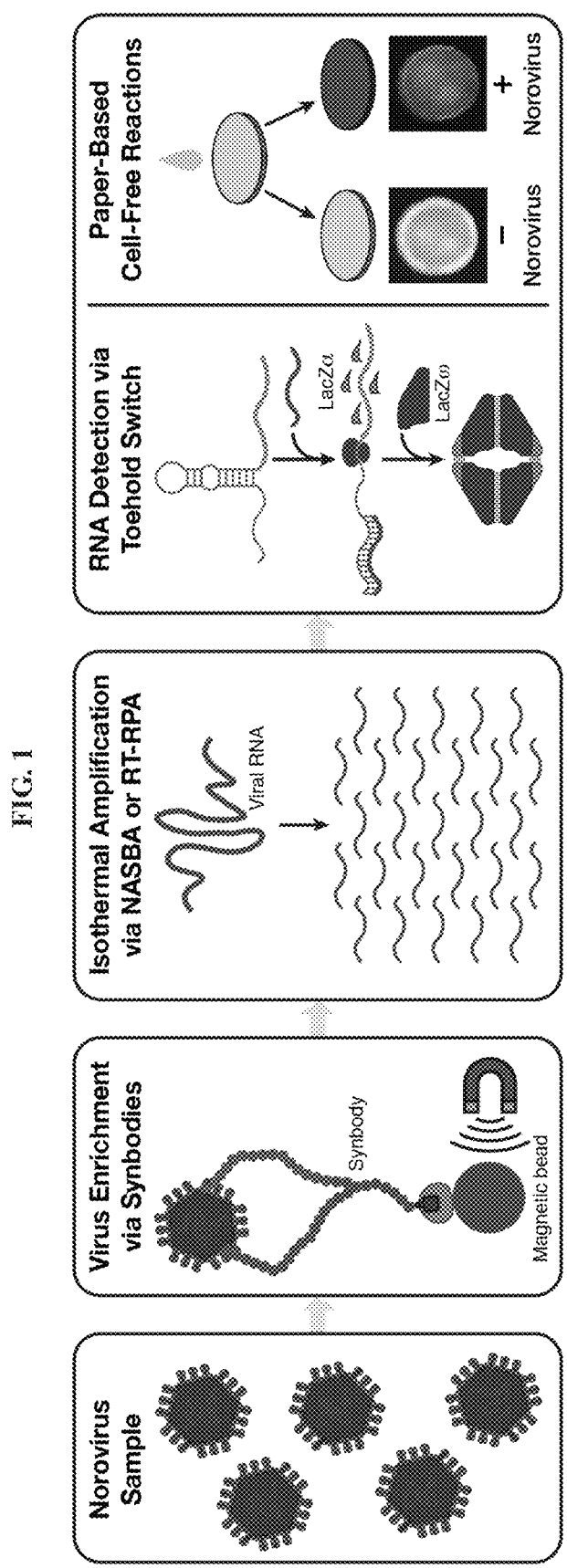
FIG. 1 is a schematic illustrating an embodiment of a norovirus detection assay using paper-based cell-free transcription-translation reactions. A norovirus sample is first enriched using synbodies and viral RNA amplified isothermally using nucleic acid sequence-based amplification (NASBA) or reverse transcriptase recombinase polymerase amplification (RT-RPA). The amplified nucleic acids are added to paper-based cell-free reactions where norovirus RNAs are detected by sequence-specific toehold switches. The toehold switches generate the lacZα peptide, which produces a purple-colored product after complementation with lacZω. Samples positive for norovirus can be identified by their purple color following the assay.

The methods and compositions provided herein are based at least in part on the inventors' development of a highly sensitive assay for detecting pathogen nucleic acids down to concentrations of 200 attomoles/liter (aM) in reactions that can be directly read by eye. Advantages of the methods and compositions provided herein are multifold and include, for example, low-cost identification of infectious agents (e.g., foodborne pathogens) in a versatile diagnostic assay that provides visible test results, does not require expensive thermal cycling and other laboratory equipment, and can be easily deployed for rapid diagnosis in the field. Moreover, the methods and compositions provided herein obviate the need for expensive equipment and facilitate decentralized assays.

Accordingly, in a first aspect, provided herein is a method of detecting a target pathogen nucleic acid in a sample. The method can comprise or consist essentially of the following steps: (a) contacting a biological sample obtained from a subject to a pathogen detection agent under conditions that promote binding of the pathogen detection agent to the target pathogen if present in the sample; (b) isolating nucleic acids from pathogen bound by the pathogen detection agent; (b) amplifying the isolated nucleic acids using isothermal amplification; and (c) contacting the amplified nucleic acid to a toehold switch, wherein the toehold switch encodes at least a portion of a reporter protein and comprises one or more single-stranded toehold sequence domains that are complementary to a target nucleic acid or the reverse complement thereof, where the contacting occurs under conditions that allow translation of the coding domain in the presence of the target nucleic acid but not in the absence of the target nucleic acid, and detecting the reporter protein as an indicator that the target pathogen nucleic acid is present in the amplified nucleic acids. By enriching for and amplifying nucleic acids of the target pathogen, the method allows for detection of a pathogen in a biological sample that is dilute or contains few copies of the target pathogen. In some cases, the methods permit target nucleic acid detection with femtomolar, attomolar, and zeptomolar detection limits. As demonstrated in the Examples section, the method enables detection of norovirus GII.4 Sydney from a stool sample down to concentrations of 270 aM without the use of a concentration step. The SI prefix "atto" represents a factor of $10^{18}$, or in exponential notation, 1E-18. The Examples also demonstrate that synbody-based enrichment of the virus can lower the detection limit by 1000-fold to 270 zeptomoles/ liter (zM). The SI prefix "zepto" represents a factor of $10^{-21}$, or in exponential notation, 1E-21.

As used herein, the term "pathogen" refers to any infectious agent and includes viruses, parasites, bacteria, fungi, and prions. By way of non-limiting example, pathogens may comprise viruses including, without limitation, noroviruses (e.g., Norwalk virus), flaviviruses, human immunodeficiency virus (HIV), Ebola virus, single stranded RNA viruses, single stranded DNA viruses, double-stranded RNA viruses, double-stranded DNA viruses. Other pathogens include but are not limited to parasites (e.g., malaria parasites and other protozoan and metazoan pathogens (*Plasmodia* species, *Leishmania* species, *Schistosoma* species, *Trypanosoma* species)), bacteria (e.g., *Mycobacteria*, in particular, *M. tuberculosis*, *Salmonella*, *Streptococci*, *E. coli*, *Staphylococci*), fungi (e.g., *Candida* species, *Aspergillus* species, *Pneumocystis jirovecii*, *Pneumocystis carinii*, and other *Pneumocystis* species), and prions. In some cases, the pathogenic microorganism, e.g. pathogenic bacteria, may be one which causes cancer in certain human cell types. An advantage of the methods described herein is that they can be applied for the detection and identification of essentially any nucleic acid-containing organism. Accordingly, the pathogen can be virtually any pathogen or infectious agent for which genetic information (e.g., gene sequences) is available. In other cases, the target nucleic acid is human in origin. In such cases, the methods can be employed to detect one or more target nucleic acids in a biological sample such as a biological sample obtained for forensic analysis, for genotyping, and the like.

Pathogen detection agents include, without limitation, antibodies, synbodies, peptides, polypeptides, and aptamers. Referring to FIG. 1, synbodies are useful pathogen detection agents for the methods provided herein. As used herein, the terms "synbody" and "synbodies" refer to synthetic peptide affinity ligands. In some cases, the synbody is a synthetic bivalent affinity ligand comprising or consisting essentially of two or more compounds such as peptides, joined by a linker, and identified as having affinity for the same target molecule (e.g., a protein of interest). Synbodies, can be developed by linking two low affinity 15-20 amino acid (aa) long peptides to produce a high affinity synbody for a target protein (e.g., a viral coat protein) or bacteria. Synbodies have affinities and specificities similar to antibodies. Unlike antibodies, however, which often lose their affinity as a pathogen strain evolves, synbodies have broad cross-affinity for multiple pathogen genotypes, which enables them to recognize and specifically bind to a range of pathogen genotypes. In some cases, the synbody is a norovirus synbody such as, for example, the norovirus synbodies disclosed in U.S. Pat. No. 9,766,239, which is incorporated by reference herein.

Specific binding refers to the binding of a compound to a target (e.g., a component of a sample) that is detectably higher in magnitude and distinguishable from non-specific binding occurring to at least one unrelated target. Specific binding can be the result of formation of bonds between particular functional groups or particular spatial fit (e.g., lock and key type) whereas nonspecific binding is usually the result of van der Waals forces. Specific binding does not however imply that a compound binds one and only one target. Thus, a compound can and often does show specific binding of different strengths to several different targets and only nonspecific binding to other targets. Preferably, different degrees of specific binding can be distinguished from one another as can specific binding from nonspecific binding.

Figures 5A, 5B, 5C, 5D:
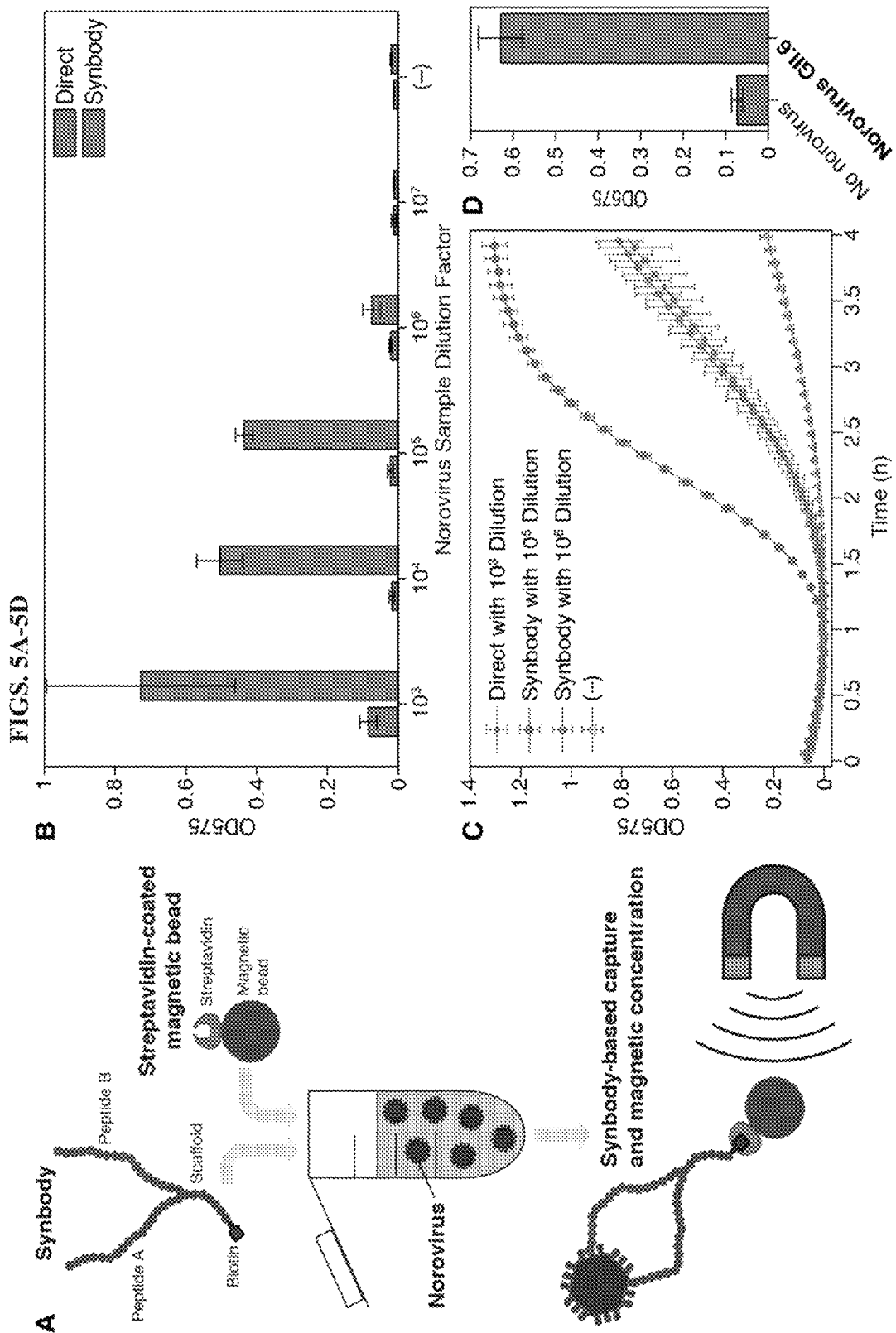
FIGS. 5A-5D illustrate implementation of a synbody-based capture and concentration method for norovirus detection. A, Illustration of the synbody enrichment technique. Biotin-labelled synbodies engineered to recognize diverse norovirus genotypes are used to bind to virus particles in a dilute solution and are in turn captured by streptavidin-coated magnetic beads. Magnetic capture enables concentration of the captured norovirus particles. B, Measurement of OD575 after two-hour cell-free reactions with toehold switch S2. Samples subject to synbody-based concentration and samples used directly without concentration were amplified by NASBA. The negative control (−) is a water-only sample. C, Time-course measurements of OD575 for synbody-concentrated samples compared to samples used directly. OD575 for a sample used directly after 1000-fold dilution is comparable to a concentrated sample initially diluted by $10^6$-fold. D, Detection of norovirus GII.6 from a stool sample using toehold switch S2 and updated NASBA primers for the GII.6 genome. OD575 measurements were taken after two hours of the paper-based cell-free reaction and using a norovirus-negative stool sample as comparison.

In certain embodiments, the synbody is tagged with biotin and then contacted to streptavidin-coated magnetic beads. In this manner, pathogen protein (e.g., viral particles) bound to the synbody-bead can be captured and concentrated using magnets. Referring to FIG. 5A, a synbody-based magnetic bead capture assay can be used to concentrate pathogen (e.g., norovirus) from dilute solutions. In this example, captured norovirus was heated to 95° C. to release norovirus RNA, and the released RNA was subjected to isothermal amplification and applied to paper-based cell-free systems containing a norovirus-specific toehold switch.

Figures 2A, 2B, 2C, 2D, 2E, 2F, 2G:
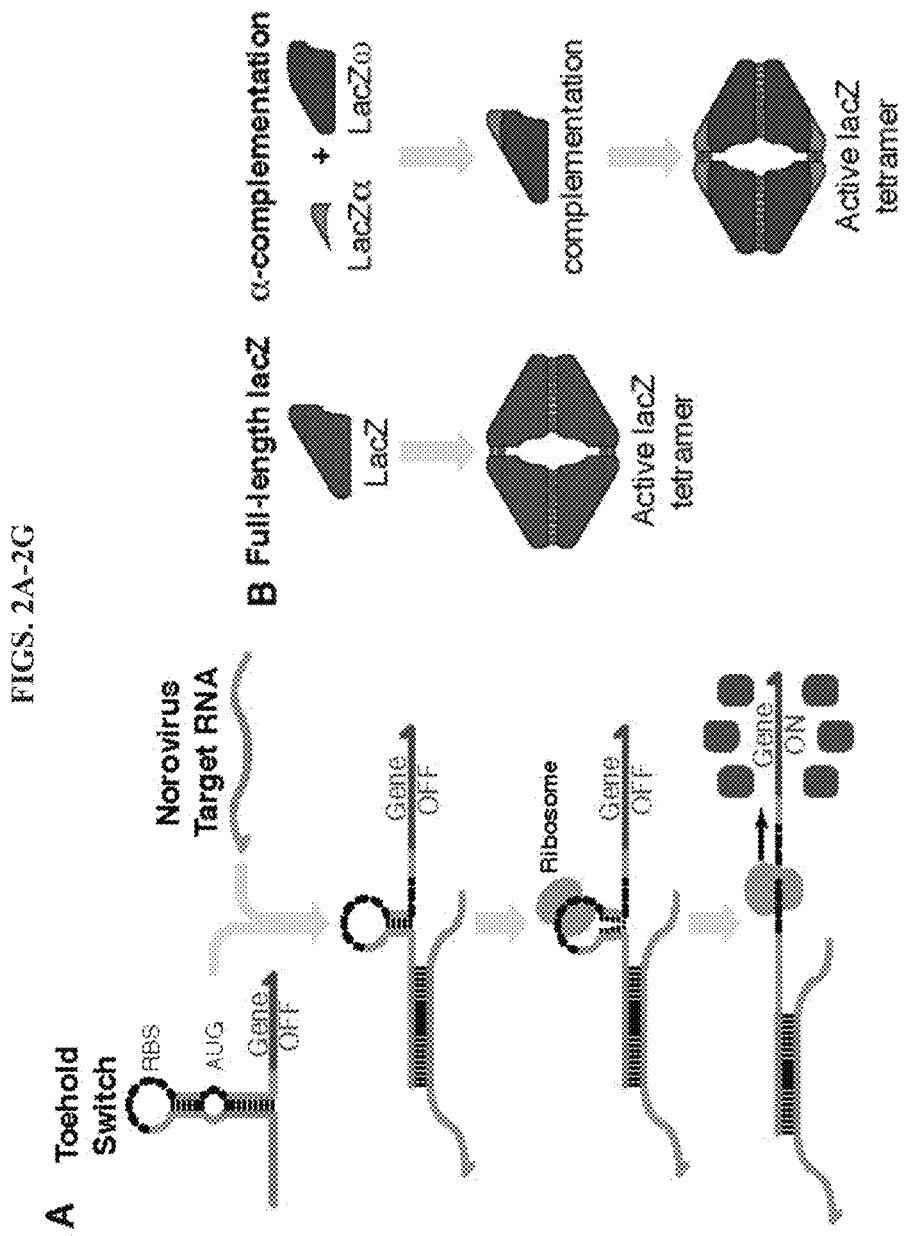
FIGS. 2A-2G demonstrate detection of norovirus target RNA using toehold switches and α-complementation. A, Schematic of toehold switch operation in response to the target RNA. A weak stem containing the ribosomal binding site (RBS) is retained after target binding. This stem unwinds during binding of the ribosome to enable translation of the output gene. B, Enzymatically active lacZ tetramer formation occurs directly for full-length lacZ, while lacZα and lacZω must first assemble via a-complementation prior to tetramer formation. C, D, Measurements of the fold change in lacZ production rate (C) and ΔOD575 (D) of six toehold switches targeting the sense orientation of the norovirus target RNA after two hours of the cell-free reaction. E, F, Measurements of the fold change in lacZ production rate (E) and ΔOD575 (F) of six toehold switches targeting the antisense orientation of the norovirus target RNA. Change in lacZ production rate was measured after 1 hour of cell-free reaction (C, E) and ΔOD575 was measured after 2 hours of cell-free reaction (D, F). G, OD575 for toehold switch A2 as function of cell-free reaction time when outputting full-length lacZ compared to lacZα in a reaction supplemented with pre-synthesized lacZω.

In certain embodiments, the method employs programmable riboregulators known as toehold switches. As used herein, the term "toehold switch" generally refers to a nucleic acid-based regulator of gene expression, configured to repress or activate translation of an open reading frame and thus production of a protein. Toehold switches, which are a type of prokaryotic riboregulator, activate gene expression in response to cognate RNAs with essentially arbitrary sequences. Gene regulation is achieved through the presence of a regulatory nucleic acid element (the cis-repressive RNA or crRNA) within the 5' untranslated region (5' UTR) of an mRNA molecule. The cis-repressive nucleic acid element (crRNA) forms a hairpin structure comprising a stem domain and a loop domain through complementary base pairing. The hairpin structure blocks access to the mRNA transcript by the ribosome, thereby preventing translation. In some embodiments, the stem domain of the hairpin structure sequesters the ribosome binding site (RBS). In some embodiments, including, for example, embodiments involving eukaryotic cells, the stem domain of the hairpin structure is positioned upstream of the start (or initiation) codon. As described in the Examples, that follow, toehold switches particularly useful for the methods provided herein are configured for lower leakage relative to previously described riboregulators. As illustrated in FIG. 2A, binding of a cognate target RNA to the updated toehold switch unwinds the lower half of the switch RNA hairpin and leaves the conserved upper stem-loop intact. This upper stem-loop is sufficiently weak to expose the RBS to enable translation to occur. Unlike earlier toehold switch mRNA sensors, the updated systems do not employ an RNA refolding domain downstream of the start codon, which could hamper translation of the output gene.

In some cases, toehold switches are synthetic (engineered) molecules. In other cases, toehold switches comprise endogenous, naturally occurring RNAs or regions thereof. See, for example, U.S. 2015/0275203. The stem domain can be as small as 12 bps, but in some cases will be longer than 12 bps, including 13, 14, 15, 16, 17, 18, 19, 20, or more base pairs in length. In other cases, the loop domain is complementary to a non-naturally occurring RNA. The toehold domain can be 5, 6, 7, 8, 9, 10, 11, 12, 13, 14, 15, 16, 17, 18, 19, 20, or more nucleotides in length.

The toehold switch further comprises a fully or partially double-stranded stem domain comprising an initiation codon, a loop domain comprising a RBS, and a coding domain. The unpaired region upstream of the RBS in a toehold switch can be shortened or lengthened to modulate protein output and, in turn, device dynamic range. In some cases, the toehold and stem domains are complementary in sequence to a naturally occurring RNA. In other cases, the sequence detected can also be the complement of the naturally occurring RNA. For example, after isothermal amplification, it is possible to transcribe the antisense of the RNA rather than the sense.

The toehold switch can further comprise a thermodynamically stable double-stranded stem domain, a loop domain comprising a ribosome binding site, and a coding domain. Preferably, the loop domain is 11 nucleotides or 12 nucleotides in length. In some cases, the length of loop domains can be increased or decreased, for example, to alter reaction thermodynamics.

In certain embodiments, the toehold switch is configured to detect a portion of a pathogen genome that is conserved among two or more species or strains of the pathogen. For example, the Examples that follow describe identifying conserved sequence regions of a norovirus GII genome suitable for isothermal amplification and toehold-switch-based detection. In some cases, toehold switches useful for the methods provided herein include, without limitation, synthetic norovirus-specific toehold switches that comprise a fully or partially double-stranded stem domain, a loop domain, a toehold domain, and at least a portion of a coding sequence of a reporter gene, wherein the toehold domain and at least a portion of the stem domain are complementary to a target norovirus RNA sequence. In some cases, synthetic norovirus-specific toehold switches comprise an RNA sequence selected from SEQ ID NOs:1-12 set forth in Table 1.

As shown in FIGS. 2A and 2B, the toehold switch can be operably linked to a reporter element (e.g., at least a portion of an *E. coli* lacZ reporter element encoding β-galactosidase) that is 3' to the hairpin structure. As used herein, the term "operably linked" refers to a relationship between two nucleic acid sequences wherein the production or expression of one of the nucleic acid sequences is controlled by, regulated by, modulated by, etc., the other nucleic acid sequence. Reporter proteins appropriate for the methods provided herein include, without limitation, enzymatic reporters (e.g., β-galactosidase, alkaline phosphatase, DHFR, CAT), fluorescent or chemiluminescent reporters (e.g., GFP variants, mCherry, luciferase, e.g., luciferase derived from the firefly (*Photinus pyralis*) or the sea pansy (*Renilla reniformis*) and mutants thereof), etc.

Any isothermal amplification protocol can be used according to the methods provided herein. Exemplary types of isothermal amplification include, without limitation, nucleic acid sequence-based amplification (NASBA), reverse transcriptase recombinase polymerase amplification (RT-RPA), loop-mediated isothermal amplification (LAMP), strand displacement amplification (SDA), helicase-dependent amplification (HDA), nicking enzyme amplification reaction (NEAR), signal mediated amplification of RNA technology (SMART), rolling circle amplification (RCA), isothermal multiple displacement amplification (IMDA), single primer isothermal amplification (SPIA), recombinase polymerase amplification (RPA), and polymerase spiral reaction (PSR, available at nature.com/articles/srep12723 on the World Wide Web).

In some cases, it may be advantageous to adapt the methods described herein for high-throughput, reproducible, and rapid detection, for example in a clinical setting. When output from the toehold switch is coupled to a reporter element, such as a LacZ reporter element or portion thereof, the riboregulator acts as a genetically encodable sensor and detectable probe for endogenous DNA or RNA (e.g., endogenous pathogen DNA, endogenous pathogen RNA) in a sample. For example, such toehold switches can be provided in a device configured for rapid, reproducible detection in a non-laboratory setting (e.g., clinical setting). In some cases, the device comprises a preserved paper test article, upon which any step(s) of the method provided herein can be performed. In preferred embodiments, the paper test article is preserved by freeze-drying. The reporter element can be a reporter protein, e.g., a polypeptide with an easily assayed enzymatic activity or detectable signal that is naturally absent from the host cell. Exemplary but non-limiting reporter proteins include lacZ, catalase, β-glucoronidase, xylE, GFP, RFP, YFP, CFP, neomycin phosphotransferase, luciferase, mCherry, and derivatives or variants thereof. In some embodiments of any of the aspects, the reporter protein is suitable for use in a colorimetric assay. Examples of genes encoding fluorescent proteins that may be used in accordance with the invention include, without limitation, those proteins provided in U.S. Patent Application No. 2012/0003630 (see Table 59 therein), incorporated herein by reference.

In certain embodiments, alpha-complementation is employed to decrease assay times and strengthen output from the cell-free transcription-translation reactions. As shown in FIG. 2B, it may be advantageous to divide the lacZ enzyme into two peptides termed α and ω. The lacZ α-peptide (lacZα) consists of the first 50 to 59 residues from the N terminus of lacZ and the ω-peptide (lacZω) comprises the remaining ~970 lacZ residues. The complete lacZ must form a tetramer before it becomes catalytically active; however, lacZω cannot form a tetramer on its own as it lacks residues critical for assembly. As a result, both lacZα and lacZω must be expressed before complementation occurs and an active lacZ tetramer can assemble. As demonstrated in the Examples section, the use of a-complementation, in which the lacZα and lacZω peptides complement to form the active lacZ enzyme, can reduce the time to detection of the paper-based assay by up to 23 minutes or 43% compared to experiments employing the full-length lacZ as the toehold switch output.

In some cases, DNA encoding the norovirus-specific toehold switches may be cloned into vectors upstream of the lacZα open reading frame. Such constructs can be used in paper-based cell-free reactions when supplemented with lacZω. In some cases, lacZω is provided as a pre-synthesized compound on the reaction substrate (e.g., a paper-based cell-free reaction substrate). For example, the toehold switch can encode at least a portion of lacZ such as lacZα. The amplified nucleic acids are contacted to cell-free reaction substrate to which lacZω is provided as a pre-synthesized peptide and under conditions which promote formation of a lacZ tetramer.

Other complementation reporter systems can be used for the methods described herein. For example, Green Fluorescent Protein (GFP) can be split by removing a single beta strand from its barrel structures to generate a large molecular weight GFP1-10 peptide, comprising beta strands one through 10, and a small molecular weight GFP11 peptide, comprising the 11$^{th}$ beta strand. When both peptides are present, they spontaneously reassemble into a fluorescently active combined protein. Split GFP systems are described, for example, at nature.com/articles/ncomms11046 and nature.com/articles/s41467-017-00494-8 on the World Wide Web. sfCherry, an improved folding version of mCherry, and mNeonGreen2 can also be split in similar ways and provide analogous fluorescence readout via complementation. There are multiple versions of split cas9 that can also be activated through complementation. See, for example, nature.com/articles/nbt.3149 and pnas.org/content/112/10/2984 on the World Wide Web.

Any appropriate sample can be used according to the methods provided herein. In some cases, the sample is a biological sample obtained from an individual (e.g., a human subject, a non-human mammal). The sample is, in some cases, a diagnostic sample. The sample type will vary depending on the target pathogen. For example, norovirus, including human forms of norovirus (i.e., Norwalk virus), can be detected in stool specimens, sputum, blood or vomitus of diseased individuals. Norovirus can also be present in body tissues, such as brain tissue, in an infected mammalian organism. Accordingly, a diagnostic sample for detecting norovirus can be a stool sample, a sputum sample, a vomitus sample, a tissue sample, or a blood sample. Samples appropriate for use according to the methods provided herein can also include, without limitation, food samples, drinking water, environmental samples, and agricultural products. In some cases, samples appropriate for use according to the methods provided herein are "non-biological" in whole or in part. Non-biological samples include, without limitation, plastic and packaging materials, paper, clothing fibers, and metal surfaces. In certain embodiments, the methods provided herein are used in food safety and food biosecurity applications, such as screening food products and materials used in food processing or packaging for the presence of pathogens in biological and/or non-biological samples.

Other applications for which the methods provided herein include, without limitation, profiling species in an environment (e.g., water); profiling species in an human or animal microbiome; food safety applications (e.g., detecting the presence of a pathogenic species, determining or confirming food source/origin such as type of animal or crop plant); obtaining patient expression profiles (e.g., detecting expression of a gene or panel of genes (e.g., biomarkers)) to monitor the patient's response to a therapeutic regimen, to select a therapeutic regimen suitable for the patient, or to detect exposure of the patient to a toxin or environmental agent that affects expression of the gene or a panel of genes.

In some cases, the device is used with a portable electronic reader. In this manner, the electronic reader serves as companion technology that provides robust and quantitative measurements of device outputs. In some embodiments, the electronic reader comprises readily available consumer components, open-source code, and laser-cut acrylic housing, and is powered by a rechargeable lithium ion battery. The electronic reader can further comprise an onboard data storage unit. In some cases, to achieve sensitive detection of toehold switch signal output, an acrylic chip that holds the freeze-dried, paper-based reactions is placed into the reader between a light source (e.g., to read optical density at excitation and emission wavelengths of light appropriate for and characteristic of a particular detectable reporter) and electronic sensors. In some cases, the light source is a light emitting diode (LED) light source. Samples can be read using onboard electronics. In this manner, a portable electronic reader can provide low-noise measurements of changes associated with the reporter element including changes in light transmission due to LacZ-mediated color change.

In certain embodiments, provided herein is a device for identifying a pathogen-associated nucleic acid, comprising a preserved paper test article, wherein the methods described herein are performed using the preserved paper test article. In some cases, the paper test article is preserved by freeze-drying.

Articles of Manufacture

In another aspect, the present invention provides articles of manufacture useful for detecting a pathogen in a sample according to the methods provided herein. In certain embodiments, the article of manufacture is a kit for detecting norovirus, where the kit comprises a norovirus detecting agent, a plurality of preserved paper test articles as described herein, and an electronic optical reader. Optionally, a kit can further include instructions for performing the pathogen detection methods provided herein.

In certain embodiments, provided herein is a kit for detecting a pathogen-associated nucleic acid, where the kit comprises a plurality of preserved paper test articles, a pathogen detection agent, a plurality of toehold switches that encode at least a portion of a reporter protein and comprise one or more single-stranded toehold sequence domains that are complementary to a target pathogen nucleic acid or the reverse complement thereof, and an electronic optical reader. In some cases, the kit also comprises instructions for performing the pathogen detection methods provided herein.

In other embodiments, provided herein is a kit for detecting a pathogen-associated nucleic acid, where the kit comprises a plurality of preserved test tube test articles, a pathogen detection agent, a plurality of toehold switches that encode at least a portion of a reporter protein and comprise one or more single-stranded toehold sequence domains that are complementary to a target pathogen nucleic acid or the reverse complement thereof, and an electronic optical reader. In some cases, the kit also comprises instructions for performing the pathogen detection methods provided herein.

Unless defined otherwise, all technical and scientific terms used herein have the same meaning as commonly understood by one of ordinary skill in the art to which the invention pertains. All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein, the terms "approximately" or "about" in reference to a number are generally taken to include numbers that fall within a range of 5% in either direction (greater than or less than) the number unless otherwise stated or otherwise evident from the context (except where such number would exceed 100% of a possible value). Where ranges are stated, the endpoints are included within the range unless otherwise stated or otherwise evident from the context.

The present invention has been described in terms of one or more preferred embodiments, and it should be appreciated that many equivalents, alternatives, variations, and modifications, aside from those expressly stated, are possible and within the scope of the invention.

EXAMPLES

This section demonstrates a paper-based, cell-free platform for the detection of the prevalent GII.4 Sydney norovirus genotype (FIG. 1). Beginning from fecal samples or a dilute solution containing the virus, the assay employs biotin-labelled synthetic peptide affinity ligands known as synbodies to capture norovirus particles and concentrate the captured particles using streptavidin-coated magnetic beads. A brief heating step is used to release the norovirus RNA, and either NASBA or reverse transcriptase RPA (RT-RPA) is employed to amplify the viral RNA. The amplification products are then added to paper-based cell-free reactions where norovirus-specific toehold switches are used to verify their sequences and produce the lacZα peptide, which provides a visual reaction readout. We demonstrate that this assay enables detection of norovirus target RNAs down to concentrations of 200 aM without the use of a concentration step, and further show that synbody-based enrichment of the virus can lower the detection limit by 1000-fold when applied to a clinical fecal sample. We also demonstrate that the use of a-complementation, in which the lacZα and lacZω peptides complement to form the active lacZ enzyme, can reduce the time to detection of the paper-based assay by up to 23 minutes or 43% compared to experiments employing the full-length lacZ as the toehold switch output. These results expand the range of sample types and viruses that can be analyzed using paper-based cell-free systems and provide new strategies to improve the sensitivity and reduce the time of these inexpensive diagnostic assays.

Materials and Methods

Norovirus samples and bacterial strains: Stool samples positive for the norovirus GII.4 Sydney genotype and the norovirus GI.2 genotype were generously provided by Jan Vinjé from the National Calicivirus Laboratory at the Centers for Disease Control and Prevention (CDC). *Escherichia coli* MG1655 (ATCC, 700926), methicillin-resistant *Staphylococcus aureus* MRSA252 (ATCC, BAA-1720), and *Bacillus subtilis* 168 (ATCC, 23857) were used for assay cross-reactivity experiments. For these experiments, RNA from the bacteria was extracted using a Quick-RNA Fungal/Bacterial Miniprep Kit (Zymo Research) following the manufacturer's instructions. To obtain purified viral RNA for cross-reactivity experiments, 5 µL of GII.4, GI.2, and GI.6 positive stool samples were suspended in 140 µL RNase-free water. The viral RNA was extracted by using QIAamp DSP Viral RNA Mini Kit (Qiagen, U.S.A.) according to the manufacturer's instructions. RNAs were eluted with 50 µL RNase-free water and stored at −80° C. *E. coli* DH5α (ThermoFisher Scientific) was used for cloning of toehold switch plasmids.

In silico selection of toehold switch designs: An updated version of the selection algorithm described previously[32] was used to identify toehold switches for detection of norovirus RNA. The algorithm facilitated selection six promising designs from a set of over 100 candidate toehold switches generated from each norovirus target RNA. Candidate devices were designed to bind to a 36-nt continuous region of the norovirus target RNA. Putative toehold switches were generated at 1-nt increments along the norovirus target RNA and multiple ensemble defect levels were computed for each sensor based on its deviation from the ideal secondary structure of the toehold switch. Ensemble defects were calculated for the toehold switch 5' end through to the 3' end of the hairpin ($d_{min\_sensor}$), the toehold domain of the toehold switch ($d_{toehold}$), the binding site of the toehold switch within the target RNA ($d_{binding\_site}$), and the toehold switch region starting with the base immediately 3' of the target RNA binding site and extending 31 nts beyond the last base on the 3' end of the hairpin ($d_{active\_sensor}$).

For the latter two parameters, the ensemble defect was calculated based on a completely single-stranded ideal secondary structure. The parameter $d_{active\_sensor}$ was intended to provide a measure of any secondary structures in the activated toehold switch that could interfere with translation after binding to the target RNA. In addition to ensemble defects, the equilibrium fraction f of target/toehold switch complexes in a system with equimolar concentrations of target and toehold switch RNAs was calculated as a measure of the affinity of the two RNAs. In practice, this parameter was almost always equal to 1. Designs that produced in-frame stop codons in the output gene were eliminated from further consideration. Each of the parameters was then normalized such that their maximum value across the set of putative designs for a given target RNA was equal to 1. These normalized parameters, designated by an overscore, were then inserted into a scoring function s:

$$s = 5\bar{d}_{toehold} + 4\bar{d}_{active\_sensor} + 2\bar{d}_{min\_sensor} + 2\bar{d}_{binding\_site} + (1-f)$$

Toehold switches displaying the lowest values of s and screened to have f>0.9 were selected for experimental testing. Sequences of the toehold switches generated by the algorithm are provided in Table 1 along with those of the norovirus target regions. The weighting coefficients used in the scoring function were determined empirically based on testing of earlier toehold switch mRNA sensor designs[30, 32].

TABLE 1

Toehold switch and norovirus target RNA sequences

| Name | RNA Sequence |
|---|---|
| Toehold switch S1 RNA | GGGCCAUCUUCAUUCACAAAACUGGGGAGCCAGAUUGCGAGGACUUUA GAACAGAGGAGAUAAAGAUGUCGCAAUCUGGAACCUGGCGGCAGCGC AAGAAGAUG (SEQ ID NO: 1) |
| Toehold switch S2 RNA | GGGAUCGCCCUCCCACGUGCUCAGAUCUGAGAAUCUCAUGGACUUUA GAACAGAGGAGAUAAAGAUGAUGAGAUUCUCAACCUGGCGGCAGCGC AAGAAGAUG (SEQ ID NO: 2) |
| Toehold switch S3 RNA | GGGACAAAACUGGGAGCCAGAUUGCGAUCGCCCUCCCACGGACUUUA GAACAGAGGAGAUAAAGAUGGUGGGAGGGCGAACCUGGCGGCAGCGC AAGAAGAUG (SEQ ID NO: 3) |
| Toehold switch S4 RNA | GGGCUGGGACGAGGUUGGCUGCGGACCCAUCAGAUGGGUGGACUUUA GAACAGAGGAGAUAAAGAUGACCCAUCUGAUAACCUGGCGGCAGCGC AAGAAGAUG (SEQ ID NO: 4) |
| Toehold switch S5 RNA | GGGUCAUUCGACGCCAUCUUCAUUCACAAAACUGGGAGGGACUUUAG AACAGAGGAGAUAAAGAUGCUCCCAGUUUUAACCUGGCGGCAGCGCA AGAAGAUG (SEQ ID NO: 5) |
| Toehold switch S6 RNA | GGGAGCCAGAUUGCGAUCGCCCUCCCACGUGCUCAGAUCGGACUUUA GAACAGAGGAGAUAAAGAUGGAUCUGAGCACAACCUGGCGGCAGCGC AAGAAGAUG (SEQ ID NO: 6) |
| Toehold switch A1 RNA | GGGUCUGAUGGGUCCGCAGCCAACCUCGUCCCAGAGGUCGGACUUUA GAACAGAGGAGAUAAAGAUGGACCUCUGGGAAACCUGGCGGCAGCGC AAGAAGAUG (SEQ ID NO: 7) |
| Toehold switch A2 RNA | GGGUGGGAGGGCGAUCGCAAUCUGGCUCCCAGUUUUGUGGACUUUAG AACAGAGGAGAUAAAGAUGACAAAACUGGGAACCUGGCGGCAGCGCA AGAAGAUG (SEQ ID NO: 8) |

TABLE 1 -continued

Toehold switch and norovirus target RNA sequences

| Name | RNA Sequence |
|---|---|
| Toehold switch A3 RNA | GGGUGUGAAUGAAGAUGGCGUCGAAUGACGCCAACCCAUGGACUUUA GAACAGAGGAGAUAAAGAUGAUGGGUUGGCGAACCUGGCGGCAGCGC AAGAAGAUG (SEQ ID NO: 9) |
| Toehold switch A4 RNA | GGGAGAUCUGAGCACGUGGGAGGGCGAUCGCAAUCUGGCGGACUUUA GAACAGAGGAGAUAAAGAUGGCCAGAUUGCGAACCUGGCGGCAGCGC AAGAAGAUG (SEQ ID NO: 10) |
| Toehold switch A5 RNA | GGGAUCGCAAUCUGGCUCCCAGUUUUGUGAAUGAAGAUGGGACUUUA GAACAGAGGAGAUAAAGAUGCAUCUUCAUUCAACCUGGCGGCAGCGC AAGAAGAUG (SEQ ID NO: 11) |
| Toehold switch A6 RNA | GGGUCGAAUGACGCCAACCCAUCUGAUGGGUCCGCAGCCGGACUUUA GAACAGAGGAGAUAAAGAUGGGCUGCGGACCAACCUGGCGGCAGCGC AAGAAGAUG (SEQ ID NO: 12) |
| Norovirus GII.4 sense target | AUGGAUUUUUACGUGCCCAGGCAAGAGCCAAUGUUCAGAUGGAUGAG AUUCUCAGAUCUGAGCACGUGGGAGGGCGAUCGCAAUCUGGCUCCCA GUUUUGUGAAUGAAGAUGGCGUCGAAUGACGCCAACCCAUCUGAUGG GUCCGCAGCCAACCUCGUCCCAGAGGUCAACAAUGAGGUUAUGGCUU UGGAGCCCGU (SEQ ID NO: 13) |
| Norovirus GII.4 antisense target | ACGGGCUCCAAAGCCAUAACCUCAUUGUUGACCUCUGGGACGAGGUU GGCUGCGGACCCAUCAGAUGGGUUGGCGUCAUUCGACGCCAUCUUCA UUCACAAAACUGGGAGCCAGAUUGCGAUCGCCCUCCCACGUGCUCAGA UCUGAGAAUCUCAUCCAUCUGAACAUUGGCUCUUGCCUGGGCACGUA AAAAUCCAU (SEQ ID NO: 14) |
| Norovirus GII.P17 sense target | AUGGAUUUUUAUGUGCCCAGACAAGAGUCAAUGUUCAGAUGGAUGAG GUUCUCAGAUCUAAGCACAUGGGAGGGCGAUCGCAAUCUGGCUCCCA GUUUUGUGAAUGAAGAUGGCGUCGAAUGACGCCGCUCCAUCUAAUGA UGGUGCUGCUGGUCUCGUACCAGAGGGCAACAACGAG (SEQ ID NO: 15) |
| Norovirus GII.17 sense target | AUGGAUUUUUAUGUGCCCAGACAAGAGUCAAUGUUCAGAUGGAUGAG GUUCUCAGAUCUAAGCACAUGGGAGGGCGAUCGCAAUCUGGCUCCCA GUUUUGUGAAUGAAGAUGGCGUCGAAUGACGCCGCUCCAUCUAAUGA UGGUGCUGCUGGUCUCGUACCAGAGGGCAACAACGAG (SEQ ID NO: 16) |
| Norovirus GII.6 antisense target | UGGAGUUUUAUGUGCCCAGACAAGAGGCCAUGUUCAGGUGGAUGAGA UUCUCUGACCUCAGCACAUGGGAGGGCGAUCGCAAUCUUGCUCCCGA GGGUGUGAAUGAAGAUGGCGUCGAAUGACGCUGCUCCAUCGAAUGAU GGUGCUGCCAACCUCGUACCAGAGGCCAACAAUGAGGUUAUGGC (SEQ ID NO: 17) |

Figure 6:
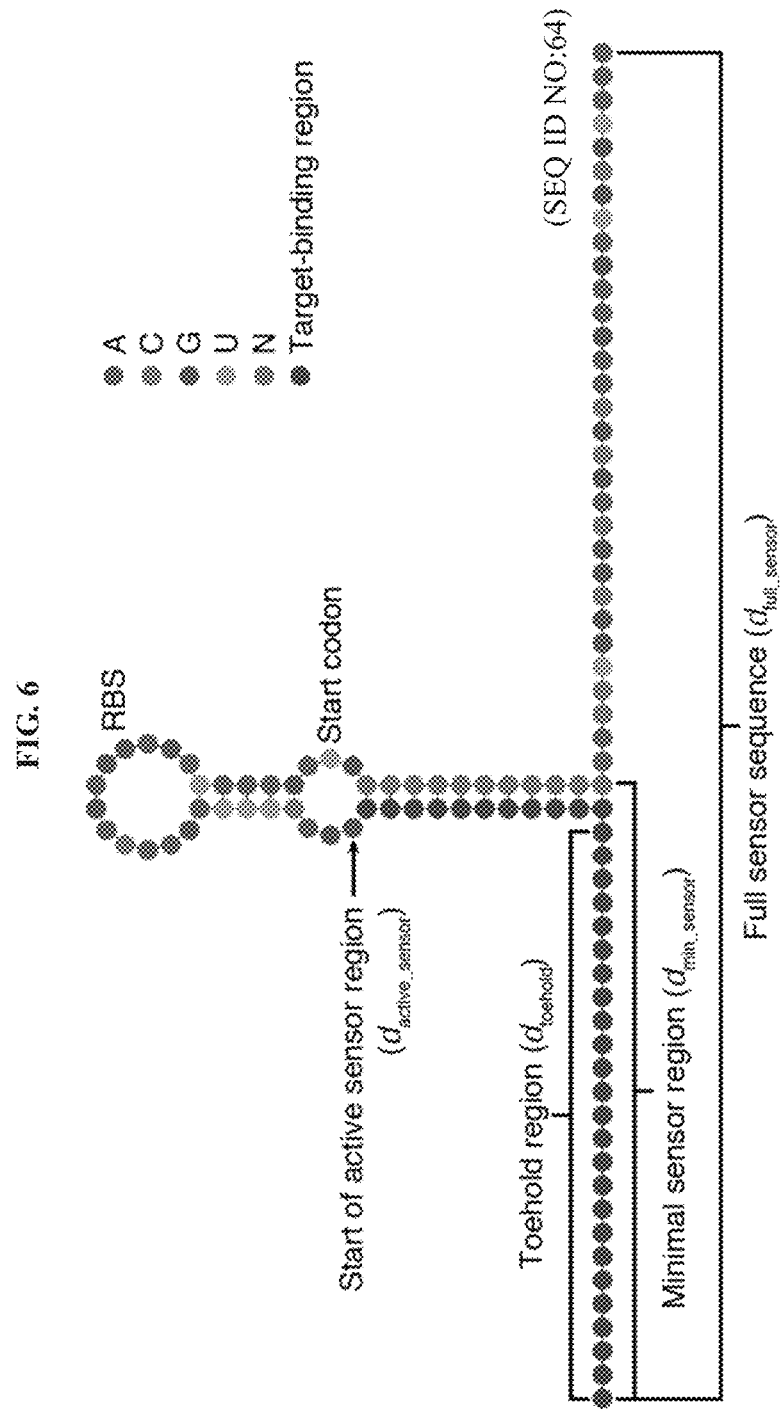
FIG. 6 is a schematic of toehold switch regions used for calculation of design ensemble defect parameters. The full sensor sequence used for calculation of $d_{full\_sensor}$ is shown along with subsequences spanning the toehold region ($d_{toehold}$) and the toehold and hairpin regions ($d_{min\_sensor}$). The start of the active sensor region is indicated by the arrow and begins at the base that falls 1 nt after the target binding region. The red target-binding region and the gray N bases are the only ones that change for each device.

Calculation of Ensemble Defects for Toehold Switch Designs: Ensemble defect levels were calculated using NUPACK for toehold switch designs over the regions specified in the main text and indicated in FIG. 6. The toehold switch designs for norovirus contained a conserved upper hairpin domain with the sequence GGACUUUAGAAC AGAGGAGA UAAAG AUG (SEQ ID NO:18), with the RBS and start codon shown in bold, and a 31-nt linker between the sensor and the output gene with the sequence AACCUGGCGGCAGCGCAAGAAGAUGCGUAAA (SEQ ID NO:19). The parameters $d_{min\_sensor}$ and $d_{toehold}$ were calculated by first computing the pairwise binding probabilities for the toehold switch sequence from the 5' end through to the 31st base beyond the 3' end of the hairpin (i.e., the full sequence shown in FIG. 6). These binding probabilities were then used to compute the ensemble defect from the specified sequence regions of $d_{min\_sensor}$ and $d_{toehold}$ using the target secondary structures shown in FIG. 6. Calculating the ensemble defect in this way enabled the effect of sequences outside the main region of interest to be considered for design purposes. For $d_{binding\_site}$, the ensemble defect was calculated in an analogous manner using the pairwise binding probabilities of the complete target RNA sequence and specifying a completely single-stranded ideal secondary structure in the binding site region. For $d_{active\_sensor}$, the ensemble defect was calculated directly from the sequence region starting from the base indicated in FIG. 6. A completely single-stranded secondary structure was used for assessing design quality for $d_{active\_sensor}$.

In addition to the four terms above, we calculated two additional ensemble defect parameters during the design process. The term $d_{full\_sensor}$ was generated by computing the ensemble defect for the full toehold switch sequence and structure shown in FIG. 6. The term $d_{min\_target}$ was generated by taking the 36-nt sequence targeted by the toehold switch and computing its ensemble defect with a completely single-stranded ideal structure.

Assessment and Further Optimization of Toehold Switch Selection Algorithm: To determine the effectiveness of the described toehold switch selection method, we have taken experimental fold change in lacZ production data (FIGS. 7C, 7E) and investigated if these data display significant correlations with the selection scoring function and the six computed ensemble defect parameters. Correlations between these parameters and the experimental results were assessed using $R^2$ values and regression coefficients generated from the Matlab multiple linear regression using least squares function regress. For these regressions, a column of ones was appended to the matrix of predictor variables to allow the model to include a constant term or offset.

Figures 7A, 7B, 7C, 7D, 7E, 7F, 7G, 7H, 7I, 7J, 7K, 7L:
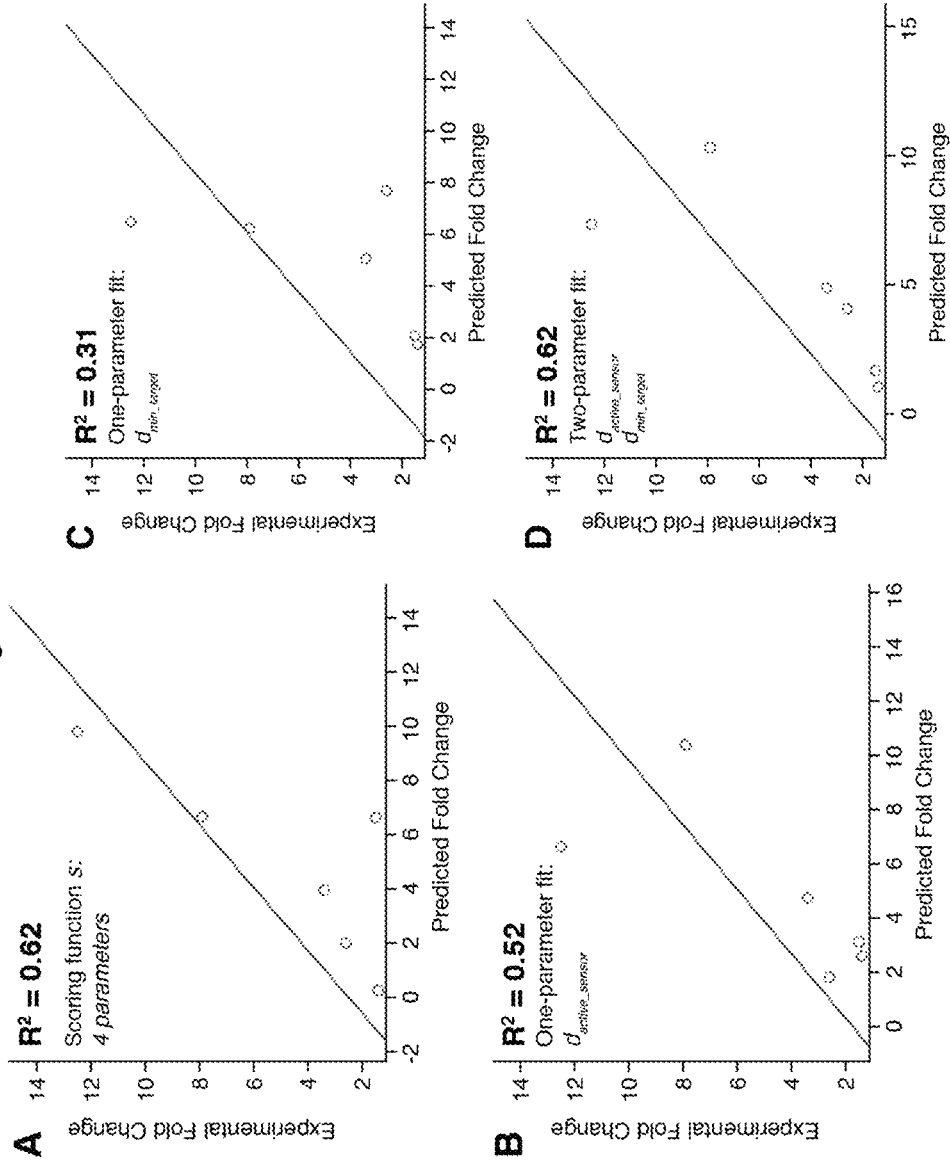
FIGS. 7A-7L are a series of linear regressions to detect correlations between toehold switch design parameters and their fold change performance for norovirus detection. (A-D) Linear regressions applied only to the set of antisense RNA sensors that provided overall better dynamic range. A two-parameter fit (D) is able to match the correlation with experimental results provided by a four-parameter fit. (E-H) Linear regressions applied only to the set of sense RNA sensors. No correlation is observed with the design scoring function s (E). One- and two-parameter fits also do not show much correlation with the experimental results. (I-L) Linear regressions applied to the full set of 12 toehold switches. Use of the same set of predictor variables in the scoring function s show limited agreement. However, linear regressions with increasing numbers of parameters provide much stronger correlations (J-L), ultimately reaching $R^2=0.60$ for a four-parameter regression.

FIG. 7A shows the linear regression obtained using experimental fold change from the toehold switches for the antisense target and the design scoring function s. We found that the scoring function, which made use of four ensemble defect parameters, provided a fairly strong correlation with the experimental data with $R^2=0.62$. We then examined the correlations between the antisense experimental data and the set of six ensemble defect parameters. The two parameters that showed the strongest correlations were $d_{active\_sensor}$ and $d_{min\_target}$, which yielded $R^2$ of 0.52 and 0.31, respectively (see FIGS. 7B-7C). A two-parameter linear regression combining both these terms provided $R^2=0.62$, which matched the correlation observed for the four-parameter scoring function.

We applied the same series of analyses to the set of toehold switches for the sense norovirus target. However, these devices showed much weaker correlations between design parameters and experimental results (see FIGS. 7E-7H). The scoring function did not display any correlation with the fold change in lacZ ($R^2=0.07$) and the top two single-parameter fits did not display strong correlations, $R^2=0.26$ and $R^2=0.20$ for $d_{binding\_site}$ and $d_{active\_sensor}$, respectively. Furthermore, no improvements were observed by combining the two parameters into the same regression.

Since the terms used in the scoring function were originally normalized for each target RNA, we could not use the scoring function directly to determine if it was highly correlated with the experimental results from all 12 devices since they bound to different target RNAs. Instead, we took the fold change experimental results and supplied the regression with the set of the four predictor variables used by the scoring function but in non-normalized form: $d_{min\_sensor}$, $d_{toehold}$, $d_{binding\_site}$, and $d_{active\_sensor}$. (Note: The fifth predictor variable f, the equilibrium fraction, used in the scoring function was equal to one for all devices tested). In this case, the linear regression provided limited correlation with $R^2=0.29$ (see FIG. 7I). To determine if other combinations of ensemble defect parameters could provide a stronger correlation with the experimental data, we computed linear regressions for all two-, three-, and four-parameter combinations as shown in FIGS. 7J-7L. We found that the combination of $d_{binding\_site}$ and $d_{active\_sensor}$ were most effective for the two-parameter fits, yielding $R^2=0.42$, a substantial increase over the scoring function combination. Addition of $d_{full\_sensor}$ to the pair provided the best three-parameter fit with another sizeable increase in fit quality to $R^2=0.57$. Finally, the optimal four-parameter fit, which added $d_{min\_target}$ to the trio of predictor variables, provided a small increase in $R^2$ to 0.60.

The three- and four-parameter linear regressions generated the following equations for predicting the fold change for the toehold switch sensors:

Three Parameter Fit ($R^2=0.57$):

$$\text{Fold change} = -71.7\, d_{full\_sensor} - 49.1\, d_{active\_sensor} - 22.6\, d_{binding\_site} + 54.3$$

Four-Parameter Fit ($R^2=0.60$):

$$\text{Fold change} = -93.2\, d_{full\_sensor} - 43.3\, d_{active\_sensor} - 22.1\, d_{binding\_site} - 9.4\, d_{min\_target} + 61.3$$

For both these linear fitting functions, negative coefficients are used in front of all of the ensemble defect parameters as expected, since lower defect levels should lead to higher toehold switch performance (i.e. fold change). In addition, the parameters $d_{full\_sensor}$, $d_{active\_sensor}$, and $d_{binding\_site}$ are listed from highest to lowest fitting function weighting factor. These three parameters define the most critical functional elements of the toehold switch devices. A properly folded secondary structure of the full sensor is required to provide a toehold region for target binding and a strong hairpin structure to repress translational leakage. The active sensor requires a translation start site with low secondary structure to promote rapid production of the output gene. Lastly, a binding site with low secondary structure helps ensure that the site is accessible for sensor binding. We expect that design selection algorithms can be further improved using strategies similar to the one described here and using much larger libraries of toehold switches to probe a wider range of sensor and target sequences experimentally.

Toehold switch plasmid construction: Synthetic DNA (Integrated DNA Technologies) encoding the norovirus-specific toehold switch sensors was amplified by PCR and inserted into plasmids using Gibson assembly with 30-bp overlap regions. Sequences of the toehold switches and the norovirus targets are provided in Table 1. Plasmids and DNA templates for transcription were constructed using conventional molecular biology techniques. The sequences of the plasmids were confirmed using Sanger sequencing (DNASU Sequencing Core, Tempe). The list of plasmids used in this work are provided in Table 2. Maps of these plasmids are presented in FIG. 10-FIG. 24. Sequences of the primers used for plasmid construction are listed Table 3. This table lists the source template amplified by each primer pair and indicates what plasmid was produced following Gibson assembly of the resulting PCR products. The synthetic DNA sequences used to generate toehold switches for insertion into plasmids are listed in Table 4. This table also contains the primers used for Sanger sequencing of the plasmids.

TABLE 2

List of Plasmids

| Name | Marker | Description |
| --- | --- | --- |
| pAT_T7_HisLacZ (SEQ ID NO: 69) | Amp | T7 RNAP-driven expression of N-terminal His-tagged lacZ. pET15b backbone. |
| ZIKV_Sensor_27B_LacZ (Addgene #: 75006) | Kan | T7 RNAP-driven expression of Zika virus sensing toehold switch with lacZ reporter. pCOLAduet backbone. |
| pDM_T7_HisLacZomega | Amp | T7 RNAP-drive expression of N-terminal His-tagged lacZω. pET15b backbone. |
| pDM_noro_S1_lacZA (SEQ ID NO: 77) pDM_noro_S2_lacZA (SEQ ID NO: 78) | Kan | T7 RNAP-driven expression of norovirus sense orientation toehold switches (S1 to S6) with a lacZα reporter. pCOLAduet backbone. |

TABLE 2-continued

| | List of Plasmids | |
|---|---|---|
| Name | Marker | Description |
| pDM_noro_S3_lacZA (SEQ ID NO: 79) | | |
| pDM_noro_S4_lacZA (SEQ ID NO: 80) | | |
| pDM_noro_S5_lacZA (SEQ ID NO: 81) | | |
| pDM_noro_S6_lacZA (SEQ ID NO: 82) | | |
| pDM_noro_A1_lacZA (SEQ ID NO: 70) | Kan | T7 RNAP-driven expression of norovirus antisense orientation toehold switches (A1 to A6) with a lacZα reporter. pCOLAduet backbone. |
| pDM_noro_A2_lacZA (SEQ ID NO: 72) | | |
| pDM_noro_A3_lacZA (SEQ ID NO: 73) | | |
| pDM_noro_A4_lacZA (SEQ ID NO: 74) | | |
| pDM_noro_A5_lacZA (SEQ ID NO: 75) | | |
| pDM_noro_A6_lacZA (SEQ ID NO: 76) | | |
| pDM_noro_A2_lacZ (SEQ ID NO: 71) | Kan | T7 RNAP-driven expression of norovirus antisense orientation toehold switch A2 with full-length lacZ reporter. pCOLAduet backbone. |

TABLE 3

List of PCR Primers Used for Plasmid Construction

| Primer Name | Sequence | template | Destination plasmid(s) |
|---|---|---|---|
| lacZ_pET15b_fwd | TAACTAGCATAACCC CTTGGGG (SEQ ID NO: 20) | pET15b | pAT_T7_HisLacZ (SEQ ID NO: 69) |
| lacZ_pET15b_rev | CATATGGCTGCCGCG CGG (SEQ ID NO: 21) | | |
| lacZ_insert_fwd | AGCGGCCTGGTGCCG CGCGGCAGCCATATG CGTAAAATGACCATG ATTACGGATTCACT (SEQ ID NO: 22) | E. coli MG1655 genome | |
| lacZ_insert_rev | TTTAGAGGCCCCAAG GGGTTATGCTAGTTAT TTTTGACACCAGACCA ACTGGT (SEQ ID NO: 23) | | |
| lacZomega_BB_fwd | AACAGTTGCGCAGCC TGA (SEQ ID NO: 24) | pAT_T7_HisLacZ | pDM_T7_ HisLacZomega |
| lacZomega_BB_rev | CCAGTGAATCCGTAA TCATGGTCAT (SEQ ID NO: 25) | | |
| lacZomega_insert_L | ATGACCATGATTACG GATTCACTGGCCGTCG CCCGCACCGA (SEQ ID NO: 26) | lacZomega_insert_R | |
| lacZomega_insert_R | TCAGGCTGCGCAACT GTTGGGAAGGGCGAT CGGTGCGGGC (SEQ ID NO: 27) | lacZomega_insert_L | |
| lacZalpha_BB_fwd | TAGCATAACCCCTTGG GGC (SEQ ID NO: 28) | pDM_noro_A2_lacZA (SEQ ID NO: 72) | pDM_noro_A2_lacZA (SEQ ID NO: 72) |
| lacZalpha_BB_rev | GCGCAACTGTTGGGA AGG (SEQ ID NO: 29) | | |
| lacZalpha_insert_L | CGCACCGATCGCCCTT CCCAACAGTTGCGCA GCCTGAATGGCGAAT GGTAAT (SEQ ID NO: 30) | lacZalpha_insert_R | |

TABLE 3 -continued

List of PCR Primers Used for Plasmid Construction

| Primer Name | Sequence | template | Destination plasmid(s) |
| --- | --- | --- | --- |
| lacZalpha_insert_R | CCCGTTTAGAGGCCCC AAGGGGTTATGCTATT ATTACCATTCGCCATT CAGG (SEQ ID NO: 31) | lacZalpha_insert_L | |
| lacZ_BB_fwd | ATGACCATGATTACG GATTCACTGGCCGTC (SEQ ID NO: 32) | ZIKV_Sensor_27B_LacZ, pDM_noro_A2_lacZA | pDM_noro_A#_lacZ, pDM_noro_A#_lacZA, pDM_noro_S#_lacZ, pDM_noro_S#_lacZA, where # = {1, 2, 3, 4, 5, 6} |
| Dstar_lacZ_BB_rev | CCGGCTACCGTAGAA ACGCGAATTTACTAG CATAAGGGAGAGCGT CGAGATC (SEQ ID NO: 33) | | |
| Dnorm_TS_insert_fwd | CTAGTAAATTCGCGTT TCTACGGTAGCCGGG CGCTAATACGACTCA CTATAGGG (SEQ ID NO: 34) | Toehold switch DNA strands | |
| TS_insert_linker_rev | GACGGCCAGTGAATC CGTAATCATGGTCATC TTCTTGCGCTGCCGCC AGGTT (SEQ ID NO: 35) | | |

TABLE 4

List of DNA Strands Used for Toehold Switches and Sequencing

| Primer Name | Sequence | Description |
| --- | --- | --- |
| Toehold switch S1 DNA | GCGCTAATACGACTCACTATAGGGCCATC TTCATTCACAAAACTGGGAGCCAGATTGC GAGGACTTTAGAACAGAGGAGATAAAGAT GTCGCAATCTGGAACCTGGCGGCAGCGCA AGAAGATG (SEQ ID NO: 36) | Toehold switch DNA templates |
| Toehold switch S2 DNA | GCGCTAATACGACTCACTATAGGGATCGC CCTCCCACGTGCTCAGATCTGAGAATCTCA TGGACTTTAGAACAGAGGAGATAAAGATG ATGAGATTCTCAACCTGGCGGCAGCGCAA GAAGATG (SEQ ID NO: 37) | |
| Toehold switch S3 DNA | GCGCTAATACGACTCACTATAGGGACAAA ACTGGGAGCCAGATTGCGATCGCCCTCCC ACGGACTTTAGAACAGAGGAGATAAAGAT GGTGGGAGGGCGAACCTGGCGGCAGCGC AAGAAGATG (SEQ ID NO: 38) | |
| Toehold switch S4 DNA | GCGCTAATACGACTCACTATAGGGCTGGG ACGAGGTTGGCTGCGGACCCATCAGATGG GTGGACTTTAGAACAGAGGAGATAAAGAT GACCCATCTGATAACCTGGCGGCAGCGCA AGAAGATG (SEQ ID NO: 39) | |
| Toehold switch S5 DNA | GCGCTAATACGACTCACTATAGGGTCATT CGACGCCATCTTCATTCACAAAACTGGGA GGGACTTTAGAACAGAGGAGATAAAGATG CTCCCAGTTTTAACCTGGCGGCAGCGCAA GAAGATG (SEQ ID NO: 40) | |
| Toehold switch S6 DNA | GCGCTAATACGACTCACTATAGGGAGCCA GATTGCGATCGCCCTCCCACGTGCTCAGAT CGGACTTTAGAACAGAGGAGATAAAGATG GATCTGAGCACAACCTGGCGGCAGCGCAA GAAGATG (SEQ ID NO: 41) | |
| Toehold switch A1 DNA | GCGCTAATACGACTCACTATAGGGTCTGA TGGGTCCGCAGCCAACCTCGTCCCAGAGG TCGGACTTTAGAACAGAGGAGATAAAGAT GGACCTCTGGGAAACCTGGCGGCAGCGCA AGAAGATG (SEQ ID NO: 42) | |
| Toehold switch A2 DNA | GCGCTAATACGACTCACTATAGGGTGGGA GGGCGATCGCAATCTGGCTCCCAGTTTTGT GGACTTTAGAACAGAGGAGATAAAGATGA CAAAACTGGAACCTGGCGGCAGCGCAAG AAGATG (SEQ ID NO: 43) | |

TABLE 4 -continued

List of DNA Strands Used for Toehold Switches and Sequencing

| Primer Name | Sequence | Description |
| --- | --- | --- |
| Toehold switch A3 DNA | GCGCTAATACGACTCACTATAGGGTGTGA ATGAAGATGGCGTCGAATGACGCCAACCC ATGGACTTTAGAACAGAGGAGATAAAGAT GATGGGTTGGCGAACCTGGCGGCAGCGCA AGAAGATG (SEQ ID NO: 44) | |
| Toehold switch A4 DNA | GCGCTAATACGACTCACTATAGGGAGATC TGAGCACGTGGGAGGGCGATCGCAATCTG GCGGACTTTAGAACAGAGGAGATAAAGAT GGCCAGATTGCGAACCTGGCGGCAGCGCA AGAAGATG (SEQ ID NO: 45) | |
| Toehold switch A5 DNA | GCGCTAATACGACTCACTATAGGGATCGC AATCTGGCTCCCAGTTTTGTGAATGAAGAT GGGACTTTAGAACAGAGGAGATAAAGATG CATCTTCATTCAACCTGGCGGCAGCGCAA GAAGATG (SEQ ID NO: 46) | |
| Toehold switch A6 DNA | GCGCTAATACGACTCACTATAGGGTCGAA TGACGCCAACCCATCTGATGGGTCCGCAG CCGGACTTTAGAACAGAGGAGATAAAGAT GGGCTGCGGACCAACCTGGCGGCAGCGCA AGAAGATG (SEQ ID NO: 47) | |
| pCOLA_seq_fwd | CGTTACTGGTTTCACATTCACCACCC (SEQ ID NO: 48) | Sequencing primer used for confirming sequence of toehold switch sensors inserted in pCOLA, pCDF, pACYC expression vectors. |
| pET15b_seq_fwd1 | CCTGCCACCATACCCACGC (SEQ ID NO: 49) | Sequencing primer used for confirming sequence of genes inserted into pET15b vectors within the multiple cloning site region. |

Preparation of paper-based cell-free systems: Cell-free transcription-translation systems (NEB, PURExpress) were prepared for freeze-drying with the following components by volume: cell-free solution A, 40%; cell-free solution B, 30%; RNase Inhibitor (Roche, 03335402001, distributed by MilliporeSigma), 2%; chlorophenol red-b-D-galactopyranoside (Roche, 10884308001, distributed by MilliporeSigma, 24 mg/ml), 2.5%; with the remaining volume reserved for toehold switch DNA, water, and lacZω peptide added to a final concentration of 2 µM. When testing the toehold switches expressed from a plasmid, the plasmid DNA was added to the cell-free reaction mix to a final concentration of 30 ng/µL. When testing toehold switches expressed from linear DNA, the DNA was added to the cell-free reaction mix to a final concentration of 33 nM.

Filter paper (Whatman, 1442-042) for housing the cell-free reactions was first blocked with 5% bovine serum albumin (BSA) overnight. After blocking, the paper was washed three times in water for 5 to 10 minutes. The paper was then heated to 50° C. for drying and cut into 2-mm diameter paper disks using a biopsy punch. The disks were transferred into 200-µL, PCR tubes and 1.8 µL of the cell-free reaction mix was applied to each disk. PCR tubes containing the paper disks were then flash frozen in liquid nitrogen and transferred into a lyophilizer to dry overnight. Measurements were performed on the resulting paper disks two to four days after the freeze-drying process was completed. The paper disks remained active for at least a month of room-temperature storage using conditions described previously[30], with the systems stored under nitrogen, shielded from light, and in the presence of silica gel desiccation packages.

Screening of norovirus-specific toehold switches: Norovirus target RNA was produced using T7 RNA polymerase-based transcription (Epicenter, ASF3257) from linearized DNA templates. 1.8 µL of a 5 µM solution of the target RNA was applied to a paper disk containing the embedded cell-free system and DNA for the toehold switch. The progress of the cell-free reaction was then monitored in a plate reader (Biotek, H1MF) at 37° C. in triplicate. The relative absorbance of the paper-based reactions at 575 nm wavelength or OD575 was calculated by taking the absorbance at 575 nm and subtracting from it the absorbance at 575 nm measured at the start of the reaction. This relative absorbance thus removes any absorbance contribution from the paper disk and the lacZ substrate chlorophenol red-b-D-galactopyranoside. The fold change in lacZ production rate was calculated by computing the rate of change in OD575 and dividing the rate obtained for the toehold switch in the presence of the target RNA by that obtained in the absence of the target RNA. The fold change in lacZ production rate was measured after one hour of cell-free reaction for assessment of the toehold switches. The change in OD575 or ΔOD575 was calculated by taking the OD575 for the reaction with the toehold switch and the target RNA and subtracting from it the OD575 for the reaction of the toehold switch without the target RNA. ΔOD575 was computed after two hours of cell-free reaction. Errors in OD575 were determined from the standard deviation of triplicate measurements. Errors in fold change lacZ production rate and ΔOD575 were determined by adding the relative and absolute errors of OD575 in quadrature, respectively. Welch's unequal variances t-test was used to calculate p-values for plate reader detection experiments with $p<0.05$ used as the cutoff to define a statistically significant result.

Isothermal amplification of norovirus RNA: For NASBA experiments, reaction buffer (Life Sciences, NECB-24; 33.5%), nucleotide mix (Life Sciences NECN-24; 16.5%), RNase inhibitor (Roche, 03335402001; 0.5%), 12.5 mM of each DNA primer (2%), nuclease free water (2.5%), and RNA amplicon (20%) were assembled at 4° C. and incubated at 65° C. for 2 min, followed by a 10 min incubation at 41° C. Enzyme Mix (Life Sciences NEC-1-24; 25%) was then added to the reaction (for a final volume of 5 µL), and the mixture was incubated at 41° C. for 2 hr. The amplified product was then diluted 1:6 in water and applied to paper disks containing the cell-free system and DNA for the toehold switch. Sequences of the primers used for NASBA and RT-RPA are provided in Table 5.

additional 2 hours. The beads were then washed three times with PBST and suspended in 30 µL of 1× PBS (phosphate-buffered saline) to yield a final suspension of blocked magnetic beads.

A dilution series of virus particles ranging from 1:10$^3$ to 1:10$^7$ was prepared by first taking a 1-µL aliquot of a norovirus GII.4 Sydney positive stool sample and diluting it into 1 mL of PBS. The resulting 1:10$^3$ sample was serially diluted by factors of ten into PBS to generate the rest of the dilution series. Biotin-labelled synbody ASU1052 (described in Gupta et al., (2017) *Anal. Chem.* 89:7174-7181, which is incorporated herein by reference) was then added to a concentration of 1 µM into each diluted sample and incubated with shaking for 1 hour at room temperature. The

| Norovirus isothermal amplification primers | | | |
|---|---|---|---|
| Norovirus Genotype | Toehold Switch | Forward Primer | Reverse Primer |
| GI1.4 | S1 | AATTCTAATACGACTCACTATAG GGAGAAGGATTCTCAGATCTGAG CACGTGGGA (SEQ ID NO: 50) | ATTGTTGACCTCTGGGACGA (SEQ ID NO: 51) |
|  | S2 | AATTCTAATACGACTCACTATAG GGAGAAGGCAGGCAAGAGCCAA TGTTCAGA (SEQ ID NO: 52) | CTCATTGTTGACCTCTGGGA (SEQ ID NO: 53) |
|  | S6 | AATTCTAATACGACTCACTATAG GGAGAAGGGCAAGAGCCAATGTT CAGATGGA (SEQ ID NO: 54) | CTCATTGTTGACCTCTGGGA (SEQ ID NO: 55) |
|  | A1 | AATTCTAATACGACTCACTATAG GGAGAAGGGCTCCAAAGCCATAA CCTCA (SEQ ID NO: 56) | GCAAGAGCCAATGTTCAGATGG A (SEQ ID NO: 57) |
|  | A2 | AATTCTAATACGACTCACTATAG GGAGAAGGCTCATTGTTGACCTC TGGGA (SEQ ID NO: 58) | GATGGATGAGATTCTCAGATCT GA (SEQ ID NO: 59) |
|  | A4 | AATTCTAATACGACTCACTATAG GGAGAAGGCTCATTGTTGACCTC TGGGA (SEQ ID NO: 60) | CAAGAGCCAATGTTCAGATGGA (SEQ ID NO: 61) |
| GII.6 | S2 | AATTCTAATACGACTCACTATAG GGAGAAGGCAGACAAGAGGCCA TGTTCA (SEQ ID NO: 62) | TCATTGTTGGCCTCTGGTACGA (SEQ ID NO: 63) |

RT-RPA experiments used the commercial TwistAmp Basic RT kit (TwistDx). Reactions were prepared by combining 10 µM forward primer (4.8%), 10 µM reverse primer (4.8%), rehydration buffer, RNase Inhibitor (Roche, 03335402001; 4.4%), and RNA amplicon (22%) at room temperature and transferring the mixture to the freeze-dried reaction pellet. After mixing, 2.5 µL of 280 mM magnesium acetate (5%) was added to start the reaction and it was incubated at 41° C. for 5-7 minutes. The reaction tube was then inverted vigorously 8-10 times, spun down briefly, and returned to incubation at 41° C. for 2 hours. The amplified product was then diluted 1:6 in water and applied to paper disks containing the cell-free system and DNA for the toehold switch.

For determination of assay detection limits, NASBA and RPA reactions were run in triplicate for each concentration of the target RNA or virus and applied to the paper-based toehold switch reactions as described above.

Synbody-based virus enrichment: A 30-µL volume of MyOne Streptavidin C1 streptavidin-coated magnetic beads (Life Technologies, U.S.A.), corresponding to 2.1×10$^8$ to 3.6×10$^8$ total beads, was added to Protein LowBind tubes (Eppendorf, U.S.A.). The bead storage solution was removed and the beads were washed three times with 1 mL of PBST (0.05% Tween 20 in 1× phosphate-buffered saline). The beads were then blocked with 3% BSA in PBST overnight at 4° C. The following day, the beads were suspended in fresh 3% BSA in PBST and blocked for an solutions were then added to the blocked streptavidin-coated magnetic beads and shaken for an additional 15 minutes at room temperature. The beads were washed three times with PBST and one time with PBS and then suspended with 50 µL water. The beads were incubated for 2 min at 95° C. to release the viral RNA for analysis. 50 µL of each stool dilution was also incubated for 2 minutes at 95° C. and used for comparison.

For cross-reactivity testing and tests of the assay against the GII.6 genotype, 1 µL of GII.4, GII.6, and GI.6 positive stool samples, as well as a norovirus-negative stool sample, were diluted into 1 ml of PBS and followed by the synbody enrichment procedure described above.

Results and Discussion

Design of Toehold Switches for Norovirus GII Detection

We first identified conserved sequence regions of the norovirus GII genome suitable for isothermal amplification and toehold-switch-based detection. Over 400 norovirus GII complete and partial genome sequences were downloaded from the NCBI database and aligned. A 200-nt target sequence that was highly conserved across the norovirus GII genomes was identified for subsequent amplification and detection experiments. This conserved sequence ran from the C-terminal region of the viral RNA-dependent RNA polymerase through to the N-terminal region of VP1, the major capsid protein.

Toehold switches for detection of the target sequence were then generated based on an updated design first applied to the detection of the Zika virus. The updated toehold switch design provided lower leakage compared to earlier toehold switches and was originally developed for evaluating AND logic expressions in E. coli. As illustrated in FIG. 2A, binding of a cognate target RNA to the updated toehold switch unwinds the lower half of the switch RNA hairpin and leaves the conserved upper stem-loop intact. This upper stem-loop is sufficiently weak to expose the ribosomal binding site (RBS) to enable translation to occur. Unlike earlier toehold switch mRNA sensors, the updated systems do not employ an RNA refolding domain downstream of the start codon, which could hamper translation of the output gene.

Based on the modified operating mechanism of the toehold switches, we implemented an updated design selection algorithm to identify the toehold switches most likely to be effective at detecting the target RNA. This algorithm modelled the interaction of a series of toehold switches designed to bind along the target RNA in 1-nt increments using the NUPACK software package. Ensemble defect levels and the affinity of the toehold switch for the target RNA were used to select designs most likely to perform well. Since the target RNA can be transcribed in either the sense or antisense direction following amplification, the top six toehold switches for the sense and antisense target RNAs were selected for experimental testing (see Table 1).

Faster RNA Detection with Toehold Switches Using α-Complementation of lacZ

In previous work using paper-based cell-free systems, the lacZ enzyme has been used as the output gene for the toehold switch to produce a visible test result through cleavage of a chromogenic substrate. LacZ, however, at 3.1 kb in length is a relatively long reporter gene compared to alternatives such as GFP (0.75 kb) and mCherry (0.72 kb), which leads to several drawbacks. In particular, the longer length of lacZ means that a greater fraction of the cell-free system resources is consumed during transcription and translation, which weakens the output from the assay, and longer times are required for the protein to be synthesized and fold, which increases the time required for the test.

In response to the above limitations, we investigated using α-complementation of lacZ to decrease assay times and strengthen output from the cell-free transcription-translation reactions. Alpha-complementation is a widely applied technique often used for screening cloning vectors. It works by dividing the lacZ enzyme into two peptides termed α and ω (FIG. 2B). The lacZ α-peptide (lacZα) consists of the first 50 to 59 residues from the N terminus of lacZ and the ω-peptide (lacZω) comprises the remaining ~970 lacZ residues. The complete lacZ must form a tetramer before it becomes catalytically active; however, lacZω cannot form a tetramer on its own as it lacks residues critical for assembly. As a result, both lacZα and lacZω must be expressed before complementation occurs and an active lacZ tetramer can assemble.

We thus implemented toehold switches that used lacZα as the output protein and added the much larger lacZω peptide as a pre-synthesized component to the paper-based cell-free reactions. Since lacZα is encoded in 180 bp, which is only ~6% of the length of the full lacZ gene, transcription and translation of each lacZα molecule should occur faster compared to lacZ and could in principle impose a substantially smaller burden on the cell-free system for each active lacZ tetramer formed. DNA encoding the norovirus-specific toehold switches was cloned into vectors upstream of the lacZα open reading frame. Following sequence confirmation, the resulting plasmids were tested in paper-based cell-free reactions supplemented with lacZω, and cleavage of the chromogenic substrate chlorophenol red-b-D-galactopyranoside was monitored using a plate reader. FIGS. 2C-2F shows the results of these experiments with six toehold switches named S1, S2, etc., for the sense orientation of the target RNA and six toehold switches named A1, A2, etc., for the antisense target orientation. All of the toehold switches were tested in parallel with reactions in which no target RNA was present. These experiments were then used to determine the fold change in the lacZ production rate and the ΔOD575 for each sensor. Three of the sense toehold switches provided ON/OFF ratios of approximately three or more (FIG. 2C) and displayed a change in absorbance at 575 nm (ΔOD575) of at least 0.4 (FIG. 2D), which can be discerned by eye. The toehold switches for the antisense target provided better performance overall with ON/OFF ratios up to 12.6-fold for A1 (FIG. 2E) and ΔOD575 up to 0.92 for A2 (FIG. 2F). Although the in silico selection algorithm successfully generated functional toehold switches for the two norovirus targets, we only detected appreciable correlations between the scoring function and the toehold switches for the antisense target. The sense target devices showed no correlations with the scoring function. Analysis of the experimental data indicate that other combinations of ensemble defect parameters coupled with different weighting factors can provide more accurate predictions of device performance (see FIGS. 7A-7L).

Figure 8:
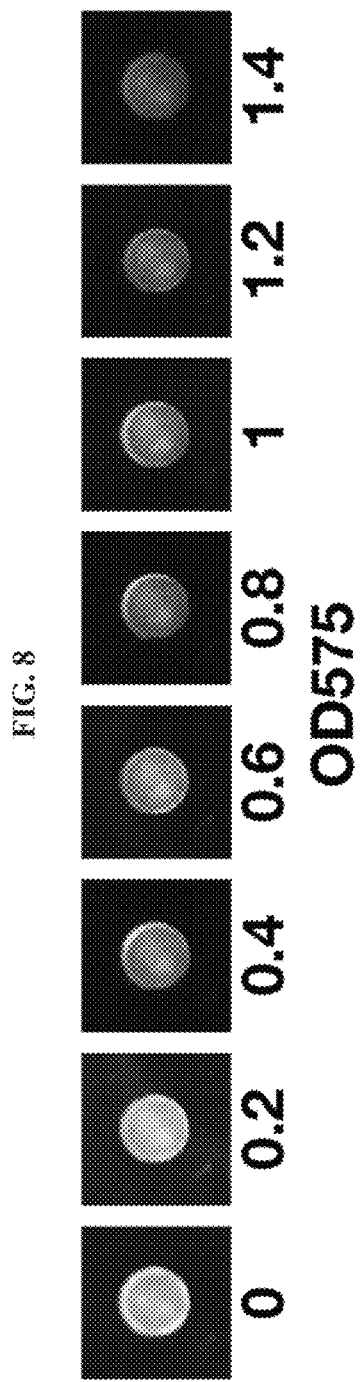
FIG. 8 is a series of photographs of paper-based toehold switch reactions using lacZ as the output protein. The colorimetric test results can be easily seen by eye with OD575 down to at least 0.4.
Figures 9A, 9B, 9C, 9D:
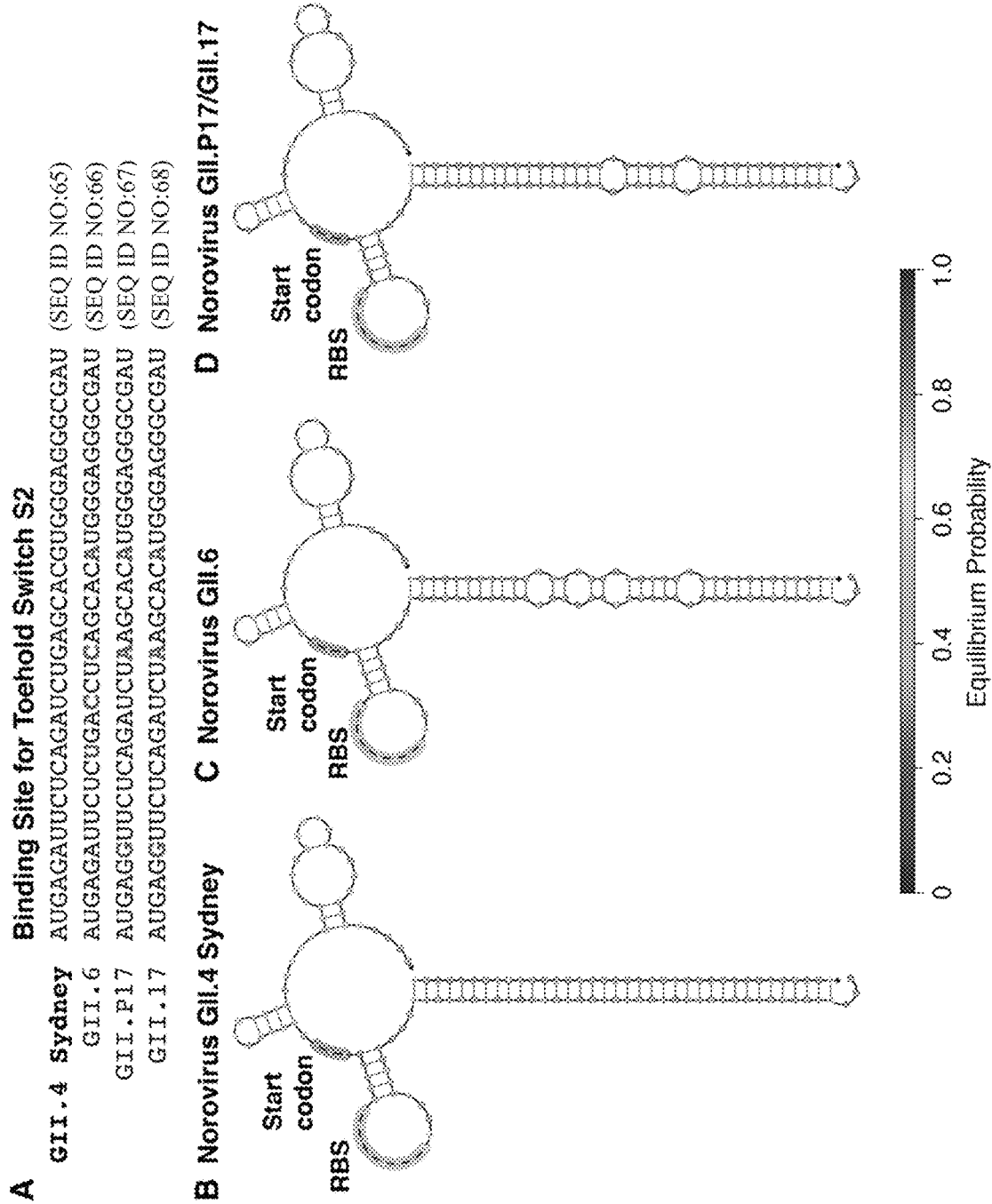
FIGS. 9A-9D present a comparison of toehold switch interactions with different norovirus GII genotypes. (A) Sequence alignment for strains GII.4 Sydney, GII.6, GII.P17, and GII.17 within the target binding region of the toehold switch. Three or four mutations are present within the 36-nt target domain. Binding sites for GII.P17 and GII.17 are identical. (B-D) Predicted secondary structures of target-switch complexes formed between toehold switch S2 and the three unique target RNAs: GII.4 Sydney (B), GII.6 (C), and GII.P17/GII.17 (D). All targets provide strong binding to the toehold switch. The active sensor region of the switch RNA has the same secondary structure across all three targets, which suggests that translational efficiency will be sufficient to report on target binding.
Figure 10:
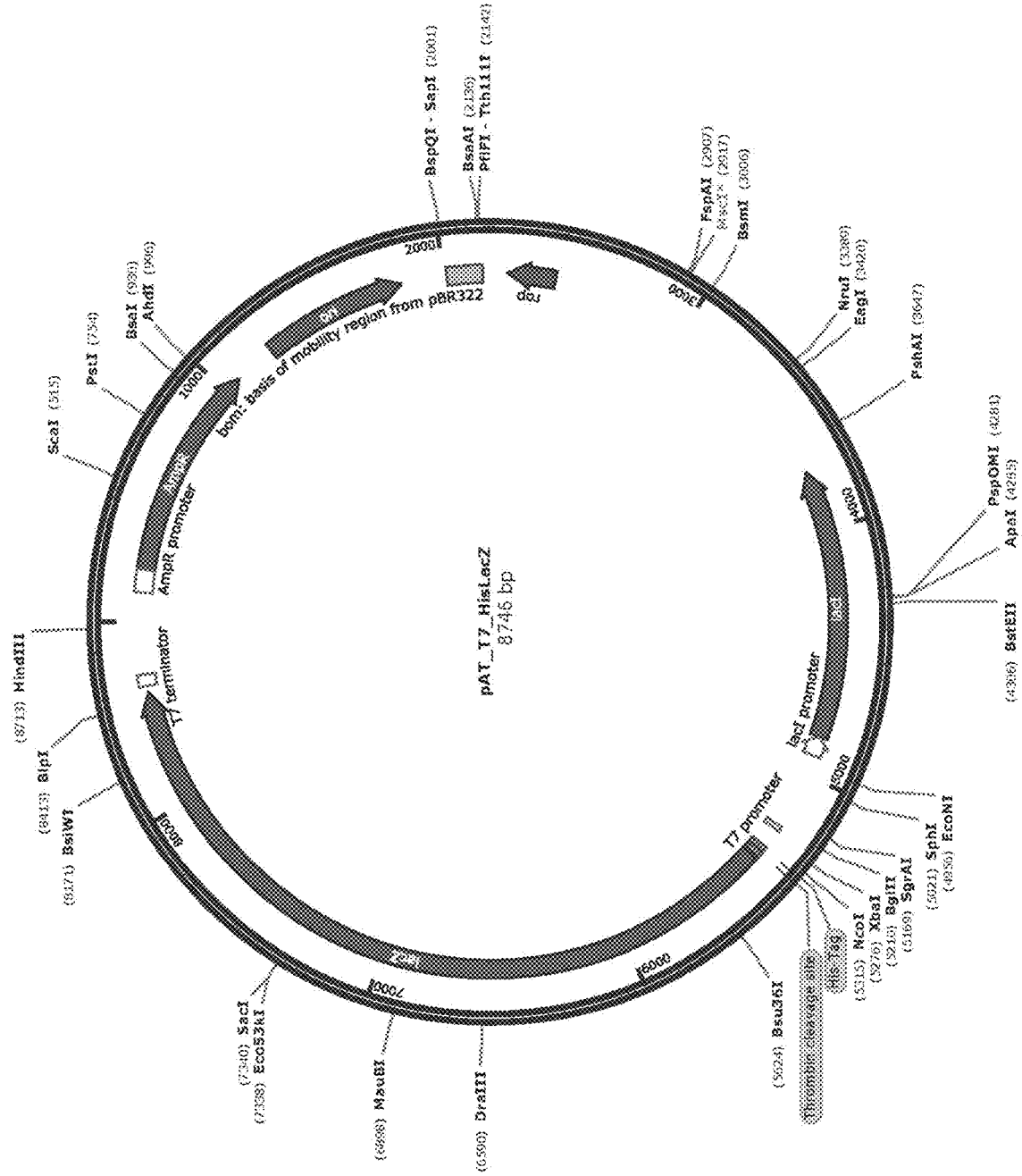
FIG. 10 is a map of plasmid pAT_T7_HisLacZ (SEQ ID NO:69).
Figure 11:
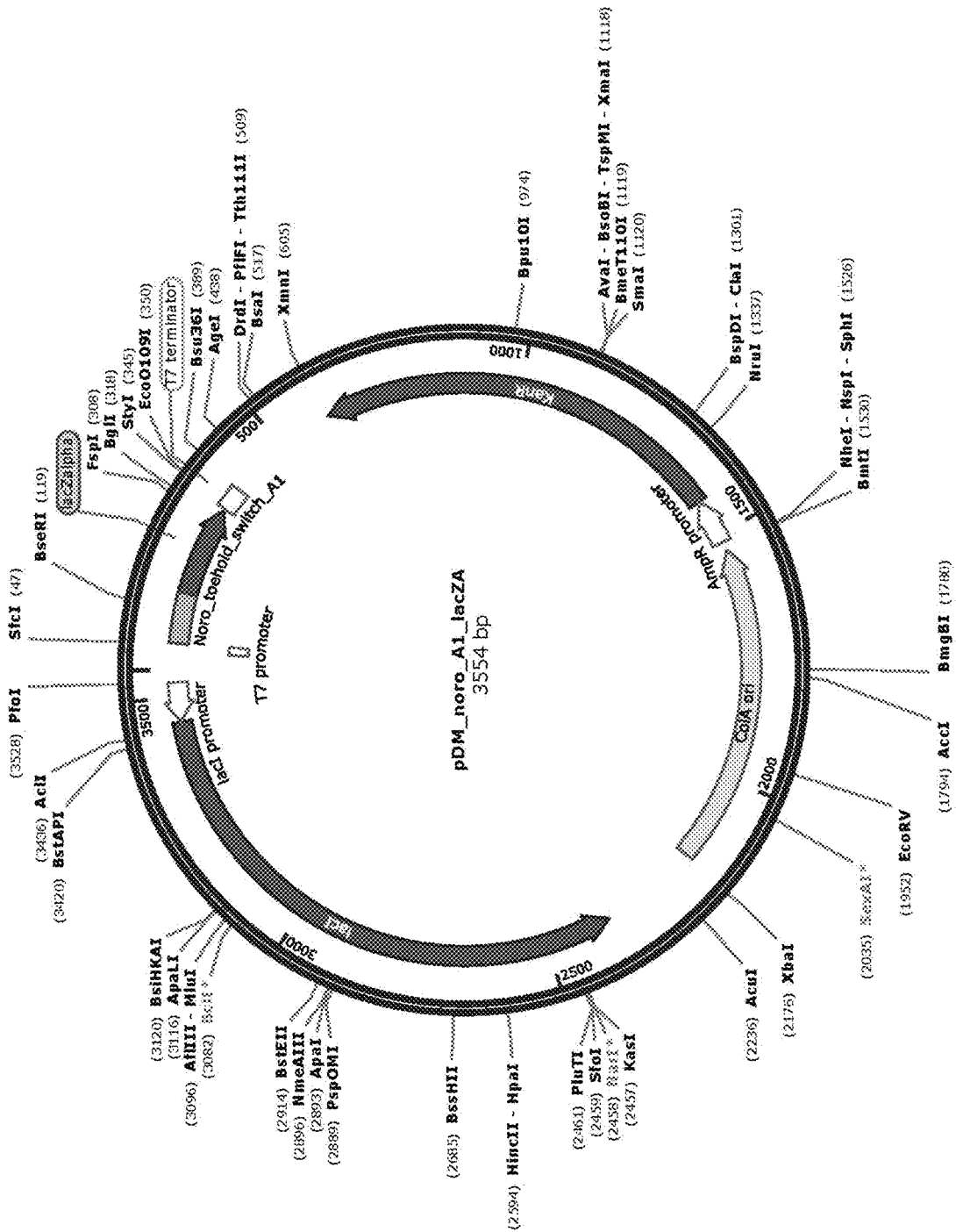
FIG. 11 is a map of plasmid pDM_noro_A1_lacZA (SEQ ID NO:70).
Figure 12:
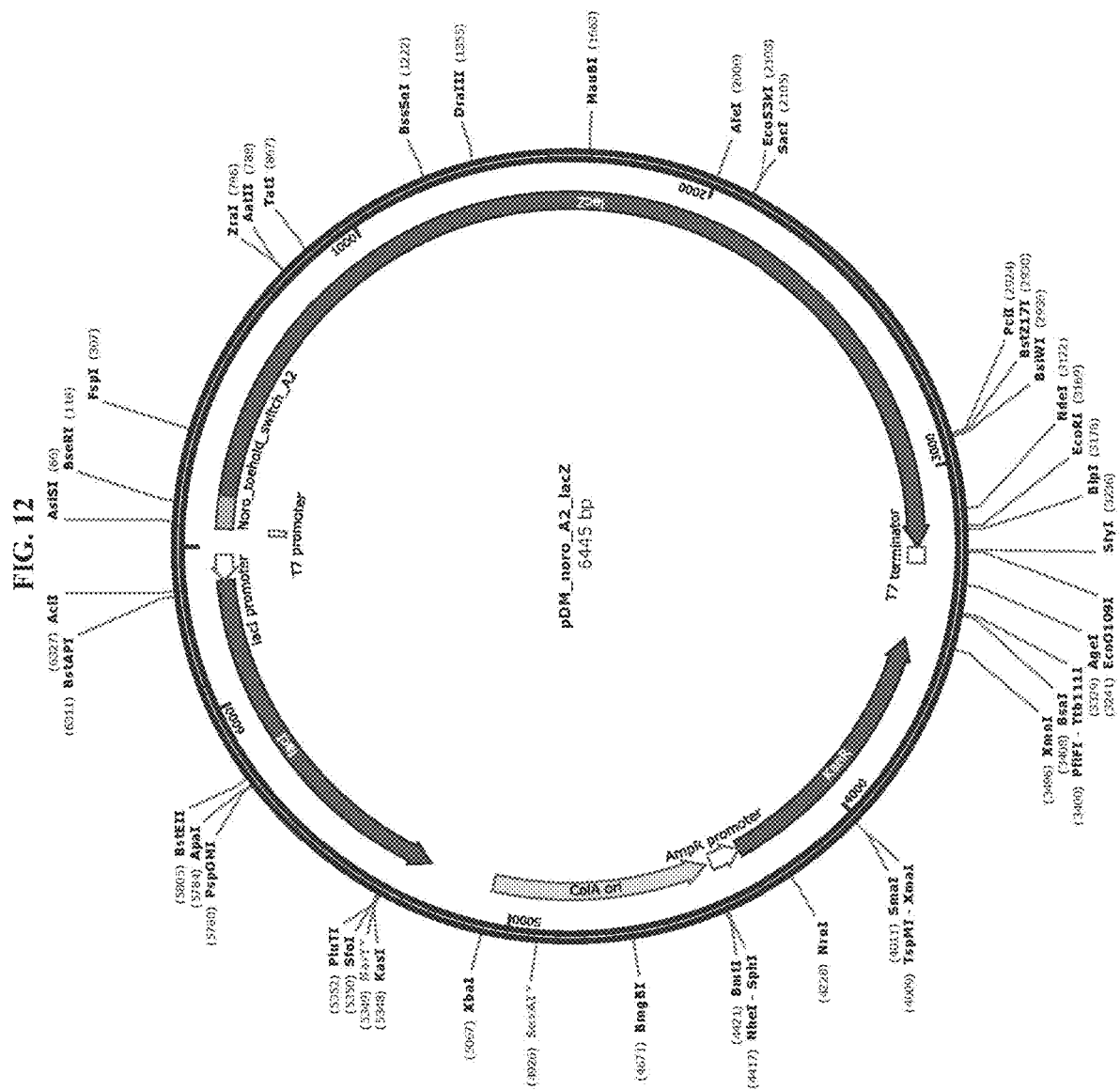
FIG. 12 is a map of plasmid pDM_noro_A2_lacZ (SEQ ID NO:71).
Figure 13:
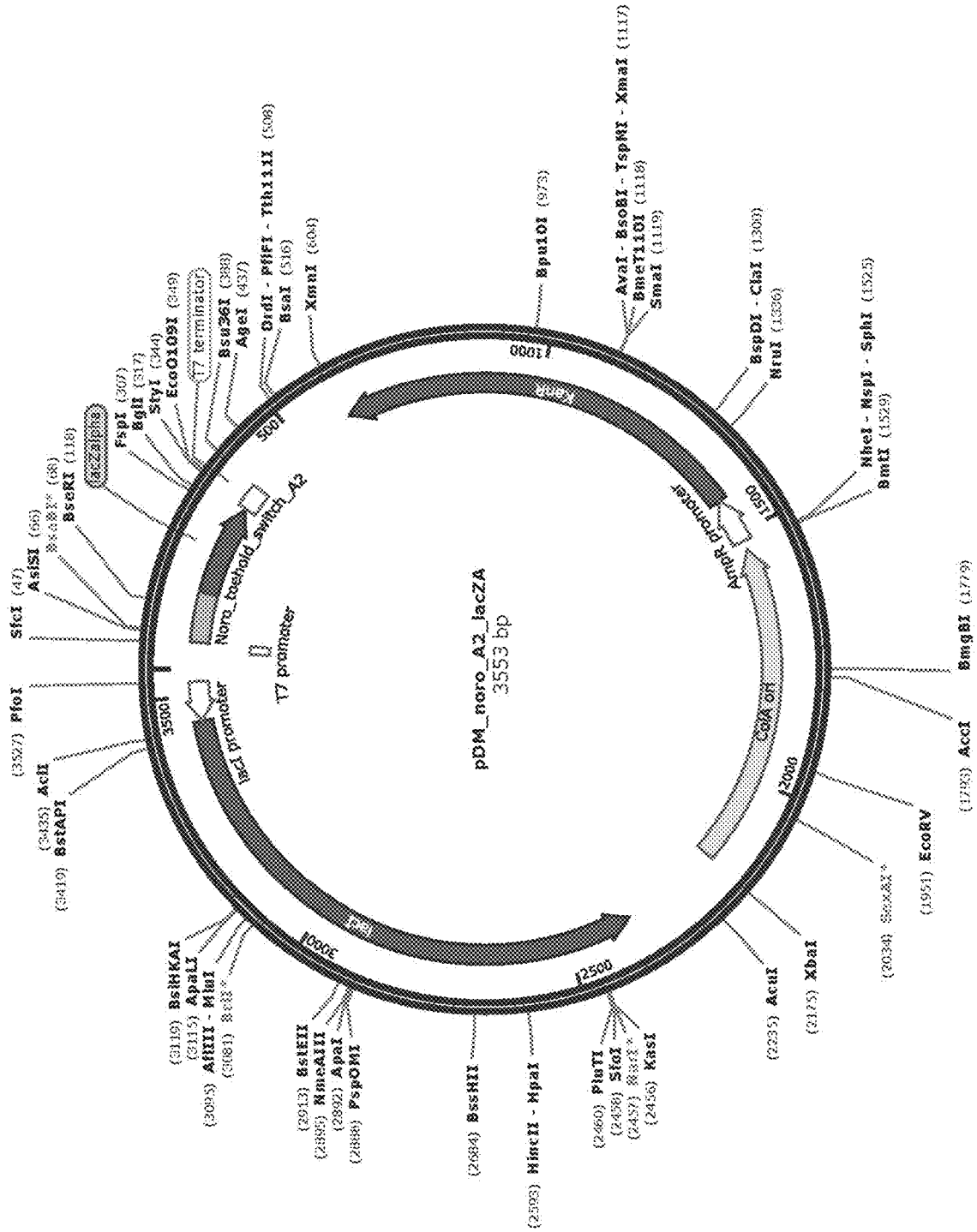
FIG. 13 is a map of plasmid pDM_noro_A2_lacZA (SEQ ID NO:72).
Figure 14:
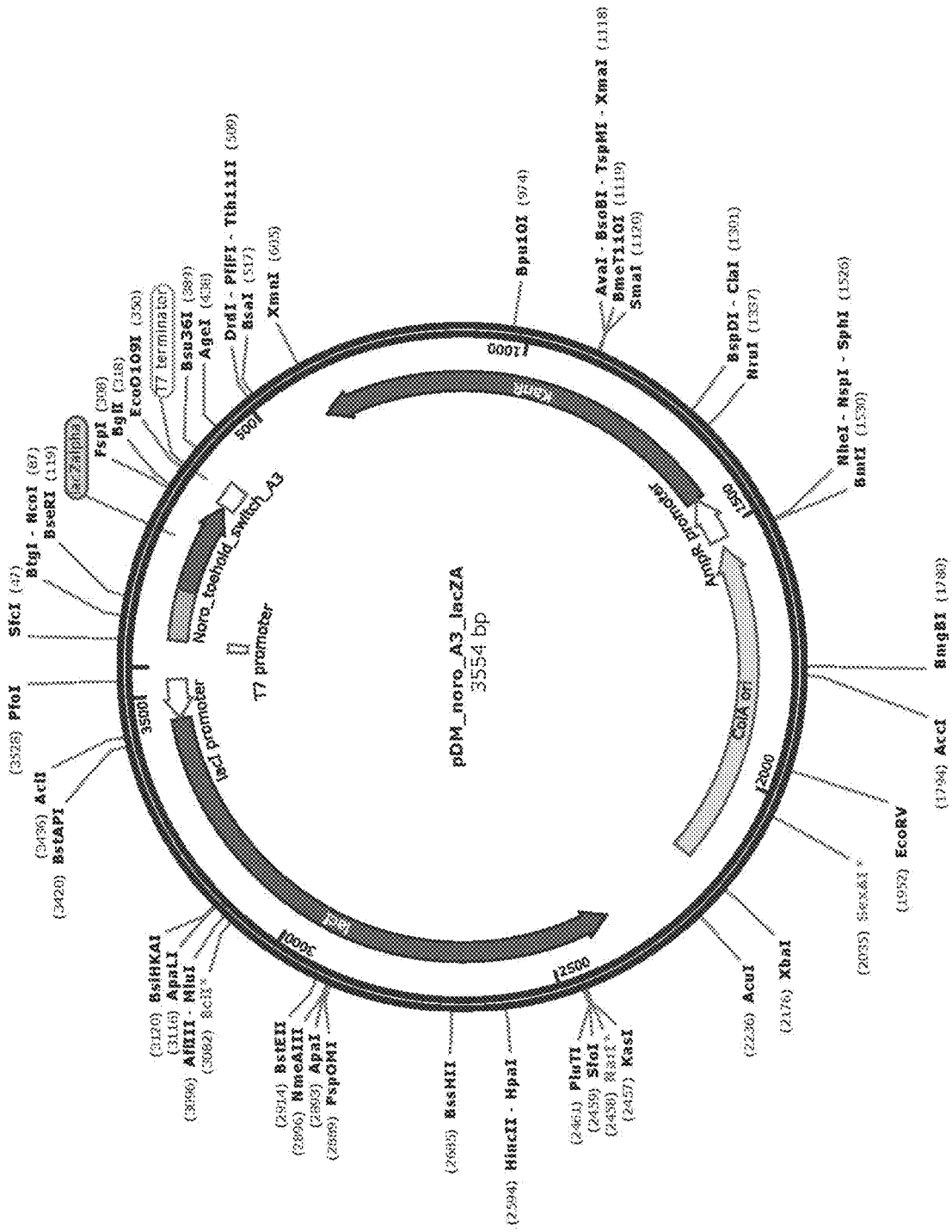
FIG. 14 is a map of plasmid pDM_noro_A3_lacZA (SEQ ID NO:73).
Figure 15:
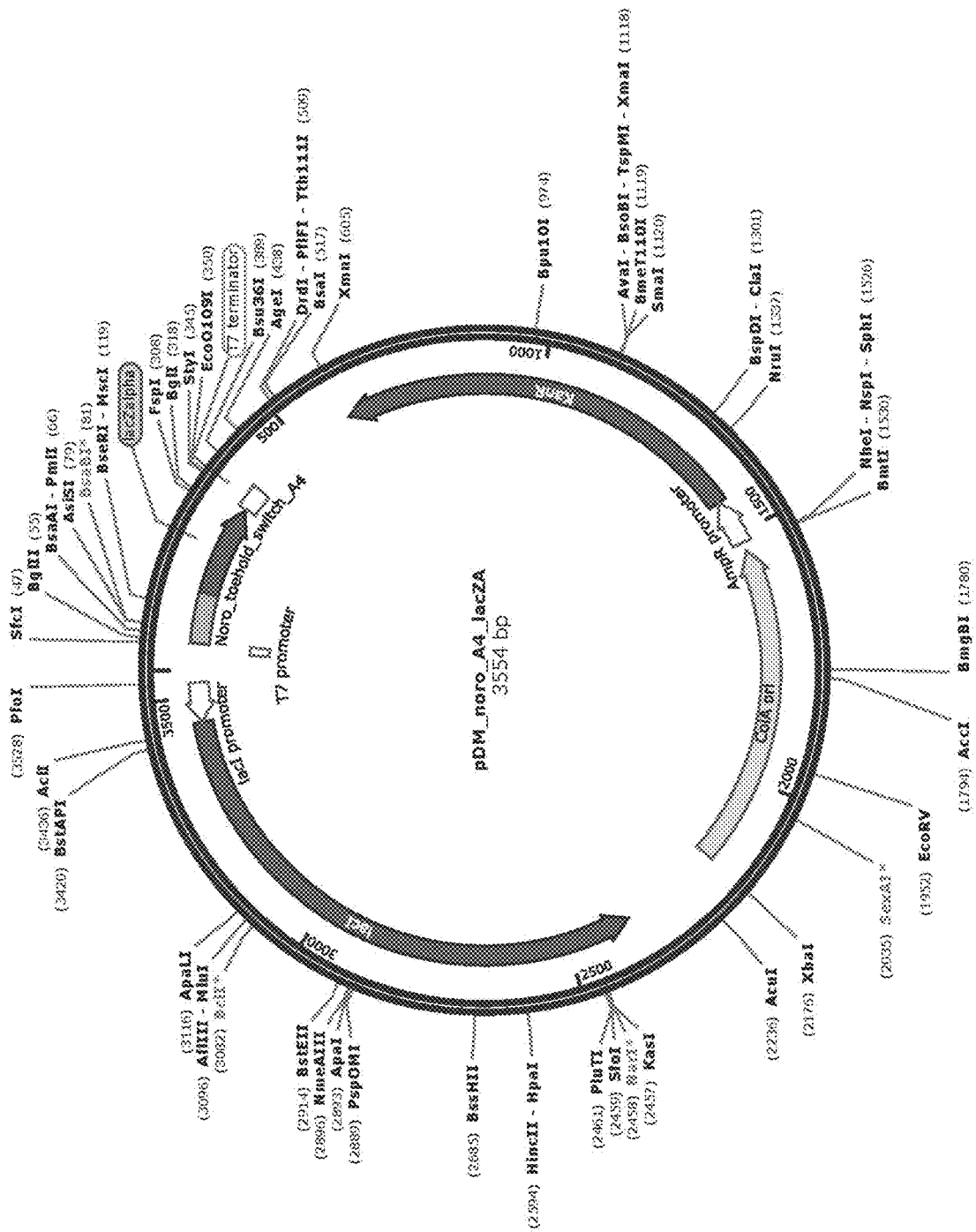
FIG. 15 is a map of plasmid pDM_noro_A4_lacZA (SEQ ID NO:74).
Figure 16:
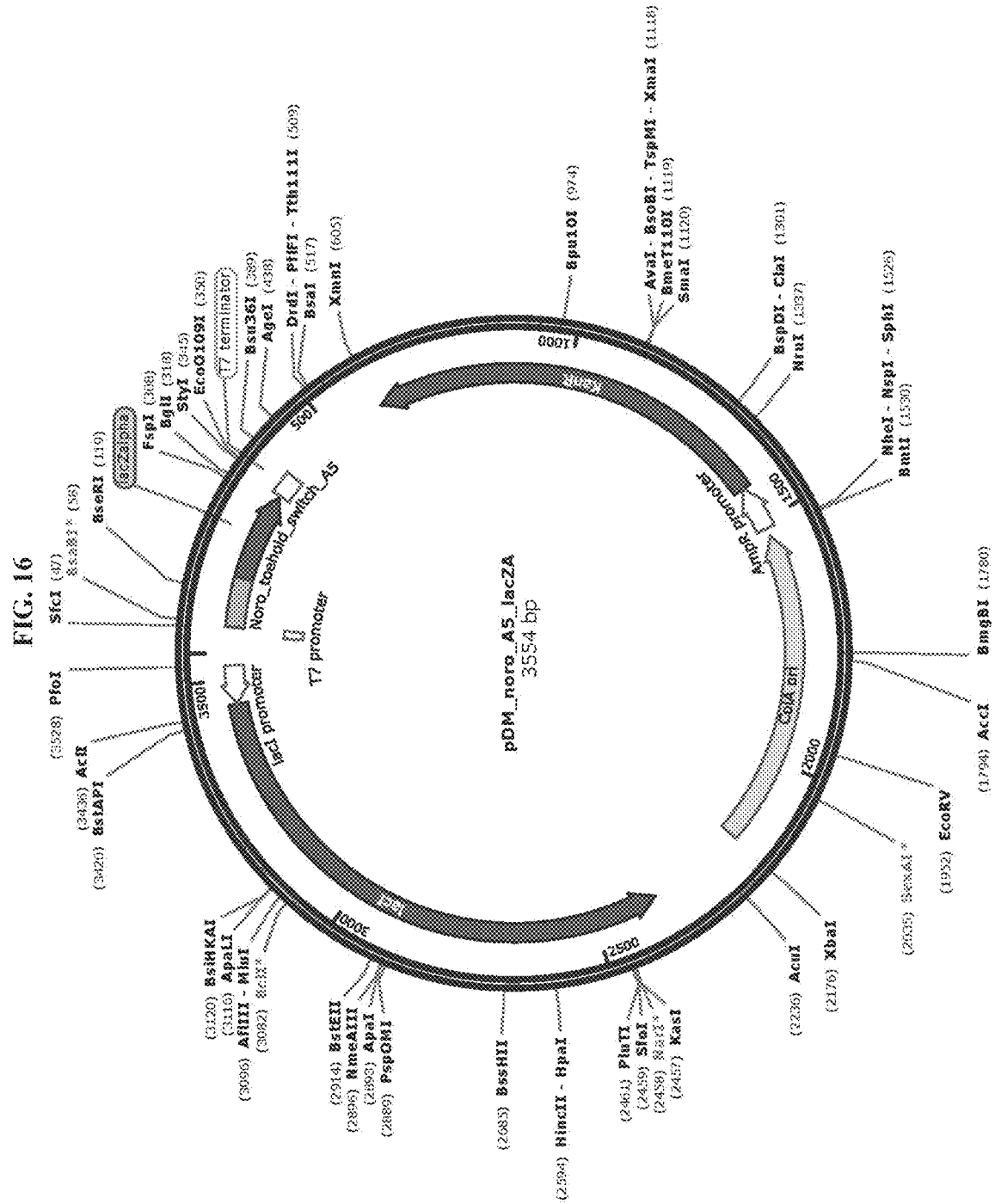
FIG. 16 is a map of plasmid pDM_noro_A5_lacZA (SEQ ID NO:75).
Figure 17:
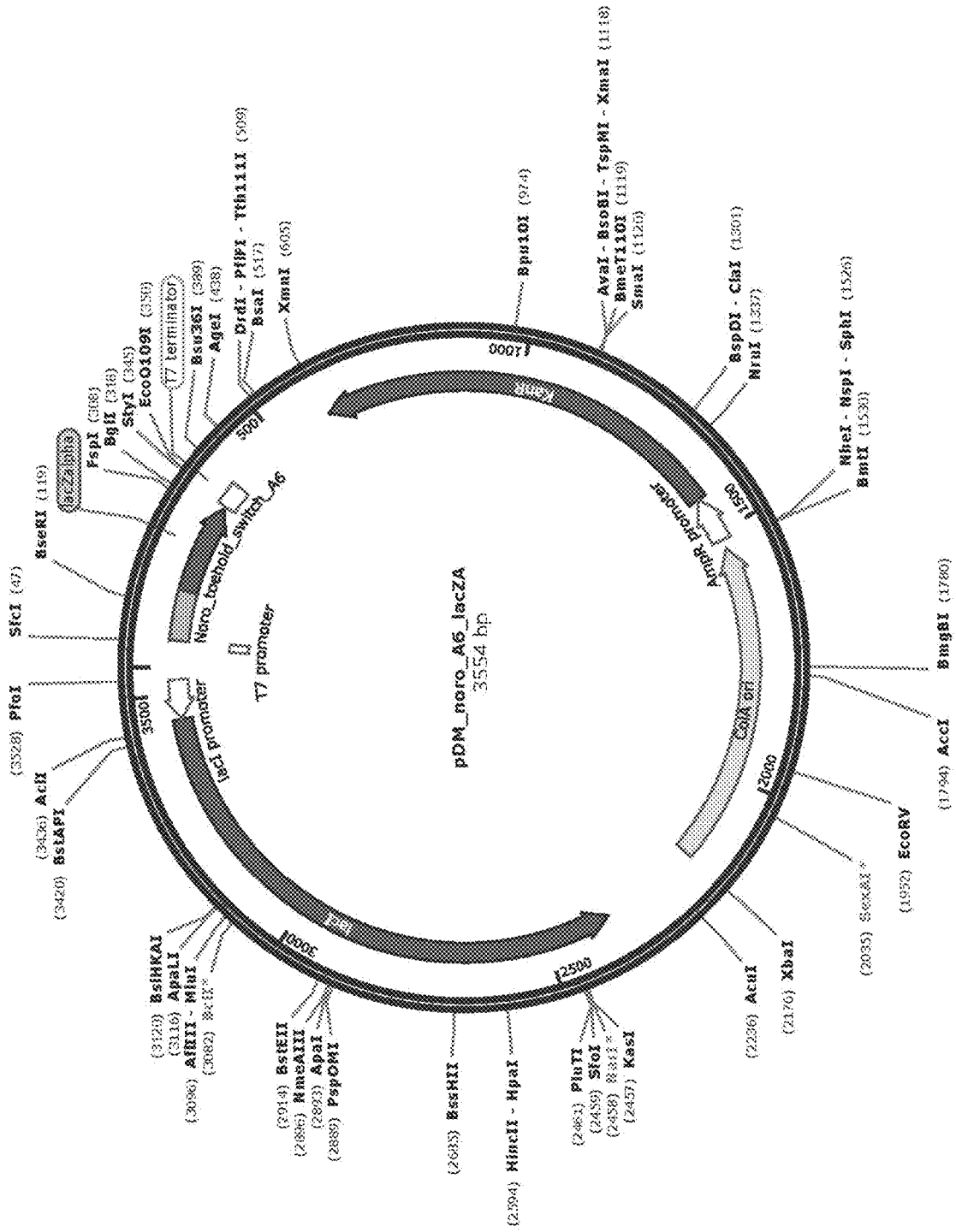
FIG. 17 is a map of plasmid pDM_noro_A6_lacZA (SEQ ID NO:76).
Figure 18:
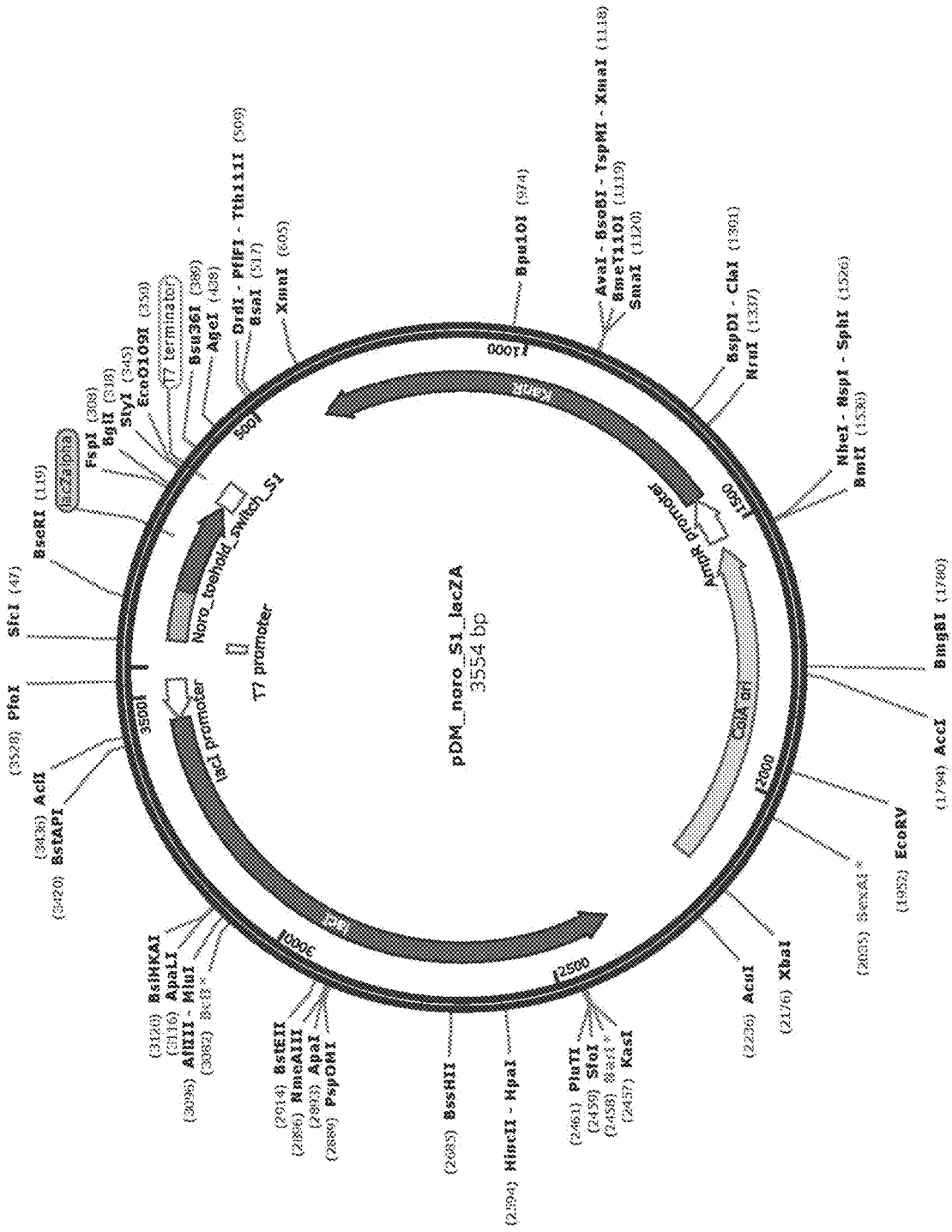
FIG. 18 is a map of plasmid pDM_noro_S1_lacZA (SEQ ID NO:77).
Figure 19:
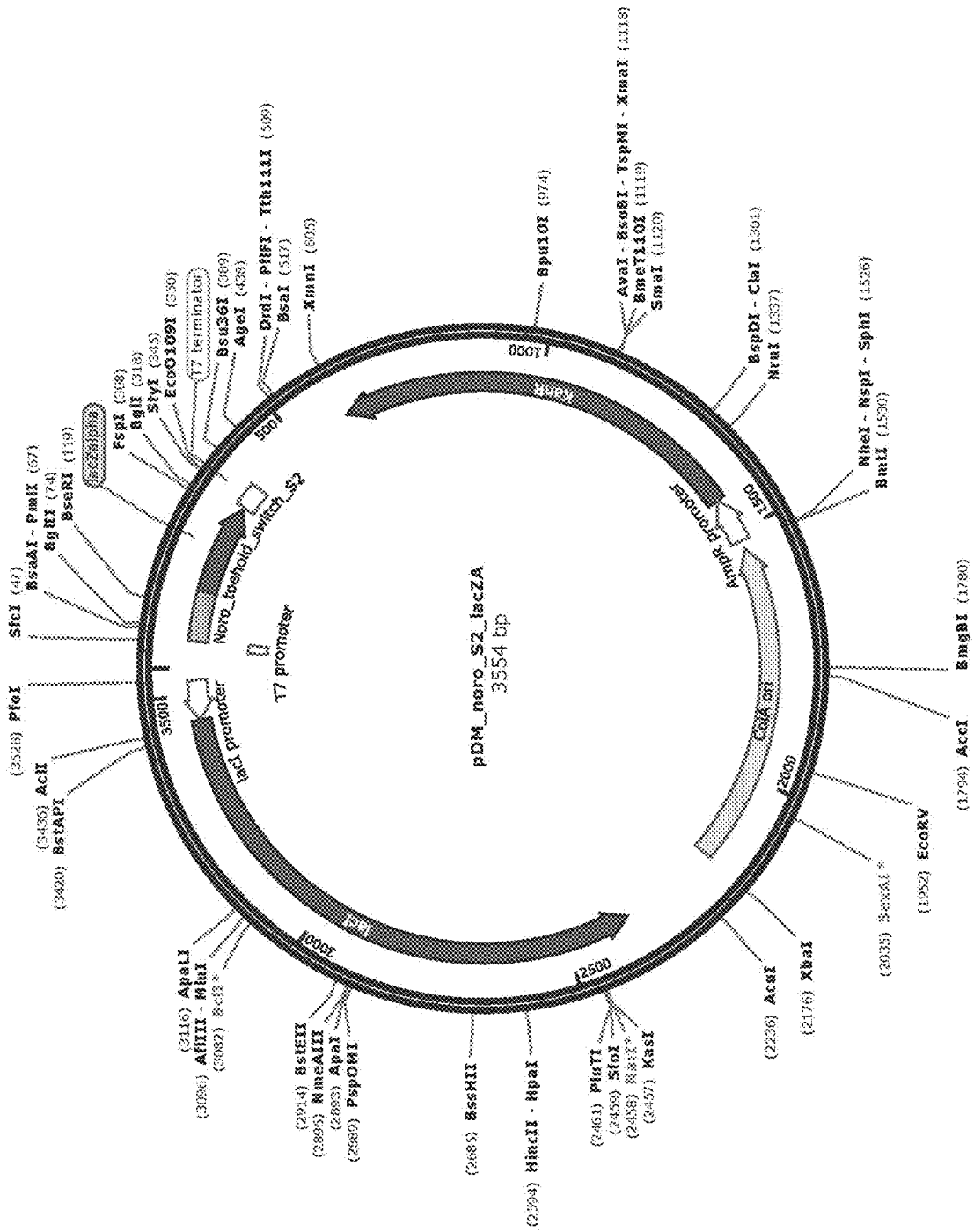
FIG. 19 is a map of plasmid pDM_noro_S2_lacZA (SEQ ID NO:78).
Figure 20:
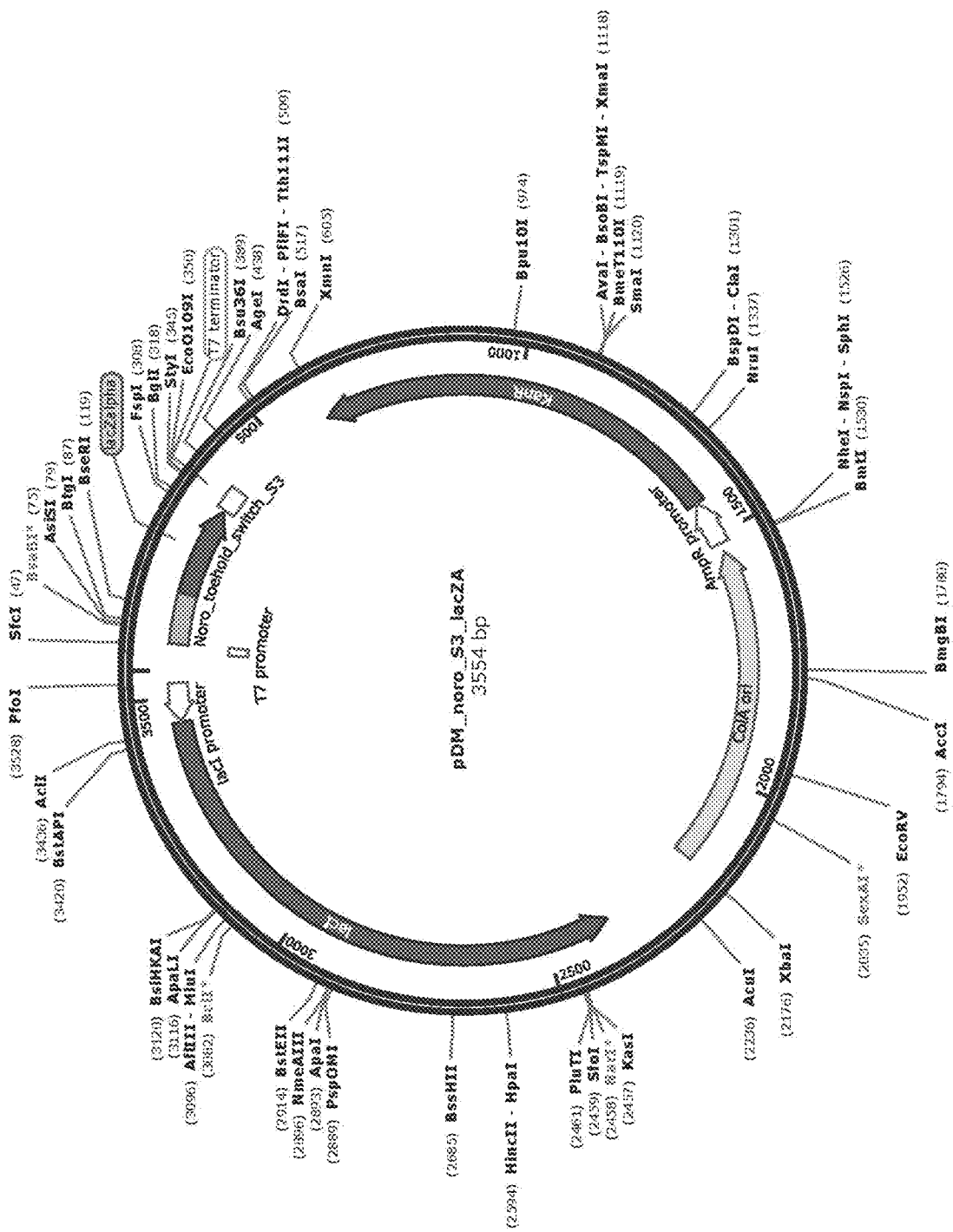
FIG. 20 is a map of plasmid pDM_noro_S3_lacZA (SEQ ID NO:79).
Figure 21:
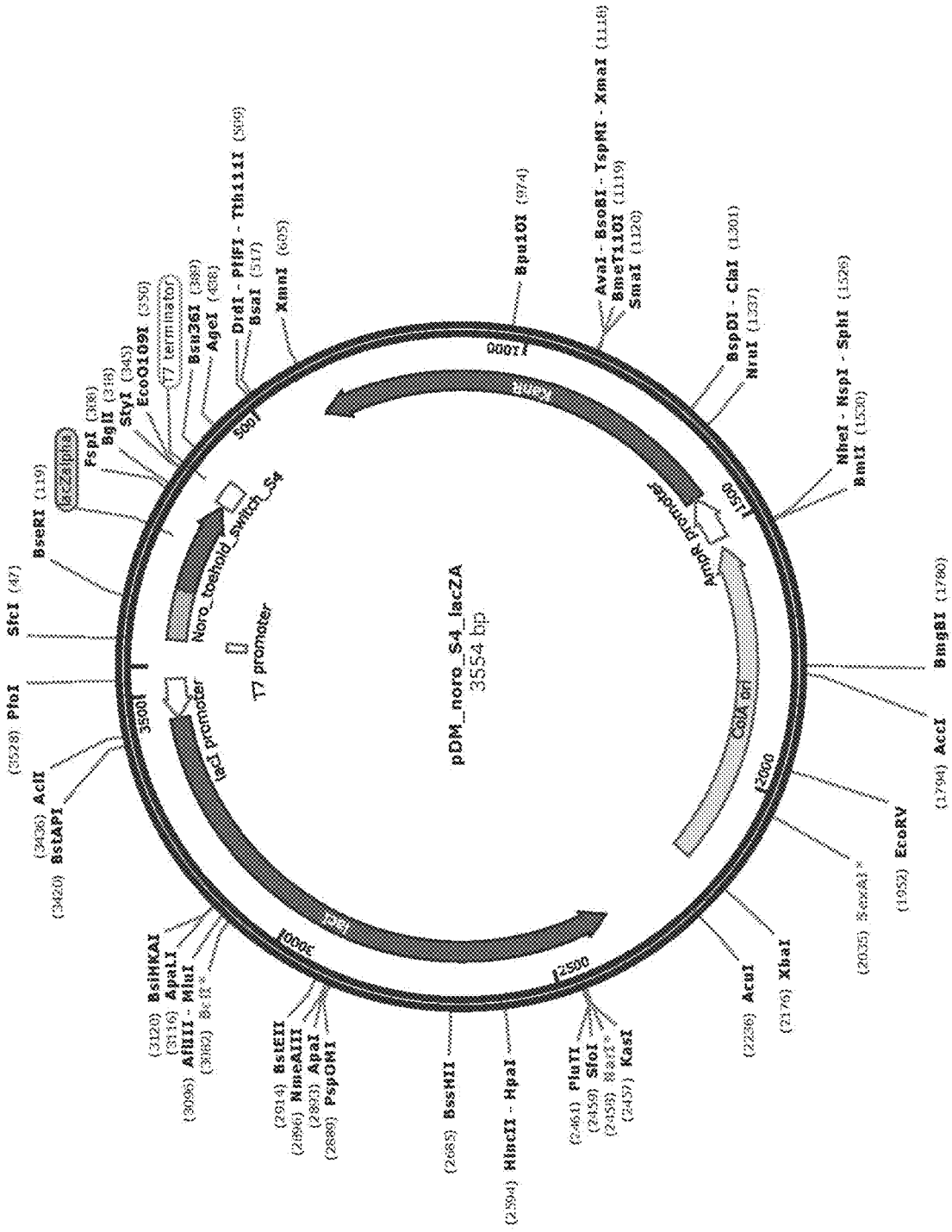
FIG. 21 is a map of plasmid pDM_noro_S4_lacZA (SEQ ID NO:80).
Figure 22:
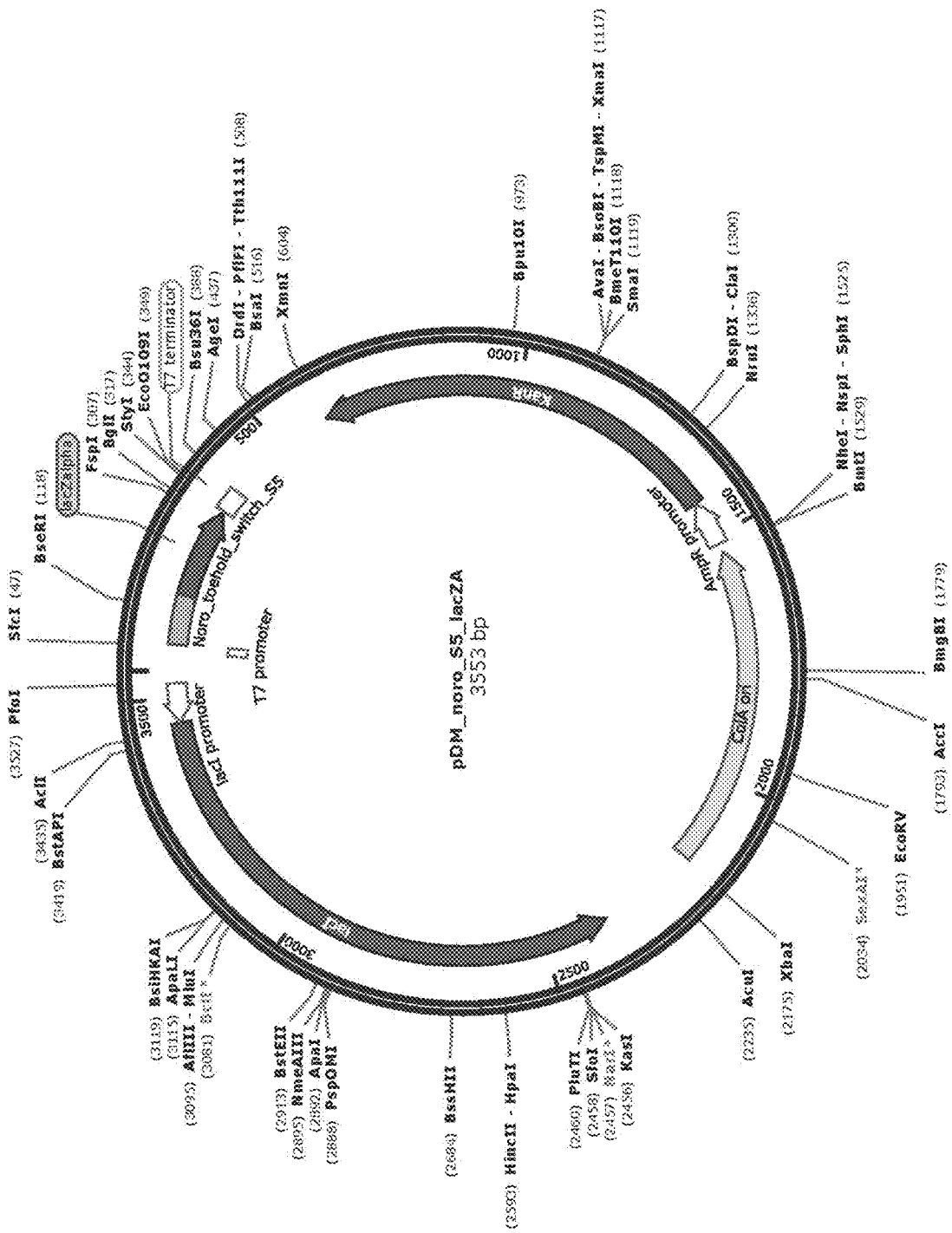
FIG. 22 is a map of plasmid pDM_noro_S5_lacZA (SEQ ID NO:81).
Figure 23:
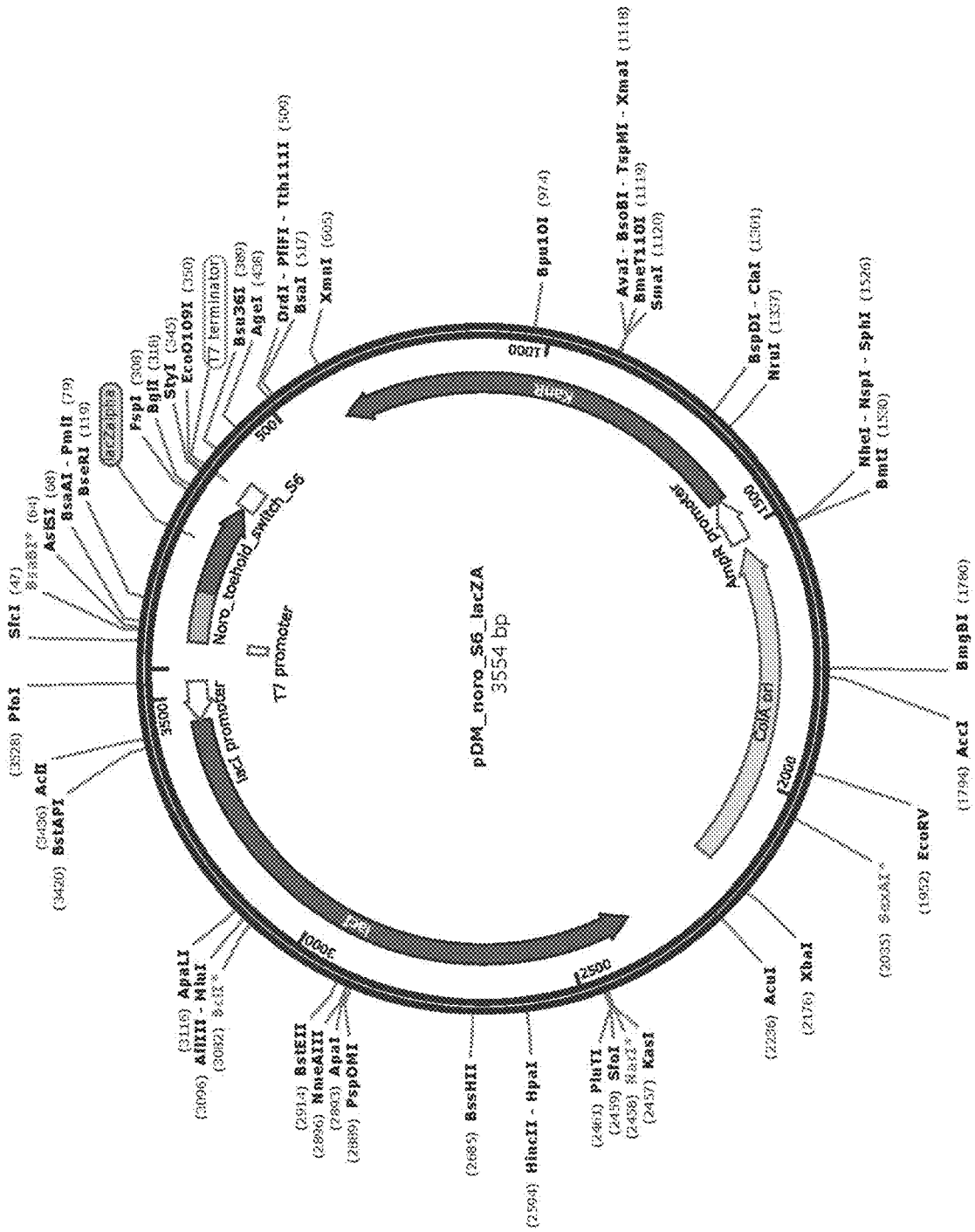
FIG. 23 is a map of plasmid pDM_noro_S6_lacZA (SEQ ID NO:82).
Figure 24:
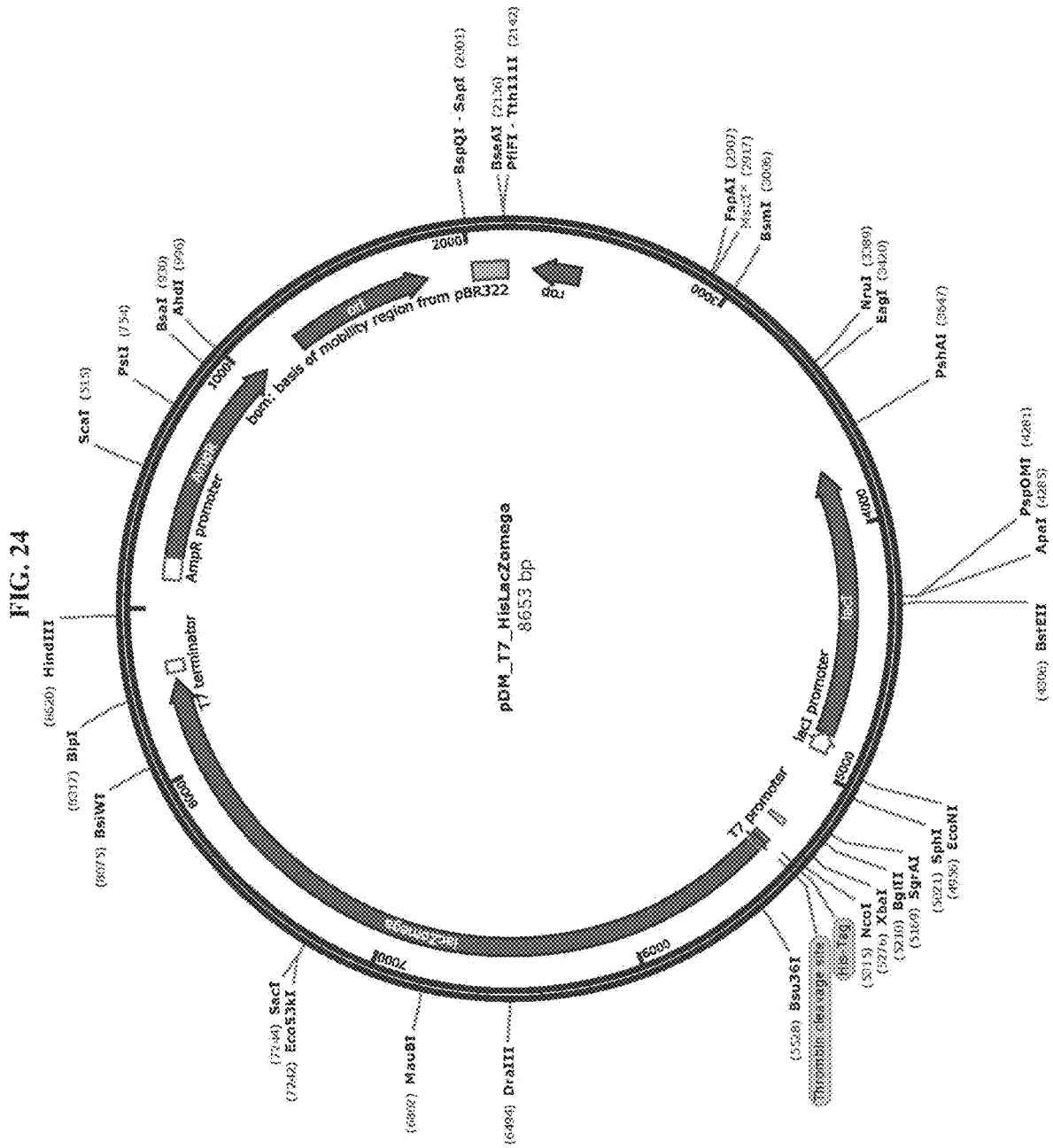
FIG. 24 is a map of plasmid pDM_T7_HisLacZomega.

To determine the effect of a-complementation on detection speed, we took one of the better performing toehold switches, A2, and inserted it into a plasmid upstream of the full lacZ open reading frame. PCR was then used to amplify linear DNA fragments from both lacZα and full-length lacZ plasmids and equal concentrations of the two DNA products were tested in paper-based cell-free reactions in the presence of the norovirus target RNA. We observed a substantial increase in the speed of the colorimetric reaction for the lacZα systems compared to full-length lacZ (FIG. 2G). Applying OD575=0.4 as the detection threshold, the lacZα reporter reached a positive result in 33 minutes compared to 56 minutes for the complete lacZ, which corresponds to a 40% reduction in detection time (see FIG. 8 for photographs of the paper-based reactions at different OD575 values). Since both reactions reach saturation and completely cleave the substrate within the two-hour measurement shown in FIG. 2G, we attribute the increased speed of the reaction in these conditions to the faster folding time of lacZα compared to lacZ, rather than to any decrease in the burden on the cell-free reaction caused by the shorter reporter protein.

Isothermal Amplification Using NASBA and RT-RPA

Since the concentrations of norovirus in stool samples from symptomatic patients range from ~30 attomoles/liter (aM) to ~3 picomoles/liter (pM), the toehold switches cannot be efficiently activated by viral nucleic acids without an amplification step. We investigated the NASBA and RT-RPA isothermal amplification techniques to determine which provided the lowest limit of detection against the norovirus GII target RNA. The six toehold switches providing the highest ON/OFF ratios were selected for testing with amplified RNA. Since each sensor targeted different regions within the conserved target sequence, we evaluated different amplification primers for each sensor. One primer from each pair contained a 5' T7 promoter sequence so that the resulting amplicon could be transcribed into RNA for optimal detection using the corresponding toehold switch.

Figures 3A, 3B, 3C, 3D, 3E:
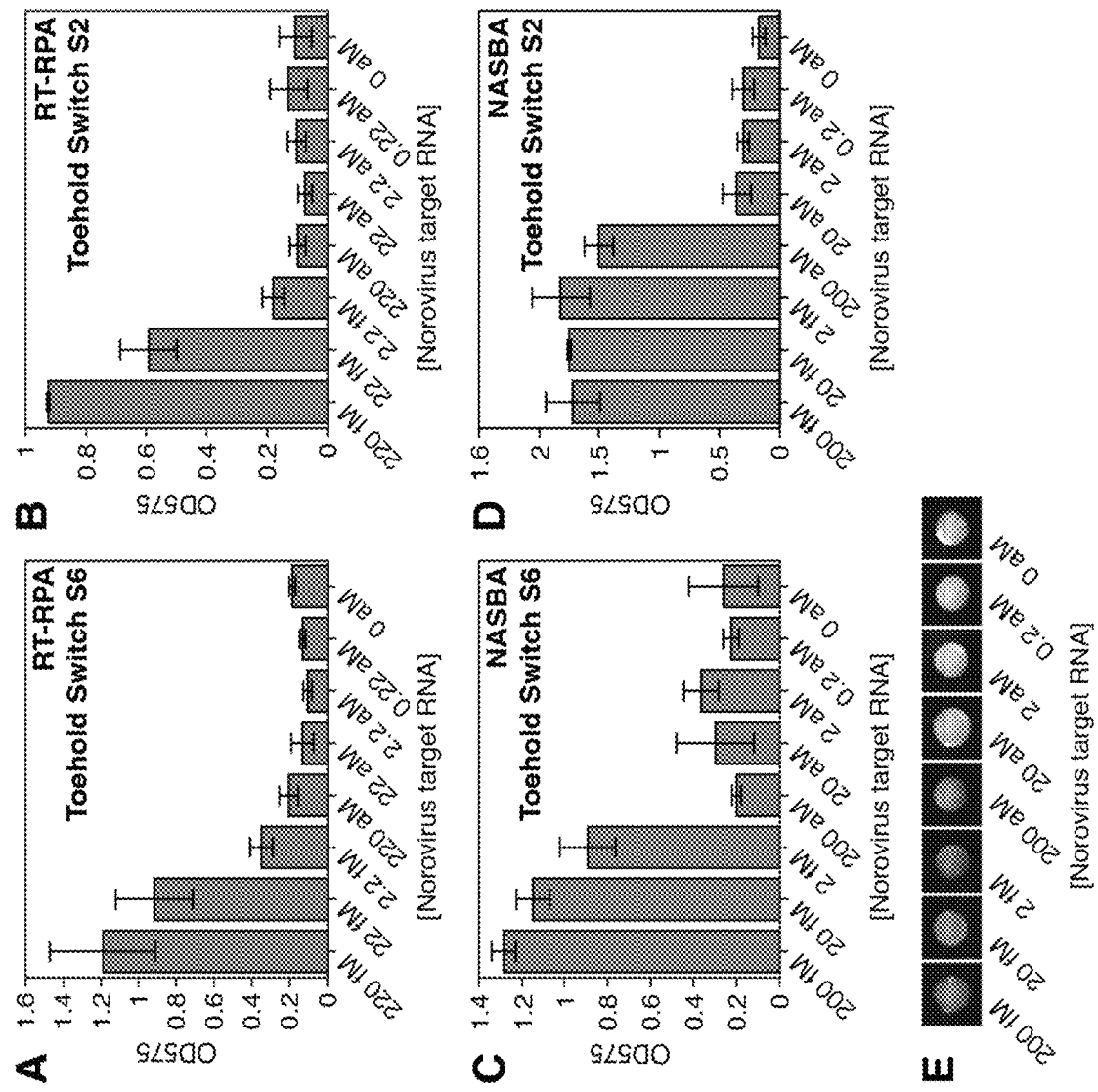
FIGS. 3A-3E demonstrate detection limit measurements for synthetic norovirus GII.4 target RNAs subject to isothermal amplification and detection using toehold switches. A,B, OD575 after amplification using RT-RPA and detection using toehold switches S6 (A) and S2 (B) in two-hour cell-free reactions. C,D, OD575 after amplification using NASBA and detection using toehold switch S6 (C) and S2 (D) in two-hour cell-free reactions. (E) Photographs of paper-based reactions using NASBA for amplification and toehold switch S2 for detection. Photographs were taken after 1 hour of the cell-free reactions.

Toehold switches S2 and S6 provided the lowest detection limits in the amplification tests. Two-hour amplification reactions were run with synthetic norovirus GII target RNAs ranging in concentration from 220 femtomoles/liter (fM) to 0.2 aM. The SI prefix "femto" represents a factor of $10^{-15}$, or in exponential notation, 1E-15. The amplified products were then diluted seven-fold and applied to the toehold switch reactions. For the RT-RPA reactions, both S2 and S6 toehold switches could detect down to 22 fM of the norovirus RNA with colorimetric outputs that could be readily discerned by eye (FIGS. 3A, 3B). Statistically significant concentrations as low as 2.2 fM could be detected from quantitative plate reader absorbance measurements for toehold switch S2 after 3 hours and toehold switch S6 after 1 hour.

NASBA tests provided improved detection limits compared to RPA. For toehold switch S6, we could discern concentrations down to 2 fM by eye within 2 hours and by plate reader within 1 hour (FIG. 3C). Although toehold switch S2 was not one of the very top performers in the initial screen (FIG. 2), it provided the lowest detection limit when coupled with NASBA. Experiments showed this sensor could detect down to 200 aM concentrations of the synthetic norovirus transcript (FIG. 3D). In addition, the sensor enabled detection by eye in 60 minutes at the 200 am detection limit as shown in FIG. 3E and by plate reader in 28 minutes. A concentration of 200 aM corresponds to 600 copies of the RNA template in the 5 μL NASBA reaction.

Diagnostic Validation with Active Norovirus

Figures 4A, 4B, 4C:
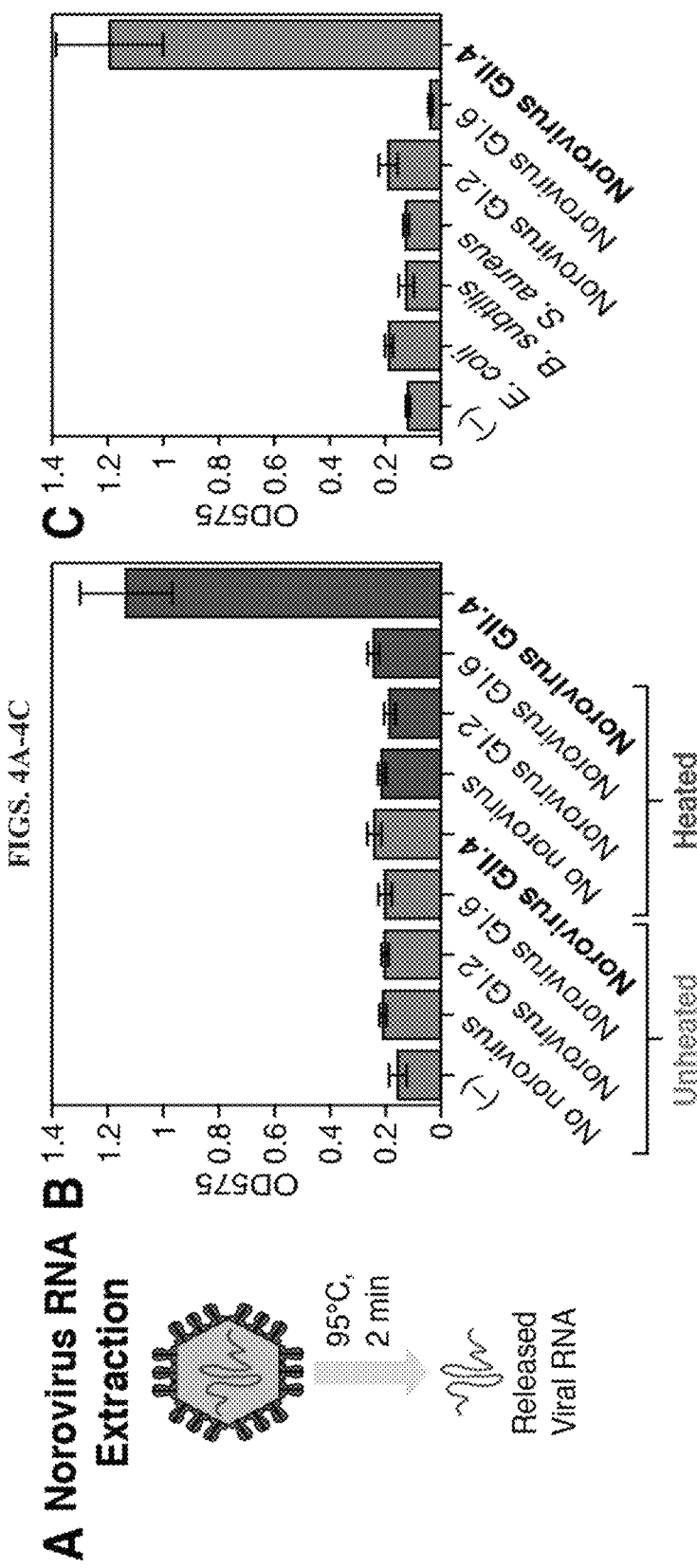
FIGS. 4A-4C demonstrate detection of live norovirus GII.4 Sydney and cross-reactivity testing. A, Norovirus RNA was extracted by diluting a stool sample 1:50 into PBS and briefly heating to 95° C. for 2 minutes. B, Measurement of OD575 after a two-hour paper-based reaction for a water-only negative control (−) and stool samples with and without norovirus particles before and after the brief heating treatment. All samples were subject to amplification via NASBA and detection with toehold switch S2. Only the heated norovirus GII.4 Sydney sample activates the toehold switch. C, Cross-reactivity testing of the assay against RNA from multiple bacteria, norovirus genotypes, and a water-only negative control. All samples were subject to NASBA and toehold switch S2 detection. OD575 was measured after two hours of the cell-free reaction.

To validate the detection platform, we performed experiments with active norovirus samples and tested the assay for cross-reactivity against other potential pathogens. Following previous reports on norovirus and our earlier work on the Zika virus, we first evaluated a simple method for extracting viral RNA from infected stool samples using a brief heating step. A norovirus GII.4 Sydney positive stool sample was diluted 1:50 in PBS and heated for two minutes at 95° C. (FIG. 4A). The same procedure was applied to a stool sample not infected with the virus and two additional stool samples containing norovirus GI.2 and GI.6. These heated samples, along with comparison unheated samples and a water-only negative control, were both amplified by NASBA over 2 hours and applied to a paper-based reaction with toehold switch S2. The unheated samples all yielded minimal changes in toehold switch output compared to the negative control. The OD575 of the heated sample with norovirus GII.4 Sydney increased to 1.13, while the OD575 of the other heated samples remained below 0.25 (FIG. 4B). Thus, the simple heating method was effective at releasing RNA from norovirus particles and the assay was specific for norovirus GII.4 Sydney.

To further evaluate cross-reactivity, we extracted RNA from *E. coli*, *B. subtilis*, and a methicillin-resistant *S. aureus* (MRSA) strain and added the RNA at masses of 80.6 ng, 123.5 ng, and 100.8 ng, respectively, to the NASBA reaction. RNA was also extracted from stool samples containing norovirus GII.4 Sydney, GI.2, and GI.6 and added to the NASBA reaction at a concentration of approximately 20 fM. None of these samples of bacterial RNA nor the GI.2 and GI.6 norovirus genotypes were able to activate toehold switch S2 for visual detection. The system was strongly activated by norovirus GII.4 Sydney RNA (FIG. 4C).

Norovirus Enrichment Using a Synbody-Based Magnetic Bead Technique

The ability to identify norovirus in dilute solutions or from large solution volumes is valuable for improving diagnostic sensitivity and for confirming complete decontamination of an area following an outbreak. For instance, dilute liquids, such as cleaning solutions from kitchen and bathroom surfaces, can be tested for residual virus following cleanup. To this end, we employed a synbody-based magnetic bead capture assay to concentrate norovirus from dilute solutions (FIG. 5A). Synbodies are synthetic bivalent affinity ligands composed of two 15- to 20-mer peptides screened to bind to the surface of a protein of interest. Synbodies have affinities and specificities similar to antibodies[41, 42]. Unlike antibodies, however, which often lose their affinity as norovirus strains evolve[1], synbodies have broad cross-affinity for multiple norovirus genotypes, which enables them to recognize a range of norovirus genotypes within both the GI and GII genogroups[35].

To capture and concentrate the virus, we took stool samples positive for norovirus GII.4 Sydney at a concentration of 270 fM as determined by qRT-PCR and prepared a series of higher dilutions ranging from $1:10^3$ to $1:10^7$ in PBS. Biotin-labelled synbody ASU1052, which was previously validated against multiple norovirus strains[35], and streptavidin-coated magnetic beads were added sequentially to the diluted samples with shaking at room temperature for 75 minutes total. After magnetic capture and washing, the beads were suspended with 50 μL of water and heated to 95° C. for 2 min to release the virus RNA. These virus samples, along with comparison ones heated but not subjected to synbody capture, were then amplified using NASBA and applied to paper-based cell-free systems containing toehold switch S2.

FIG. 5B displays the absorbance change produced from the reactions after two hours with the two different sets of samples. For synbody-concentrated samples, norovirus could be detected by eye with dilution factors up to $10^5$, which corresponds to a concentration of 2.7 aM. In contrast, none of the samples used directly and not subjected to concentration could be detected within two hours by eye. To further compare the two preparation methods, FIG. 5C shows the absorbance change over time for several virus samples. The synbody-concentrated sample prepared from a $10^5$ dilution crosses the eye-based detection threshold of OD575=0.4 in under two hours and provides a statistically significant positive signal in the plate reader after 66 minutes. The profile of the non-concentrated sample diluted 1000-fold nearly matches that of the synbody-concentrated sample diluted $10^6$-fold over the full 4-hour measurement. Both samples cross the visual detection threshold after 3 hours and provide positive results from quantitative plate reader measurements in approximately 2 hours, which correspond to norovirus GII.4 Sydney detection limits of 270 aM and 270 zM for the non-concentrated and synbody-concentrated samples, respectively. The synbody-based concentration technique thus enables a 1000-fold improvement in the detection limit of the norovirus assay.

To determine if the assay could also be applied to closely related norovirus genotypes, we also tested the systems against a stool sample with the norovirus GII.6 genotype. Virus particles were enriched using the ASU1052 synbodies and subject to NASBA using the primers optimized for GII.4 Sydney amplification. Unfortunately, these primers were not effective for this genotype. Primers modified to match the GII.6 genome, however, enabled successful amplification. Despite the presence of some mismatches between toehold switch S2 and its binding site on the GII.6 amplicon (see FIGS. 9A-9D), a visible OD575 signal was observed from paper-based reactions within two hours (FIG. 4D). Thus, toehold switch S2 is capable of detecting amplicons from both the norovirus GII.4 Sydney and GII.4 genotypes.

We have demonstrated a paper-based assay for detection of norovirus that does not require expensive thermal cycling equipment, provides test results that can be read directly by eye, and employs toehold switch riboregulators to eliminate false positives caused by non-specific amplification. The assay enables visual detection of norovirus down to a concentration of 270 aM from clinical stool samples containing live norovirus particles from the GII.4 Sydney genotype. The addition of a virus capture and concentration step using synbodies enables a further 1000-fold improvement in the sensitivity of the assay, allowing concentrations as low as 270 zM to be detected by eye after a three-hour paper-based reaction. This work also demonstrates that paper-based transcription-translation systems can remain active upon exposure to samples diluted from stool and confirms that RPA products can be successfully detected in the cell-free reactions, albeit with a higher detection limit than comparison NASBA products.

The norovirus assay provides significant improvements in sensitivity compared to our previously reported diagnostic assay for the Zika virus[31]. The Zika virus test provided a 1 fM detection limit against synthetic target RNAs and detected the virus from plasma at a concentration of 2.8 fM. In contrast, the norovirus assay demonstrated a 5-fold lower detection limit of 200 aM against a synthetic target and was successfully applied to a stool sample with a 270 aM concentration of norovirus. Addition of the synbody concentration step thus yielded an overall 5000-fold improvement in the detection limit. The Zika virus is known to be present at very low levels in symptomatic patients, with serum concentrations ranging from 8 zM to 6.1 fM with an average of 160 aM[43]. These concentrations are 10- to 100-fold lower than those observed for patients with the related dengue and chikungunya viruses[44]. Accordingly, our synbody-based concentration methods could prove valuable for extending the existing Zika test to more carriers of the virus. While the Zika diagnostic was only applied to a plasma sample from a viremic rhesus macaque, we have also demonstrated in this work that the diagnostic platform can be used on human stool samples, which can be used to identify many other causes of acute gastrointestinal illness beyond norovirus.

Although our norovirus assay provides sufficient sensitivity for detection from clinical samples, at present it requires 3-6 hours of processing time to reach a test result, which is substantially longer than many other diagnostics that employ isothermal amplification. We expect that large reductions in assay time can be obtained by further optimization of the synbody-based enrichment technique, by designing toehold switches optimized for quicker and stronger output, and by implementing new reporter proteins with faster activation. Indeed, the substantial decrease in reaction time that we observed using a-complementation of lacZ suggests that there is ample room for improvement using alternative reporters. Moreover, use of faster amplification techniques such as RT-RPA with improved primers or strand-displacement amplification (SDA) could further decrease the time to detection for the technique. We also expect that toehold switch dynamic range against pathogen RNAs can be improved with continued refinement of in silico selection algorithms. In particular, screening experiments examining larger numbers of toehold switches against diverse target RNAs will be essential for generating in silico design scoring functions that are able to accurately predict their performance when deployed in cell-free transcription-translation systems.

The assay can also be improved by reducing its cost. In addition to the ~$1/test price of the paper-based component of the assay[30], the per test costs of NASBA, streptavidin-coated magnetic beads, and biotinylated synbodies are $2.25, $5.38, and $0.10, respectively. The total cost in materials for the assay is thus $8.73 and the overall assay requires approximately 35 minutes of hands on time. A previous study in South Africa to assess GeneXpert cartridge costs has reported an average lab technician salary of $9.07/hr,[14] which brings the total assay cost to $14.02 with labor included. Materials costs for this estimate are based on retail prices for the components. It is likely that the quantities of magnetic beads used in the assay can be reduced substantially with further refinement of the experimental procedures, and materials costs can decrease with purchases at larger scales. Even without optimization of the assay toward reduced price, the total cost per assay remains lower than the $14.93 calculated for GeneXpert cartridges in South Africa where concessional pricing is in effect[14]. Furthermore, our assay does not require large initial expenditures for purchasing expensive equipment.

The continual emergence of new variants of norovirus means that our paper-based assay will need to be updated as other strains replace GII.4 Sydney to ensure that false negatives do not occur. For instance, the GII.P17-GII.17 norovirus strain has recently become predominant in Asia[10] and immunochromatographic tests, which were developed for the GII.4 strain, have demonstrated 1000-fold poorer detection limits against the emergent strain[45]. To reduce the probability of false negatives, our assay employs a target sequence that is well conserved across different GII strains, including GII.P17 and GII.17. The toehold switch S2 sensor is predicted by NUPACK simulations to tolerate several mismatches in the target RNA, particularly within the toehold region, and still expose the RBS and start codon to enable translation of the reporter gene (see FIGS. 9A-9D). This resiliency against sequence variations is evidenced by the ability of device S2 to activate against the GII.6 strain (FIG. 5D). In cases where there is larger sequence divergence, sensor mRNAs that employ multiple toehold switch hairpins upstream of a single output gene can be used to detect different norovirus strains or to compensate for locations with higher sequence variability to avoid false negatives. We have demonstrated that such OR logic systems can be used to detect six completely sequence-independent target RNAs using a single sensor mRNA in $E.\ coli$[36]. We expect that similar approaches can be used in the paper-based reactions and prove more parsimonious with cell-free systems resources than other implementations employing multiple independent mRNAs. Like other nucleic acid tests that employ amplification, false negatives can also occur when the amplification primers do not have sufficient homology with the target amplicon. Such sequence variability can be addressed using primers with degenerate bases at positions known to have high probability of sequence divergence.

Despite these areas for improvement, the reasonably low cost of the assay and its reliance on only inexpensive equipment enables it to be implemented in decentralized contexts such as remote clinics or cruise ships with trained operators. Furthermore, coupling the validated molecular components of the assay with companion hardware for incubation and readout[31] or liquid handling[46] has the potential to substantially reduce operator training requirements and lead to more widespread deployment in the future. Lastly, the demonstrated ability of synbodies and toehold switches to bind to proteins and nucleic acids, respectively, from a variety of different pathogens[30-32, 41, 42] indicates that our combined concentration and detection approach can be successfully applied to a diverse range of infectious agents.

We claim:

1. A synthetic norovirus-specific toehold switch comprising, in order 5' to 3', a toehold domain, a first stem domain a loop domain, a second stem domain, and at least a portion of a coding sequence of a reporter gene, wherein the first stem domain, the loop domain, and second stem domain anneal to form a fully or partially double-stranded stem-loop structure, wherein the toehold domain and at least a portion of the first stem domain are complementary to a target norovirus RNA sequence, and wherein the toehold switch comprises a sequence selected from SEQ ID NOs:1-12.

2. A kit for detecting a norovirus-associated nucleic acid, comprising a norovirus specific synbody, at least one synthetic norovirus-specific toehold switch, and an electronic optical reader,
   wherein the at least one toehold switch is provided in at least one preserved test article, and
   wherein each synthetic norovirus-specific toehold switch comprises, in order from 5' to 3', a toehold domain, a first stem domain, a loop domain, a second stem domain, and at least a portion of a coding sequence of a reporter gene, wherein the first stem domain, the loop domain, and second stem domain anneal to form a fully or partially double-stranded stem-loop structure, wherein the toehold domain and at least a portion of the first stem domain are complementary to a target norovirus RNA sequence, and wherein the toehold switch comprises a sequence selected from SEQ ID NOs:1-12.

3. The kit of claim 2, wherein the at least one preserved test article comprises one or more of a preserved paper test article and a preserved test tube article.

4. The kit of claim 2, further comprising instructions for performing a method of detecting a target norovirus RNA sequence in a sample.

5. The kit of claim 2, wherein the synbody comprises biotin.

6. The kit of claim 5, wherein the biotin-containing synbody is bound to a streptavidin-coated magnetic bead.

7. A method of detecting a norovirus nucleic acid in a sample, the method comprising the steps of:

(a) contacting a biological sample obtained from a subject to a norovirus detection agent under conditions that promote binding of the norovirus detection agent to the norovirus nucleic acid if present in the sample;
(b) isolating nucleic acids from the sample bound by the norovirus detection agent;
(c) amplifying the isolated nucleic acids using isothermal amplification; and
(d) contacting the amplified nucleic acid to a toehold switch of claim 1, wherein the contacting occurs under conditions that allow translation of the coding domain in the presence of the norovirus nucleic acid but not in the absence of the norovirus nucleic acid, and detecting the reporter protein as an indicator that the norovirus nucleic acid is present in the amplified nucleic acids.

8. The method of claim 7, wherein norovirus nucleic acid is detected at concentrations in a range of zeptomoles/liter (zM).

9. The method of claim 7, wherein norovirus nucleic acid is detected at concentration between about 270 zM to about 270 aM.

10. The method of claim 7, wherein the norovirus detection agent is a synbody.

11. The method of claim 10, wherein the synbody comprises biotin.

12. The method of claim 11, wherein the biotin-containing synbody is bound to a streptavidin-coated magnetic bead.

13. The method of claim 11, wherein isolating comprises a magnetic capture assay.

14. The method of claim 7, wherein the toehold switch encodes at least a portion of lacZ.

15. The method of claim 7, wherein the toehold switch encodes lacZα and the amplified nucleic acids are contacted under conditions which promote formation of a lacZ tetramer.

16. The method of claim 15, wherein lacZω is provided on a substrate to which the amplified nucleic acids are contacted.

* * * * *

SEQUENCE LISTING

<160> NUMBER OF SEQ ID NOS: 82

<210> SEQ ID NO 1
<211> LENGTH: 103
<212> TYPE: RNA
<213> ORGANISM: Artificial Sequence
<220> FEATURE:
<223> OTHER INFORMATION: sythetic

<400> SEQUENCE: 1
gggccaucuu cauucacaaa acugggagcc agauugcgag gacuuuagaa cagaggagau      60
aaagaugucg caaucuggaa ccuggcggca gcgcaagaag aug                      103

<210> SEQ ID NO 2
<211> LENGTH: 103
<212> TYPE: RNA
<213> ORGANISM: Artificial Sequence
<220> FEATURE:
<223> OTHER INFORMATION: synthetic

<400> SEQUENCE: 2
gggaucgccc ucccacgugc ucagaucuga gaaucucaug gacuuuagaa cagaggagau      60
aaagaugaug agauucucaa ccuggcggca gcgcaagaag aug                      103

<210> SEQ ID NO 3
<211> LENGTH: 103
<212> TYPE: RNA
<213> ORGANISM: Artificial Sequence
<220> FEATURE:
<223> OTHER INFORMATION: synthetic

<400> SEQUENCE: 3
gggacaaaac ugggagccag auugcgaucg cccucccacg gacuuuagaa cagaggagau      60
aaagauggug ggagggcgaa ccuggcggca gcgcaagaag aug                      103

<210> SEQ ID NO 4
<211> LENGTH: 103
<212> TYPE: RNA
<213> ORGANISM: Artificial Sequence
<220> FEATURE:
<223> OTHER INFORMATION: synthetic

<400> SEQUENCE: 4
gggcugggac gagguuggcu gcggacccau cagaugggug gacuuuagaa cagaggagau      60
aaagaugacc caucugauaa ccuggcggca gcgcaagaag aug                      103

<210> SEQ ID NO 5
<211> LENGTH: 102
<212> TYPE: RNA
<213> ORGANISM: Artificial Sequence
<220> FEATURE:
<223> OTHER INFORMATION: synthetic

<400> SEQUENCE: 5
gggucauucg acgccaucuu cauucacaaa acugggaggg acuuuagaac agaggagaua      60
aagaugcucc caguuuuaac cuggcggcag cgcaagaaga ug                       102

<210> SEQ ID NO 6
<211> LENGTH: 103
<212> TYPE: RNA
<213> ORGANISM: Artificial Sequence
<220> FEATURE:
<223> OTHER INFORMATION: synthetic

```
<400> SEQUENCE: 6
gggagccaga uugcgaucgc ccucccacgu gcucagaucg gacuuuagaa cagaggagau      60
aaagauggau cugagcacaa ccuggcggca gcgcaagaag aug                       103

<210> SEQ ID NO 7
<211> LENGTH: 103
<212> TYPE: RNA
<213> ORGANISM: Artificial Sequence
<220> FEATURE:
<223> OTHER INFORMATION: synthetic

<400> SEQUENCE: 7
gggucugaug gguccgcagc caaccucguc ccagaggucg gacuuuagaa cagaggagau      60
aaagauggac cucugggaaa ccuggcggca gcgcaagaag aug                       103

<210> SEQ ID NO 8
<211> LENGTH: 102
<212> TYPE: RNA
<213> ORGANISM: Artificial Sequence
<220> FEATURE:
<223> OTHER INFORMATION: synthetic

<400> SEQUENCE: 8
gggugggagg gcgaucgcaa ucuggcuccc aguuuugugg acuuuagaac agaggagaua      60
aagaugacaa aacugggaac cuggcggcag cgcaagaaga ug                        102

<210> SEQ ID NO 9
<211> LENGTH: 103
<212> TYPE: RNA
<213> ORGANISM: Artificial Sequence
<220> FEATURE:
<223> OTHER INFORMATION: synthetic

<400> SEQUENCE: 9
gggugugaau aagauggcg ucgaaugacg ccaacccaug gacuuuagaa cagaggagau       60
aaagaugaug gguuggcgaa ccuggcggca gcgcaagaag aug                       103

<210> SEQ ID NO 10
<211> LENGTH: 103
<212> TYPE: RNA
<213> ORGANISM: Artificial Sequence
<220> FEATURE:
<223> OTHER INFORMATION: synthetic

<400> SEQUENCE: 10
gggagaucug agcacguggg agggcgaucg caaucuggcg gacuuuagaa cagaggagau      60
aaagauggcc agauugcgaa ccuggcggca gcgcaagaag aug                       103

<210> SEQ ID NO 11
<211> LENGTH: 103
<212> TYPE: RNA
<213> ORGANISM: Artificial Sequence
<220> FEATURE:
<223> OTHER INFORMATION: synthetic

<400> SEQUENCE: 11
gggaucgcaa ucuggcuccc aguuuguga augaagaugg gacuuuagaa cagaggagau       60
aaagaugcau cuucauucaa ccuggcggca gcgcaagaag aug                       103

<210> SEQ ID NO 12
```

```
<211> LENGTH: 103
<212> TYPE: RNA
<213> ORGANISM: Artificial Sequence
<220> FEATURE:
<223> OTHER INFORMATION: synthetic

<400> SEQUENCE: 12
gggucgaaug acgccaaccc aucugauggg uccgcagccg acuuuagaa cagaggagau    60 aaagaugggc ugcggaccaa ccuggcggca gcgcaagaag aug                    103

<210> SEQ ID NO 13
<211> LENGTH: 198
<212> TYPE: RNA
<213> ORGANISM: Artificial Sequence
<220> FEATURE:
<223> OTHER INFORMATION: synthetic

<400> SEQUENCE: 13
auggauuuuu acgugcccag gcaagagcca auguucagau ggaugagauu cucagaucug    60
agcacguggg agggcgaucg caaucuggcu cccaguuuug ugaaugaaga uggcgucgaa   120
ugacgccaac ccaucugaug gguccgcagc caaccucguc ccagaggucu acaaugaggu   180
uauggcuuug gagcccgu                                                 198

<210> SEQ ID NO 14
<211> LENGTH: 198
<212> TYPE: RNA
<213> ORGANISM: Artificial Sequence
<220> FEATURE:
<223> OTHER INFORMATION: synthetic

<400> SEQUENCE: 14
acgggcucca agccauaac cucauuguug accucuggga cgagguuggc ugcggaccca    60
ucagaugggu uggcgucauu cgacgccauc uucauucaca aaacugggag ccagauugcg   120
aucgcccucc cacgugcuca gaucugagaa ucucauccau cugaacauug gcucuugccu   180
gggcacguaa aaauccau                                                 198

<210> SEQ ID NO 15
<211> LENGTH: 178
<212> TYPE: RNA
<213> ORGANISM: Artificial Sequence
<220> FEATURE:
<223> OTHER INFORMATION: synthetic

<400> SEQUENCE: 15
auggauuuuu augugcccag acaagaguca auguucagau ggaugagguu cucagaucua    60
agcacauggg agggcgaucg caaucuggcu cccaguuuug ugaaugaaga uggcgucgaa   120
ugacgccgcu ccaucuaaug auggugcugc uggucucgua ccagagggca acaacgag     178

<210> SEQ ID NO 16
<211> LENGTH: 178
<212> TYPE: RNA
<213> ORGANISM: Artificial Sequence
<220> FEATURE:
<223> OTHER INFORMATION: synthetic

<400> SEQUENCE: 16
auggauuuuu augugcccag acaagaguca auguucagau ggaugagguu cucagaucua    60
agcacauggg agggcgaucg caaucuggcu cccaguuuug ugaaugaaga uggcgucgaa   120
ugacgccgcu ccaucuaaug auggugcugc uggucucgua ccagagggca acaacgag     178
```

<210> SEQ ID NO 17
<211> LENGTH: 185
<212> TYPE: RNA
<213> ORGANISM: Artificial Sequence
<220> FEATURE:
<223> OTHER INFORMATION: synthetic

<400> SEQUENCE: 17
uggaguuuua ugugcccaga caagaggcca uguucaggug gaugagauuc ucugaccuca    60
gcacauggga gggcgaucgc aaucuugcuc ccgagggugu gaaugaagau ggcgucgaau   120
gacgcugcuc caucgaauga uggugcugcc aaccucguac cagaggccaa caaugagguu   180
auggc                                                              185

<210> SEQ ID NO 18
<211> LENGTH: 28
<212> TYPE: RNA
<213> ORGANISM: Artificial Sequence
<220> FEATURE:
<223> OTHER INFORMATION: synthetic

<400> SEQUENCE: 18
ggacuuuaga acagaggaga uaaagaug                                      28

<210> SEQ ID NO 19
<211> LENGTH: 31
<212> TYPE: RNA
<213> ORGANISM: Artificial Sequence
<220> FEATURE:
<223> OTHER INFORMATION: synthetic

<400> SEQUENCE: 19
aaccuggcgg cagcgcaaga agaugcguaa a                                  31

<210> SEQ ID NO 20
<211> LENGTH: 22
<212> TYPE: DNA
<213> ORGANISM: Artificial Sequence
<220> FEATURE:
<223> OTHER INFORMATION: synthetic

<400> SEQUENCE: 20
taactagcat aaccccttgg gg                                            22

<210> SEQ ID NO 21
<211> LENGTH: 18
<212> TYPE: DNA
<213> ORGANISM: Artificial Sequence
<220> FEATURE:
<223> OTHER INFORMATION: synthetic

<400> SEQUENCE: 21
catatggctg ccgcgcgg                                                 18

<210> SEQ ID NO 22
<211> LENGTH: 59
<212> TYPE: DNA
<213> ORGANISM: Artificial Sequence
<220> FEATURE:
<223> OTHER INFORMATION: synthetic

<400> SEQUENCE: 22
agcggcctgg tgccgcgcgg cagccatatg cgtaaaatga ccatgattac ggattcact    59

<210> SEQ ID NO 23
<211> LENGTH: 53
<212> TYPE: DNA
<213> ORGANISM: Artificial Sequence
<220> FEATURE:
<223> OTHER INFORMATION: synthetic

<400> SEQUENCE: 23
tttagaggcc ccaaggggtt atgctagtta tttttgacac cagaccaact ggt      53

<210> SEQ ID NO 24
<211> LENGTH: 18
<212> TYPE: DNA
<213> ORGANISM: Artificial Sequence
<220> FEATURE:
<223> OTHER INFORMATION: synthetic

<400> SEQUENCE: 24
aacagttgcg cagcctga                                              18

<210> SEQ ID NO 25
<211> LENGTH: 25
<212> TYPE: DNA
<213> ORGANISM: Artificial Sequence
<220> FEATURE:
<223> OTHER INFORMATION: synthetic

<400> SEQUENCE: 25
ccagtgaatc cgtaatcatg gtcat                                      25

<210> SEQ ID NO 26
<211> LENGTH: 41
<212> TYPE: DNA
<213> ORGANISM: Artificial Sequence
<220> FEATURE:
<223> OTHER INFORMATION: synthetic

<400> SEQUENCE: 26
atgaccatga ttacggattc actggccgtc gccgcaccg a                     41

<210> SEQ ID NO 27
<211> LENGTH: 40
<212> TYPE: DNA
<213> ORGANISM: Artificial Sequence
<220> FEATURE:
<223> OTHER INFORMATION: synthetic

<400> SEQUENCE: 27
tcaggctgcg caactgttgg gaagggcgat cggtgcgggc                      40

<210> SEQ ID NO 28
<211> LENGTH: 19
<212> TYPE: DNA
<213> ORGANISM: Artificial Sequence
<220> FEATURE:
<223> OTHER INFORMATION: synthetic

<400> SEQUENCE: 28
tagcataacc ccttggggc                                             19

<210> SEQ ID NO 29
<211> LENGTH: 18
<212> TYPE: DNA
<213> ORGANISM: Artificial Sequence
<220> FEATURE:
<223> OTHER INFORMATION: synthetic

<400> SEQUENCE: 29
gcgcaactgt tgggaagg                                                    18

<210> SEQ ID NO 30
<211> LENGTH: 52
<212> TYPE: DNA
<213> ORGANISM: Artificial Sequence
<220> FEATURE:
<223> OTHER INFORMATION: synthetic

<400> SEQUENCE: 30
cgcaccgatc gcccttccca acagttgcgc agcctgaatg gcgaatggta at              52

<210> SEQ ID NO 31
<211> LENGTH: 52
<212> TYPE: DNA
<213> ORGANISM: Artificial Sequence
<220> FEATURE:
<223> OTHER INFORMATION: synthetic

<400> SEQUENCE: 31
cccgtttaga ggccccaagg ggttatgcta ttattaccat tcgccattca gg              52

<210> SEQ ID NO 32
<211> LENGTH: 30
<212> TYPE: DNA
<213> ORGANISM: Artificial Sequence
<220> FEATURE:
<223> OTHER INFORMATION: synthetic

<400> SEQUENCE: 32
atgaccatga ttacggattc actggccgtc                                       30

<210> SEQ ID NO 33
<211> LENGTH: 52
<212> TYPE: DNA
<213> ORGANISM: Artificial Sequence
<220> FEATURE:
<223> OTHER INFORMATION: synthetic

<400> SEQUENCE: 33
ccggctaccg tagaaacgcg aatttactag cataagggag agcgtcgaga tc              52

<210> SEQ ID NO 34
<211> LENGTH: 54
<212> TYPE: DNA
<213> ORGANISM: Artificial Sequence
<220> FEATURE:
<223> OTHER INFORMATION: synthetic

<400> SEQUENCE: 34
ctagtaaatt cgcgtttcta cggtagccgg gcgctaatac gactcactat aggg            54

<210> SEQ ID NO 35
<211> LENGTH: 52
<212> TYPE: DNA
<213> ORGANISM: Artificial Sequence
<220> FEATURE:
<223> OTHER INFORMATION: synthetic

<400> SEQUENCE: 35
gacggccagt gaatccgtaa tcatggtcat cttcttgcgc tgccgccagg tt              52

<210> SEQ ID NO 36

```
<211> LENGTH: 124
<212> TYPE: DNA
<213> ORGANISM: Artificial Sequence
<220> FEATURE:
<223> OTHER INFORMATION: synthetic

<400> SEQUENCE: 36
gcgctaatac gactcactat agggccatct tcattcacaa aactgggagc cagattgcga      60
ggactttaga acagaggaga taaagatgtc gcaatctgga acctggcggc agcgcaagaa     120
gatg                                                                  124

<210> SEQ ID NO 37
<211> LENGTH: 124
<212> TYPE: DNA
<213> ORGANISM: Artificial Sequence
<220> FEATURE:
<223> OTHER INFORMATION: synthetic

<400> SEQUENCE: 37
gcgctaatac gactcactat agggatcgcc ctcccacgtg ctcagatctg agaatctcat      60
ggactttaga acagaggaga taaagatgat gagattctca acctggcggc agcgcaagaa     120
gatg                                                                  124

<210> SEQ ID NO 38
<211> LENGTH: 124
<212> TYPE: DNA
<213> ORGANISM: Artificial Sequence
<220> FEATURE:
<223> OTHER INFORMATION: synthetic

<400> SEQUENCE: 38
gcgctaatac gactcactat agggacaaaa ctgggagcca gattgcgatc gccctcccac      60
ggactttaga acagaggaga taaagatggt gggagggcga acctggcggc agcgcaagaa     120
gatg                                                                  124

<210> SEQ ID NO 39
<211> LENGTH: 124
<212> TYPE: DNA
<213> ORGANISM: Artificial Sequence
<220> FEATURE:
<223> OTHER INFORMATION: synthetic

<400> SEQUENCE: 39
gcgctaatac gactcactat agggctggga cgaggttggc tgcggaccca tcagatgggt      60
ggactttaga acagaggaga taaagatgac ccatctgata acctggcggc agcgcaagaa     120
gatg                                                                  124

<210> SEQ ID NO 40
<211> LENGTH: 123
<212> TYPE: DNA
<213> ORGANISM: Artificial Sequence
<220> FEATURE:
<223> OTHER INFORMATION: synthetic

<400> SEQUENCE: 40
gcgctaatac gactcactat agggtcattc gacgccatct tcattcacaa aactgggagg      60
gactttagaa cagaggagat aaagatgctc ccagttttaa cctggcggca gcgcaagaag     120
atg                                                                   123
```

<210> SEQ ID NO 41
<211> LENGTH: 124
<212> TYPE: DNA
<213> ORGANISM: Artificial Sequence
<220> FEATURE:
<223> OTHER INFORMATION: synthetic

<400> SEQUENCE: 41
gcgctaatac gactcactat agggagccag attgcgatcg ccctcccacg tgctcagatc    60
ggactttaga acagaggaga taaagatgga tctgagcaca acctggcggc agcgcaagaa   120
gatg                                                                124

<210> SEQ ID NO 42
<211> LENGTH: 124
<212> TYPE: DNA
<213> ORGANISM: Artificial Sequence
<220> FEATURE:
<223> OTHER INFORMATION: synthetic

<400> SEQUENCE: 42
gcgctaatac gactcactat agggtctgat gggtccgcag ccaacctcgt cccagaggtc    60
ggactttaga acagaggaga taaagatgga cctctgggaa acctggcggc agcgcaagaa   120
gatg                                                                124

<210> SEQ ID NO 43
<211> LENGTH: 123
<212> TYPE: DNA
<213> ORGANISM: Artificial Sequence
<220> FEATURE:
<223> OTHER INFORMATION: synthetic

<400> SEQUENCE: 43
gcgctaatac gactcactat agggtgggag ggcgatcgca atctggctcc cagttttgtg    60
gactttagaa cagaggagat aaagatgaca aaactgggaa cctggcggca gcgcaagaag   120
atg                                                                 123

<210> SEQ ID NO 44
<211> LENGTH: 124
<212> TYPE: DNA
<213> ORGANISM: Artificial Sequence
<220> FEATURE:
<223> OTHER INFORMATION: synthetic

<400> SEQUENCE: 44
gcgctaatac gactcactat agggtgtgaa tgaagatggc gtcgaatgac gccaacccat    60
ggactttaga acagaggaga taaagatgat gggttggcga acctggcggc agcgcaagaa   120
gatg                                                                124

<210> SEQ ID NO 45
<211> LENGTH: 124
<212> TYPE: DNA
<213> ORGANISM: Artificial Sequence
<220> FEATURE:
<223> OTHER INFORMATION: synthetic

<400> SEQUENCE: 45
gcgctaatac gactcactat agggagatct gagcacgtgg gagggcgatc gcaatctggc    60
ggactttaga acagaggaga taaagatggc cagattgcga acctggcggc agcgcaagaa   120
gatg                                                                124

<210> SEQ ID NO 46
<211> LENGTH: 124
<212> TYPE: DNA
<213> ORGANISM: Artificial Sequence
<220> FEATURE:
<223> OTHER INFORMATION: synthetic

<400> SEQUENCE: 46

```
gcgctaatac gactcactat agggatcgca atctggctcc cagttttgtg aatgaagatg    60
ggactttaga acagaggaga taaagatgca tcttcattca acctggcggc agcgcaagaa   120
gatg                                                                124
```

<210> SEQ ID NO 47
<211> LENGTH: 124
<212> TYPE: DNA
<213> ORGANISM: Artificial Sequence
<220> FEATURE:
<223> OTHER INFORMATION: synthetic

<400> SEQUENCE: 47

```
gcgctaatac gactcactat agggtcgaat gacgccaacc catctgatgg gtccgcagcc    60
ggactttaga acagaggaga taaagatggg ctgcggacca acctggcggc agcgcaagaa   120
gatg                                                                124
```

<210> SEQ ID NO 48
<211> LENGTH: 26
<212> TYPE: DNA
<213> ORGANISM: Artificial Sequence
<220> FEATURE:
<223> OTHER INFORMATION: synthetic

<400> SEQUENCE: 48

```
cgttactggt ttcacattca ccaccc                                         26
```

<210> SEQ ID NO 49
<211> LENGTH: 19
<212> TYPE: DNA
<213> ORGANISM: Artificial Sequence
<220> FEATURE:
<223> OTHER INFORMATION: synthetic

<400> SEQUENCE: 49

```
cctgccacca tacccacgc                                                 19
```

<210> SEQ ID NO 50
<211> LENGTH: 55
<212> TYPE: DNA
<213> ORGANISM: Artificial Sequence
<220> FEATURE:
<223> OTHER INFORMATION: synthetic

<400> SEQUENCE: 50

```
aattctaata cgactcacta tagggagaag gattctcaga tctgagcacg tggga         55
```

<210> SEQ ID NO 51
<211> LENGTH: 20
<212> TYPE: DNA
<213> ORGANISM: Artificial Sequence
<220> FEATURE:
<223> OTHER INFORMATION: synthetic

<400> SEQUENCE: 51

```
attgttgacc tctgggacga                                                20
```

<210> SEQ ID NO 52
<211> LENGTH: 53
<212> TYPE: DNA
<213> ORGANISM: Artificial Sequence
<220> FEATURE:
<223> OTHER INFORMATION: synthetic

<400> SEQUENCE: 52
aattctaata cgactcacta tagggagaag gcaggcaaga gccaatgttc aga         53

<210> SEQ ID NO 53
<211> LENGTH: 20
<212> TYPE: DNA
<213> ORGANISM: Artificial Sequence
<220> FEATURE:
<223> OTHER INFORMATION: synthetic

<400> SEQUENCE: 53
ctcattgttg acctctggga                                              20

<210> SEQ ID NO 54
<211> LENGTH: 54
<212> TYPE: DNA
<213> ORGANISM: Artificial Sequence
<220> FEATURE:
<223> OTHER INFORMATION: synthetic

<400> SEQUENCE: 54
aattctaata cgactcacta tagggagaag ggcaagagcc aatgttcaga tgga        54

<210> SEQ ID NO 55
<211> LENGTH: 20
<212> TYPE: DNA
<213> ORGANISM: Artificial Sequence
<220> FEATURE:
<223> OTHER INFORMATION: synthetic

<400> SEQUENCE: 55
ctcattgttg acctctggga                                              20

<210> SEQ ID NO 56
<211> LENGTH: 51
<212> TYPE: DNA
<213> ORGANISM: Artificial Sequence
<220> FEATURE:
<223> OTHER INFORMATION: synthetic

<400> SEQUENCE: 56
aattctaata cgactcacta tagggagaag ggctccaaag ccataacctc a           51

<210> SEQ ID NO 57
<211> LENGTH: 23
<212> TYPE: DNA
<213> ORGANISM: Artificial Sequence
<220> FEATURE:
<223> OTHER INFORMATION: synthetic

<400> SEQUENCE: 57
gcaagagcca atgttcagat gga                                          23

<210> SEQ ID NO 58
<211> LENGTH: 51
<212> TYPE: DNA
<213> ORGANISM: Artificial Sequence
<220> FEATURE:

<223> OTHER INFORMATION: synthetic

<400> SEQUENCE: 58
aattctaata cgactcacta tagggagaag gctcattgtt gacctctggg a         51

<210> SEQ ID NO 59
<211> LENGTH: 24
<212> TYPE: DNA
<213> ORGANISM: Artificial Sequence
<220> FEATURE:
<223> OTHER INFORMATION: synthetic

<400> SEQUENCE: 59
gatggatgag attctcagat ctga                                       24

<210> SEQ ID NO 60
<211> LENGTH: 51
<212> TYPE: DNA
<213> ORGANISM: Artificial Sequence
<220> FEATURE:
<223> OTHER INFORMATION: synthetic

<400> SEQUENCE: 60
aattctaata cgactcacta tagggagaag gctcattgtt gacctctggg a         51

<210> SEQ ID NO 61
<211> LENGTH: 22
<212> TYPE: DNA
<213> ORGANISM: Artificial Sequence
<220> FEATURE:
<223> OTHER INFORMATION: synthetic

<400> SEQUENCE: 61
caagagccaa tgttcagatg ga                                         22

<210> SEQ ID NO 62
<211> LENGTH: 51
<212> TYPE: DNA
<213> ORGANISM: Artificial Sequence
<220> FEATURE:
<223> OTHER INFORMATION: synthetic

<400> SEQUENCE: 62
aattctaata cgactcacta tagggagaag gcagacaaga ggccatgttc a         51

<210> SEQ ID NO 63
<211> LENGTH: 22
<212> TYPE: DNA
<213> ORGANISM: Artificial Sequence
<220> FEATURE:
<223> OTHER INFORMATION: synthetic

<400> SEQUENCE: 63
tcattgttgg cctctggtac ga                                         22

<210> SEQ ID NO 64
<211> LENGTH: 70
<212> TYPE: RNA
<213> ORGANISM: Artificial Sequence
<220> FEATURE:
<223> OTHER INFORMATION: synthetic
<220> FEATURE:
<221> NAME/KEY: misc_feature
<222> LOCATION: (29)..(39)
<223> OTHER INFORMATION: n is a, c, g, or u

<400> SEQUENCE: 64

```
ggacuuuaga acagaggaga uaaagaugnn nnnnnnnnna accuggcggc agcgcaagaa    60
gaugcguaaa                                                           70

<210> SEQ ID NO 65
<211> LENGTH: 36
<212> TYPE: RNA
<213> ORGANISM: Artificial Sequence
<220> FEATURE:
<223> OTHER INFORMATION: synthetic

<400> SEQUENCE: 65
augagauucu cagaucugag cacgugggag ggcgau                              36

<210> SEQ ID NO 66
<211> LENGTH: 36
<212> TYPE: RNA
<213> ORGANISM: Artificial Sequence
<220> FEATURE:
<223> OTHER INFORMATION: synthetic

<400> SEQUENCE: 66
augagauucu cugaccucag cacaugggag ggcgau                              36

<210> SEQ ID NO 67
<211> LENGTH: 36
<212> TYPE: RNA
<213> ORGANISM: Artificial Sequence
<220> FEATURE:
<223> OTHER INFORMATION: synthetic

<400> SEQUENCE: 67
augagguucu cagaucuaag cacaugggag ggcgau                              36

<210> SEQ ID NO 68
<211> LENGTH: 36
<212> TYPE: RNA
<213> ORGANISM: Artificial Sequence
<220> FEATURE:
<223> OTHER INFORMATION: synthetic

<400> SEQUENCE: 68
augagguucu cagaucuaag cacaugggag ggcgau                              36

<210> SEQ ID NO 69
<211> LENGTH: 8746
<212> TYPE: DNA
<213> ORGANISM: Artificial Sequence
<220> FEATURE:
<223> OTHER INFORMATION: synthetic

<400> SEQUENCE: 69
ttcttgaaga cgaaagggcc tcgtgatacg cctatttta taggttaatg tcatgataat    60
aatggtttct tagacgtcag gtggcacttt tcggggaaat gtgcgcggaa ccccatttg   120 tttattttc taaatacatt caaatatgta tccgctcatg agacaataac cctgataaat   180
gcttcaataa tattgaaaaa ggaagagtat gagtattcaa catttccgtg tcgcccttat   240 tcccttttt gcggcatttt gccttcctgt ttttgctcac ccagaaacgc tggtgaaagt   300
aaaagatgct gaagatcagt tgggtgcacg agtgggttac atcgaactgg atctcaacag   360
cggtaagatc cttgagagtt ttcgccccga agaacgtttt ccaatgatga gcactttaa   420 agttctgcta tgtggcgcgg tattatcccg tgttgacgcc gggcaagagc aactcggtcg   480
```

```
ccgcatacac tattctcaga atgacttggt tgagtactca ccagtcacag aaaagcatct    540
tacggatggc atgacagtaa gagaattatg cagtgctgcc ataaccatga gtgataacac    600
tgcggccaac ttacttctga caacgatcgg aggaccgaag gagctaaccg cttttttgca    660
caacatgggg gatcatgtaa ctcgccttga tcgttgggaa ccggagctga atgaagccat    720
accaaacgac gagcgtgaca ccacgatgcc tgcagcaatg gcaacaacgt tgcgcaaact    780
attaactggc gaactactta ctctagcttc ccggcaacaa ttaatagact ggatggaggc    840
ggataaagtt gcaggaccac ttctgcgctc ggcccttccg gctggctggt ttattgctga    900
taaatctgga gccggtgagc gtgggtctcg cggtatcatt gcagcactgg ggccagatgg    960
taagccctcc cgtatcgtag ttatctacac gacggggagt caggcaacta tggatgaacg   1020
aaatagacag atcgctgaga taggtgcctc actgattaag cattggtaac tgtcagacca   1080
agtttactca tatatacttt agattgattt aaaacttcat ttttaattta aaaggatcta   1140
ggtgaagatc cttttggata atctcatgac caaaatccct taacgtgagt tttcgttcca   1200
ctgagcgtca gaccccgtag aaaagatcaa aggatcttct tgagatcctt ttttctgcg   1260 cgtaatctgc tgcttgcaaa caaaaaaacc accgctacca gcggtggttt gtttgccgga   1320
tcaagagcta ccaactcttt ttccgaaggt aactggcttc agcagagcgc agataccaaa   1380
tactgtcctt ctagtgtagc cgtagttagg ccaccacttc aagaactctg tagcaccgcc   1440
tacatacctc gctctgctaa tcctgttacc agtggctgct gccagtggcg ataagtcgtg   1500
tcttaccggg ttggactcaa gacgatagtt accggataag gcgcagcggt cgggctgaac   1560
ggggggttcg tgcacacagc ccagcttgga gcgaacgacc tacaccgaac tgagatacct   1620
acagcgtgag ctatgagaaa gcgccacgct tcccgaaggg agaaaggcgg acaggtatcc   1680
ggtaagcgga agggtcggaa caggagagcg cacgagggag cttccagggg gaaacgcctg   1740
gtatctttat agtcctgtcg ggtttcgcca cctctgactt gagcgtcgat ttttgtgatg   1800
ctcgtcaggg gggcggagcc tatggaaaaa cgccagcaac gcggcctttt tacgttcct   1860 ggccttttgc tggccttttg ctcacatgtt ctttcctgcg ttatcccctg attctgtgga   1920
taaccgtatt accgcctttg agtgagctga taccgctcgc cgcagccgaa cgaccgagcg   1980
cagcgagtca gtgagcgagg aagcggaaga gcgcctgatg cggtatttt ccttacgca    2040 tctgtgcggt atttcacacc gcatatatgg tgcactctca gtacaatctg ctctgatgcc   2100
gcatagttaa gccagtatac actccgctat cgctacgtga ctgggtcatg gctgcgcccc   2160
gacacccgcc aacacccgct gacgcgccct gacgggcttg tctgctcccg gcatccgctt   2220
acagacaagc tgtgaccgtc tccgggagct gcatgtgtca gaggttttca ccgtcatcac   2280
cgaaacgcgc gaggcagctg cggtaaagct catcagcgtg gtcgtgaagc gattcacaga   2340
tgtctgcctg ttcatccgcg tccagctcgt tgagtttctc cagaagcgtt aatgtctggc   2400
ttctgataaa gcgggccatg ttaagggcgg ttttttcctg tttggtcact gatgcctccg   2460
tgtaaggggg atttctgttc atgggggtaa tgataccgat gaaacgagag aggatgctca   2520
cgatacgggt tactgatgat gaacatgccc ggttactgga acgttgtgag ggtaaacaac   2580
tggcggtatg gatgcggcgg gaccagagaa aaatcactca gggtcaatgc cagcgcttcg   2640
ttaatacaga tgtaggtgtt ccacagggta gccagcagca tcctgcgatg cagatccgga   2700
acataatggt gcagggcgct gacttccgcg tttccagact ttacgaaaca cggaaaccga   2760
agaccattca tgttgttgct caggtcgcag acgttttgca gcagcagtcg cttcacgttc   2820
gctcgcgtat cggtgattca ttctgctaac cagtaaggca accccgccag cctagccggg   2880
```

```
tcctcaacga caggagcacg atcatgcgca cccgtggcca ggacccaacg ctgcccgaga   2940
tgcgccgcgt gcggctgctg gagatggcgg acgcgatgga tatgttctgc caagggttgg   3000
tttgcgcatt cacagttctc cgcaagaatt gattggctcc aattcttgga gtggtgaatc   3060
cgttagcgag gtgccgccgg cttccattca ggtcgaggtg gcccggctcc atgcaccgcg   3120
acgcaacgcg gggaggcaga caaggtatag ggcggcgcct acaatccatg ccaacccgtt   3180
ccatgtgctc gccgaggcgg cataaatcgc cgtgacgatc agcggtccag tgatcgaagt   3240
taggctggta agagccgcga gcgatccttg aagctgtccc tgatggtcgt catctacctg   3300
cctggacagc atggcctgca acgcgggcat cccgatgccg ccggaagcga gaagaatcat   3360
aatggggaag gccatccagc ctcgcgtcgc gaacgccagc aagacgtagc ccagcgcgtc   3420
ggccgccatg ccgcgataa tggcctgctt ctcgccgaaa cgtttggtgg cgggaccagt   3480
gacgaaggct tgagcgaggg cgtgcaagat tccgaatacc gcaagcgaca ggccgatcat   3540
cgtcgcgctc cagcgaaagc ggtcctcgcc gaaaatgacc cagagcgctg ccggcacctg   3600
tcctacgagt tgcatgataa agaagacagt cataagtgcg gcgacgatag tcatgccccg   3660
cgcccaccgg aaggagctga ctgggttgaa ggctctcaag ggcatcggtc gagatcccgg   3720
tgcctaatga gtgagctaac ttacattaat tgcgttgcgc tcactgcccg ctttccagtc   3780
gggaaacctg tcgtgccagc tgcattaatg aatcggccaa cgcgcgggga gaggcggttt   3840
gcgtattggg cgccagggtg ttttttcttt tcaccagtga cgggcaac agctgattgc   3900
ccttcaccgc ctggccctga gagagttgca gcaagcggtc cacgctggtt tgccccagca   3960
ggcgaaaatc ctgtttgatg gtggttaacg gcgggatata acatgagctg tcttcggtat   4020
cgtcgtatcc cactaccgag atatccgcac caacgcgcag cccggactcg gtaatggcgc   4080
gcattgcgcc cagcgccatc tgatcgttgg caaccagcat cgcagtggga acgatgccct   4140
cattcagcat ttgcatggtt tgttgaaaac cggacatggc actccagtcg ccttcccgtt   4200
ccgctatcgg ctgaatttga ttgcgagtga gatatttatg ccagccagcc agacgcagac   4260
gcgccgagac agaacttaat gggcccgcta acagcgcgat ttgctggtga cccaatgcga   4320
ccagatgctc cacgcccagt cgcgtaccgt cttcatggga gaaataata ctgttgatgg   4380
gtgtctggtc agagacatca agaaataacg ccggaacatt agtgcaggca gcttccacag   4440
caatggcatc ctggtcatcc agcggatagt taatgatcag cccactgacg cgttgcgcga   4500
gaagattgtg caccgccgct ttacaggctt cgacgccgct tcgttctacc atcgacacca   4560
ccacgctggc acccagttga tcggcgcgag atttaatcgc cgcgacaatt tgcgacggcg   4620
cgtgcagggc cagactggag gtggcaacgc caatcagcaa cgactgtttg cccgccagtt   4680
gttgtgccac gcggttggga atgtaattca gctccgccat cgccgcttcc acttttttccc   4740
gcgttttcgc agaaacgtgg ctggcctggt tcaccacgcg ggaaacggtc tgataagaga   4800
caccggcata ctctgcgaca tcgtataacg ttactggttt cacattcacc ccctgaattt   4860
gactctcttc cgggcgctat catgccatac cgcgaaaggt tttgcgccat cgatggtgt   4920
ccgggatctc gacgctctcc cttatgcgac tcctgcatta ggaagcagcc cagtagtagg   4980
ttgaggccgt tgagcaccgc cgccgcaagg aatggtgcat gcaaggagat ggcgcccaac   5040
agtcccccgg ccacggggcc tgccaccata cccacgccga aacaagcgct catgagcccg   5100
aagtggcgag cccgatcttc cccatcggtg atgtcgcga tataggcgcc agcaaccgca   5160
cctgtggcgc cggtgatgcc ggccacgatg cgtccggcgt agaggatcga gatctcgatc   5220
```

-continued

```
ccgcgaaatt aatacgactc actatagggg aattgtgagc ggataacaat tcccctctag   5280
aaataatttt gtttaacttt aagaaggaga tataccatgg gcagcagcca tcatcatcat   5340
catcacagca gcggcctggt gccgcgcggc agccatatgc gtaaaatgac catgattacg   5400
gattcactgg ccgtcgtttt acaacgtcgt gactgggaaa accctggcgt tacccaactt   5460
aatcgccttg cagcacatcc cccttccgcc agctggcgta atagcgaaga ggcccgcacc   5520
gatcgccctt cccaacagtt gcgcagcctg aatggcgaat ggcgctttgc ctggtttccg   5580
gcaccagaag cggtgccgga aagctggctg gagtgcgatc ttcctgaggc cgatactgtc   5640
gtcgtcccct caaactggca gatgcacggt tacgatgcgc ccatctacac caacgtgacc   5700
tatcccatta cggtcaatcc gccgtttgtt cccacggaga atccgacggg ttgttactcg   5760
ctcacattta atgttgatga aagctggcta caggaaggcc agacgcgaat tattttgat   5820 ggcgttaact cggcgtttca tctgtggtgc aacgggcgct gggtcggtta cggccaggac   5880
agtcgtttgc cgtctgaatt tgacctgagc gcattttac gcgccggaga aaaccgcctc   5940
gcggtgatgg tgctgcgctg gagtgacggc agttatctgg aagatcagga tatgtggcgg   6000
atgagcggca ttttccgtga cgtctcgttg ctgcataaac cgactacaca aatcagcgat   6060
ttccatgttg ccactcgctt taatgatgat ttcagccgcg ctgtactgga ggctgaagtt   6120
cagatgtgcg gcgagttgcg tgactaccta cgggtaacag tttctttatg gcagggtgaa   6180
acgcaggtcg ccagcggcac cgcgcctttc ggcggtgaaa ttatcgatga gcgtggtggt   6240
tatgccgatc gcgtcacact acgtctgaac gtcgaaaacc cgaaactgtg gagcgccgaa   6300
atcccgaatc tctatcgtgc ggtggttgaa ctgcacaccg ccgacggcac gctgattgaa   6360
gcagaagcct gcgatgtcgg tttccgcgag gtgcggattg aaaatggtct gctgctgctg   6420
aacggcaagc cgttgctgat tcgaggcgtt aaccgtcacg agcatcatcc tctgcatggt   6480
caggtcatgg atgagcagac gatggtgcag gatatcctgc tgatgaagca gaacaacttt   6540
aacgccgtgc gctgttcgca ttatccgaac catccgctgt ggtacacgct gtgcgaccgc   6600
tacggcctgt atgtggtgga tgaagccaat attgaaaccc acggcatggt gccaatgaat   6660
cgtctgaccg atgatccgcg ctggctaccg gcgatgagcg aacgcgtaac gcgaatggtg   6720
cagcgcgatc gtaatcaccc gagtgtgatc atctggtcgc tggggaatga atcaggccac   6780
ggcgctaatc acgacgcgct gtatcgctgg atcaaatctg tcgatccttc ccgcccggtg   6840
cagtatgaag gcggcggagc cgacaccacg gccaccgata ttatttgccc gatgtacgcg   6900
cgcgtggatg aagaccagcc cttcccggct gtgccgaaat ggtccatcaa aaaatggctt   6960
tcgctacctg gagagacgcg cccgctgatc ctttgcgaat acgcccacgc gatgggtaac   7020
agtcttggcg gtttcgctaa atactggcag gcgtttcgtc agtatccccg tttacagggc   7080
ggcttcgtct gggactgggt ggatcagtcg ctgattaaat atgatgaaaa cggcaacccg   7140
tggtcggctt acggcggtga ttttggcgat acgccgaacg atcgccagtt ctgtatgaac   7200
ggtctggtct ttgccgaccg cacgccgcat ccagcgctga cggaagcaaa acaccagcag   7260
cagtttttcc agttccgttt atccgggcaa accatcgaag tgaccagcga atacctgttc   7320
cgtcatagcg ataacgagct cctgcactgg atggtggcgc tggatggtaa gccgctggca   7380
agcggtgaag tgcctctgga tgtcgctcca caaggtaaac agttgattga actgcctgaa   7440
ctaccgcagc cggagagcgc cgggcaactc tggctcacag tacgcgtagt gcaaccgaac   7500
gcgaccgcat ggtcagaagc cgggcacatc agcgcctggc agcagtggcg tctggcggaa   7560
aacctcagtg tgacgctccc cgccgcgtcc cacgccatcc cgcatctgac caccagcgaa   7620
```

```
atggattttt gcatcgagct gggtaataag cgttggcaat ttaaccgcca gtcaggcttt      7680
ctttcacaga tgtggattgg cgataaaaaa caactgctga cgccgctgcg cgatcagttc      7740
acccgtgcac cgctggataa cgacattggc gtaagtgaag cgacccgcat tgaccctaac      7800
gcctgggtcg aacgctggaa ggcggcgggc cattaccagg ccgaagcagc gttgttgcag      7860
tgcacggcag atacacttgc tgatgcggtg ctgattacga ccgctcacgc gtggcagcat      7920
caggggaaaa ccttatttat cagccggaaa acctaccgga ttgatggtag tggtcaaatg      7980
gcgattaccg ttgatgttga agtggcgagc gatacaccgc atccggcgcg gattggcctg      8040
aactgccagc tggcgcaggt agcagagcgg gtaaactggc tcggattagg ccgcaagaa       8100 aactatcccg accgccttac tgccgcctgt tttgaccgct gggatctgcc attgtcagac      8160
atgtataccc cgtacgtctt cccgagcgaa aacggtctgc gctgcgggac gcgcgaattg      8220
aattatggcc acaccagtg gcgcggcgac ttccagttca acatcagccg ctacagtcaa       8280
cagcaactga tggaaaccag ccatcgccat ctgctgcacg cggaagaagg cacatggctg      8340
aatatcgacg gtttccatat ggggattggt ggcgacgact cctggagccc gtcagtatcg      8400
gcggaattcc agctgagcgc cggtcgctac cattaccagt tggtctggtg tcaaaaataa      8460
ctagcataac cccttggggc ctctaaatag cataaccccct tggggcctct aaacgggtct     8520
tgaggggttt tttgctgaaa ggaggaacta tatccggata tcccgcaaga ggcccggcag     8580
taccggcata ccaagccta tgcctacagc atccagggtg acggtgccga ggatgacgat       8640
gagcgcattg ttagatttca tacacggtgc ctgactgcgt tagcaattta actgtgataa      8700
actaccgcat taaagcttat cgatgataag ctgtcaaaca tgagaa                      8746

<210> SEQ ID NO 70
<211> LENGTH: 3554
<212> TYPE: DNA
<213> ORGANISM: Artificial Sequence
<220> FEATURE:
<223> OTHER INFORMATION: synthetic

<400> SEQUENCE: 70
ctagtaaatt cgcgtttcta cggtagccgg gcgctaatac gactcactat agggtctgat        60
gggtccgcag ccaacctcgt cccagaggtc ggactttaga acagaggaga taaagatgga      120
cctctgggaa acctggcggc agcgcaagaa gatgaccatg attacggatt cactggccgt      180
cgttttacaa cgtcgtgact gggaaaaccc tggcgttacc caacttaatc gccttgcagc     240
acatccccct ttcgccagct ggcgtaatag cgaagaggcc cgcaccgatc gcccttccca     300
acagttgcgc agcctgaatg gcgaatggta ataatagcat aaccccttgg ggcctctaaa     360
cgggtcttga ggggtttttt gctgaaacct caggcatttg agaagcacac ggtcacactg     420
cttccggtag tcaataaacc ggtaaaccag caatagacat aagcggctat ttaacgaccc      480 tgcccctgaac cgacgacaag ctgacgaccg ggtctccgca agtggcactt tcggggaaa     540 tgtgcgcgga acccctattt gtttatttt ctaaatacat tcaaatatgt atccgctcat       600
gaattaattc ttagaaaaac tcatcgagca tcaaatgaaa ctgcaattta ttcatatcag     660
gattatcaat accatatttt tgaaaagcc gtttctgtaa tgaaggagaa aactcaccga      720
ggcagttcca taggatggca agatcctggt atcggtctgc gattccgact cgtccaacat     780
caatacaacc tattaatttc ccctcgtcaa aaataaggtt atcaagtgag aaatcaccat     840
gagtgacgac tgaatccggt gagaatggca aaagtttatg catttctttc cagacttgtt     900
```

```
caacaggcca gccattacgc tcgtcatcaa atcactcgc atcaaccaaa ccgttattca      960
ttcgtgattg cgcctgagcg agacgaaata cgcggtcgct gttaaaagga caattacaaa     1020
caggaatcga atgcaaccgg cgcaggaaca ctgccagcgc atcaacaata ttttcacctg     1080
aatcaggata ttcttctaat acctggaatg ctgttttccc ggggatcgca gtggtgagta     1140
accatgcatc atcaggagta cggataaaat gcttgatggt cggaagaggc ataaattccg     1200
tcagccagtt tagtctgacc atctcatctg taacatcatt ggcaacgcta cctttgccat     1260
gtttcagaaa caactctggc gcatcgggct tcccatacaa tcgatagatt gtcgcacctg     1320
attgcccgac attatcgcga gcccatttat acccatataa atcagcatcc atgttggaat     1380
ttaatcgcgg cctagagcaa gacgtttccc gttgaatatg gctcatactc ttcctttttc     1440
aatattattg aagcatttat cagggttatt gtctcatgag cggatacata tttgaatgta     1500
tttagaaaaa taaacaaata ggcatgctag cgcagaaacg tcctagaaga tgccaggagg     1560
atacttagca gagagacaat aaggccggag cgaagccgtt tttccatagg ctccgccccc     1620
ctgacgaaca tcacgaaatc tgacgctcaa atcagtggtg gcgaaacccg acaggactat     1680
aaagatacca ggcgtttccc cctgatggct ccctcttgcg ctctcctgtt cccgtcctgc     1740
ggcgtccgtg ttgtggtgga ggcttttaccc aaatcaccac gtcccgttcc gtgtagacag     1800
ttcgctccaa gctgggctgt gtgcaagaac ccccgttca gcccgactgc tgcgccttat      1860
ccggtaacta tcatcttgag tccaacccgg aaagacacga caaaacgcca ctggcagcag     1920
ccattggtaa ctgagaatta gtggatttag atatcgagag tcttgaagtg gtggcctaac     1980
agaggctaca ctgaaaggac agtatttggt atctgcgctc cactaaagcc agttaccagg     2040
ttaagcagtt ccccaactga cttaaccttc gatcaaaccg cctccccagg cggttttttc     2100
gtttacagag caggagatta cgacgatcgt aaaaggatct caagaagatc ctttacggat     2160
tcccgacacc atcactctag atttcagtgc aatttatctc ttcaaatgta gcacctgaag     2220
tcagccccat acgatataag ttgtaattct catgttagtc atgccccgcg cccaccggaa     2280
ggagctgact gggttgaagg ctctcaaggg catcggtcga gatcccggtg cctaatgagt     2340
gagctaactt acattaattg cgttgcgctc actgcccgct ttccagtcgg gaaacctgtc     2400
gtgccagctg cattaatgaa tcggccaacg cgcggggaga ggcggtttgc gtattgggcg     2460
ccagggtggt ttttcttttc accagtgaga cgggcaacag ctgattgccc ttcaccgcct     2520
ggccctgaga gagttgcagc aagcggtcca cgctggtttg ccccagcagg cgaaaatcct     2580
gtttgatggt ggttaacggc gggatataac atgagctgtc ttcggtatcg tcgtatccca     2640
ctaccgagat gtccgcacca acgcgcagcc cggactcggt aatggcgcgc attgcgccca     2700
gcgccatctg atcgttggca accagcatcg cagtgggaac gatgccctca ttcagcattt     2760
gcatggtttg ttgaaaaccg gacatggcac tccagtcgcc ttcccgttcc gctatcggct     2820
gaatttgatt gcgagtgaga tatttatgcc agccagccag acgcagacgc gccgagacag     2880
aacttaatgg gcccgctaac agcgcgattt gctggtgacc caatgcgacc agatgctcca     2940
cgcccagtcg cgtaccgtct tcatgggaga aaataatact gttgatgggt gtctggtcag     3000
agacatcaag aaataacgcc ggaacattag tgcaggcagc ttccacagca atggcatcct     3060
ggtcatccag cggatagtta atgatcagcc cactgacgcg ttgcgcgaga agattgtgca     3120
ccgccgcttt acaggcttcg acgccgcttc gttctaccat cgacaccacc acgctggcac     3180
ccagttgatc ggcgcgagat ttaatcgccg cgacaatttg cgacgcgcg tgcagggcca      3240
gactggaggt ggcaacgcca atcagcaacg actgtttgcc cgccagttgt tgtgccacgc     3300
```

```
ggttgggaat gtaattcagc tccgccatcg ccgcttccac ttttccccgc gttttcgcag    3360
aaacgtggct ggcctggttc accacgcggg aaacggtctg ataagagaca ccggcatact    3420
ctgcgacatc gtataacgtt actggtttca cattcaccac cctgaattga ctctcttccg    3480
ggcgctatca tgccataccg cgaaaggttt tgcgccattc gatggtgtcc gggatctcga    3540
cgctctccct tatg                                                      3554
```

<210> SEQ ID NO 71
<211> LENGTH: 6445
<212> TYPE: DNA
<213> ORGANISM: Artificial Sequence
<220> FEATURE:
<223> OTHER INFORMATION: synthetic

<400> SEQUENCE: 71

```
ctagtaaatt cgcgtttcta cggtagccgg gcgctaatac gactcactat agggtgggag      60
ggcgatcgca atctggctcc cagttttgtg gactttagaa cagaggagat aaagatgaca     120
aaactgggaa cctggcggca gcgcaagaag atgaccatga ttacggattc actggccgtc     180
gttttacaac gtcgtgactg gaaaaaccct ggcgttaccc aacttaatcg ccttgcagca     240 catcccccctt tcgccagctg gcgtaatagc gaagaggccc gcaccgatcg cccttcccaa     300
cagttgcgca gcctgaatgg cgaatggcgc tttgcctggt ttccggcacc agaagcggtg     360
ccggaaagct ggctggagtg cgatcttcct gaggccgata ctgtcgtcgt cccctcaaac     420
tggcagatgc acggttacga tgcgcccatc tacaccaacg tgacctatcc cattacggtc     480
aatccgccgt ttgttcccac ggagaatccg acgggttgtt actcgctcac atttaatgtt     540
gatgaaagct ggctacagga aggccagacg cgaattattt ttgatggcgt taactcggcg     600
tttcatctgt ggtgcaacgg gcgctgggtc ggttacggcc aggacagtcg tttgccgtct     660
gaatttgacc tgagcgcatt tttacgcgcc ggagaaaacc gcctcgcggt gatggtgctg     720
cgctggagtg acggcagtta ctggaagat caggatatgt ggcggatgag cggcattttc     780
cgtgacgtct cgttgctgca taaaccgact acacaaatca gcgatttcca tgttgccact     840
cgctttaatg atgatttcag ccgcgctgta ctggaggctg aagttcagat gtgcggcgag     900
ttgcgtgact acctacgggt aacagtttct ttatggcagg gtgaaacgca ggtcgccagc     960
ggcaccgcgc ctttcggcgg tgaaattatc gatgagcgtg tggttatgc cgatcgcgtc    1020 acactacgtc tgaacgtcga aaacccgaaa ctgtggagcg ccgaaatccc gaatctctat    1080
cgtgcggtgg ttgaactgca caccgccgac ggcacgctga ttgaagcaga agcctgcgat    1140
gtcggtttcc gcgaggtgcg gattgaaaat ggtctgctgc tgctgaacgg caagccgttg    1200
ctgattcgag gcgttaaccg tcacgagcat catcctctgc atggtcaggt catggatgag    1260
cagacgatgg tgcaggatat cctgctgatg aagcagaaca actttaacgc cgtgcgctgt    1320
tcgcattatc cgaaccatcc gctgtggtac acgctgtgcg accgctacgg cctgtatgtg    1380
gtggatgaag ccaatattga aacccacggc atggtgccaa tgaatcgtct gaccgatgat    1440
ccgcgctggc taccggcgat gagcgaacgc gtaacgcgaa tggtgcagcg cgatcgtaat    1500
cacccgagtg tgatcatctg gtcgctgggg aatgaatcag gccacggcgc taatcacgac    1560
gcgctgtatc gctggatcaa atctgtcgat ccttcccgcc cggtgcagta tgaaggcggc    1620
ggagccgaca ccacgccac cgatattatt tgcccgatgt acgcgcgcgt ggatgaagac    1680
cagcccttcc cggctgtgcc gaaatggtcc atcaaaaaat ggctttcgct acctggagag    1740
```

```
acgcgcccgc tgatcctttg cgaatacgcc cacgcgatgg gtaacagtct ggcggtttc    1800 gctaaatact ggcaggcgtt tcgtcagtat ccccgtttac agggcggctt cgtctgggac    1860
tgggtggatc agtcgctgat taaatatgat gaaaacggca acccgtggtc ggcttacggc    1920
ggtgattttg gcgatacgcc gaacgatcgc cagttctgta tgaacggtct ggtcttttgcc   1980 gaccgcacgc cgcatccagc gctgacggaa gcaaaacacc agcagcagtt tttccagttc    2040
cgtttatccg ggcaaaccat cgaagtgacc agcgaatacc tgttccgtca tagcgataac    2100
gagctcctgc actggatggt ggcgctggat ggtaagccgc tggcaagcgg tgaagtgcct    2160
ctggatgtcg ctccacaagg taaacagttg attgaactgc tgaactacc gcagccggag     2220 agcgccgggc aactctggct cacagtacgc gtagtgcaac cgaacgcgac cgcatggtca    2280
gaagccgggc acatcagcgc ctggcagcag tggcgtctgg cggaaaacct cagtgtgacg    2340
ctccccgccg cgtcccacgc catcccgcat ctgaccacca gcgaaatgga ttttttgcatc   2400 gagctgggta ataagcgttg gcaatttaac cgccagtcag gctttctttc acagatgtgg    2460
attggcgata aaaacaact gctgacgccg ctgcgcgatc agttcacccg tgcaccgctg     2520
gataacgaca ttggcgtaag tgaagcgacc cgcattgacc ctaacgcctg ggtcgaacgc    2580
tggaaggcgg cgggccatta ccaggccgaa gcagcgttgt tgcagtgcac ggcagataca    2640
cttgctgatg cggtgctgat tacgaccgct cacgcgtggc agcatcaggg gaaaaccta    2700 tttatcagcc ggaaaaccta ccggattgat ggtagtggtc aaatggcgat taccgttgat   2760
gttgaagtgg cgagcgatac accgcatccg gcgcggattg gcctgaactg ccagctggcg   2820
caggtagcag agcgggtaaa ctggctcgga ttagggccgc aagaaaacta tcccgaccgc   2880
cttactgccg cctgttttga ccgctgggat ctgccattgt cagacatgta taccccgtac   2940
gtcttcccga gcgaaaacgg tctgcgctgc gggacgcgcg aattgaatta tggcccacac   3000
cagtggcgcg cgacttcca gttcaacatc agccgctaca gtcaacagca actgatggaa    3060
accagccatc gccatctgct gcacgcgaaa gaaggcacat ggctgaatat cgacggtttc   3120
catatgggga ttggtggcga cgactcctgg agcccgtcag tatcggcgga attccagctg   3180
agcgccggtc gctaccatta ccagttggtc tggtgtcaaa aataatagca taacccctg    3240 gggcctctaa acgggtcttg aggggttttt tgctgaaacc tcaggcattt gagaagcaca   3300
cggtcacact gcttccggta gtcaataaac cggtaaacca gcaatagaca taagcggcta   3360
tttaacgacc ctgccctgaa ccgacgacaa gctgacgacc gggtctccgc aagtggcact   3420
tttcggggaa atgtgcgcgg aacccctatt tgtttatttt tctaaataca ttcaaatatg   3480
tatccgctca tgaattaatt cttagaaaaa ctcatcgagc atcaaatgaa actgcaattt   3540
attcatatca ggattatcaa taccatattt ttgaaaagc cgtttctgta atgaaggaga   3600
aaactcaccg aggcagttcc ataggatggc aagatcctgg tatcggtctg cgattccgac   3660
tcgtccaaca tcaatacaac ctattaattt cccctcgtca aaataaggt tatcaagtga   3720 gaaatcacca tgagtgacga ctgaatccgg tgagaatggc aaaagtttat gcatttcttt   3780
ccagacttgt tcaacaggcc agccattacg ctcgtcatca aaatcactcg catcaaccaa   3840
accgttattc attcgtgatt gcgcctgagc gagacgaaat acgcggtcgc tgttaaaagg   3900
acaattacaa acaggaatcg aatgcaaccg gcgcaggaac actgccagcg catcaacaat   3960
attttcacct gaatcaggat attcttctaa tacctggaat gctgttttcc cggggatcgc   4020
agtggtgagt aaccatgcat catcaggagt acgataaaa tgcttgatgg tcggaagagg   4080
cataaattcc gtcagccagt ttagtctgac catctcatct gtaacatcat tggcaacgct   4140
```

```
accctttgcca tgtttcagaa acaactctgg cgcatcgggc ttcccataca atcgatagat    4200
tgtcgcacct gattgcccga cattatcgcg agcccattta tacccatata aatcagcatc    4260
catgttggaa tttaatcgcg gcctagagca agacgtttcc cgttgaatat ggctcatact    4320
cttccttttt caatattatt gaagcattta tcagggttat tgtctcatga gcggatacat    4380
atttgaatgt atttagaaaa ataaacaaat aggcatgcta gcgcagaaac gtcctagaag    4440
atgccaggag gatacttagc agagagacaa taaggccgga gcgaagccgt ttttccatag    4500
gctccgcccc cctgacgaac atcacgaaat ctgacgctca aatcagtggt ggcgaaaccc    4560
gacaggacta taaagatacc aggcgtttcc ccctgatggc tccctcttgc gctctcctgt    4620
tcccgtcctg cggcgtccgt gttgtggtgg aggctttacc caaatcacca cgtcccgttc    4680
cgtgtagaca gttcgctcca agctgggctg tgtgcaagaa ccccccgttc agcccgactg    4740
ctgcgcctta tccggtaact atcatcttga gtccaacccg gaaagacacg acaaaacgcc    4800
actggcagca gccattggta actgagaatt agtggattta gatatcgaga gtcttgaagt    4860
ggtggcctaa cagaggctac actgaaagga cagtatttgg tatctgcgct ccactaaagc    4920
cagttaccag gttaagcagt tccccaactg acttaaccct cgatcaaacc gcctccccag    4980
gcggtttttt cgtttacaga gcaggagatt acgacgatcg taaaaggatc tcaagaagat    5040
cctttacgga ttcccgacac catcactcta gatttcagtg caatttatct cttcaaatgt    5100
agcacctgaa gtcagcccca tacgatataa gttgtaattc tcatgttagt catgccccgc    5160
gcccaccgga aggagctgac tgggttgaag gctctcaagg gcatcggtcg agatcccggt    5220
gcctaatgag tgagctaact tacattaatt gcgttgcgct cactgcccgc tttccagtcg    5280
ggaaacctgt cgtgccagct gcattaatga atcggccaac gcgcggggag aggcggtttg    5340
cgtattgggc gccagggtgg ttttcttttt caccagtgag acgggcaaca gctgattgcc    5400
cttcaccgcc tggccctgag agagttgcag caagcggtcc acgctggttt gccccagcag    5460
gcgaaaatcc tgtttgatgg tggttaacgg cgggatataa catgagctgt cttcggtatc    5520
gtcgtatccc actaccgaga tgtccgcacc aacgcgcagc ccggactcgg taatggcgcg    5580
cattgcgccc agcgccatct gatcgttggc aaccagcatc gcagtgggaa cgatgccctc    5640
attcagcatt tgcatggttt gttgaaaacc ggacatggca ctccagtcgc cttcccgttc    5700
cgctatcggc tgaatttgat tgcgagtgag atatttatgc cagccagcca gacgcagacg    5760
cgccgagaca gaacttaatg ggcccgctaa cagcgcgatt tgctggtgac ccaatgcgac    5820
cagatgctcc acgcccagtc gcgtaccgtc ttcatgggag aaaataatac tgttgatggg    5880
tgtctggtca gagacatcaa gaaataacgc cggaacatta gtgcaggcag cttccacagc    5940
aatggcatcc tggtcatcca gcggatagtt aatgatcagc ccactgacgc gttgcgcgag    6000
aagattgtgc accgccgctt tacaggcttc gacgccgctt cgttctacca tcgacaccac    6060
cacgctggca cccagttgat cggcgcgaga tttaatcgcc gcgacaattt gcgacggcgc    6120
gtgcagggcc agactggagg tggcaacgcc aatcagcaac gactgtttgc ccgccagttg    6180
ttgtgccacg cggttgggaa tgtaattcag ctccgccatc gccgcttcca cttttccccg    6240
cgttttcgca gaaacgtggc tggcctggtt caccacgcgg gaaacggtct gataagagac    6300
accggcatac tctgcgacat cgtataacgt tactggtttc acattcacca ccctgaattg    6360
actctcttcc gggcgctatc atgccatacc gcgaaaggtt ttgcgccatt cgatggtgtc    6420
cgggatctcg acgctctccc ttatg                                          6445
```

<210> SEQ ID NO 72
<211> LENGTH: 3553
<212> TYPE: DNA
<213> ORGANISM: Artificial Sequence
<220> FEATURE:
<223> OTHER INFORMATION: synthetic

<400> SEQUENCE: 72

| | | | | | |
|---|---|---|---|---|---|
| ctagtaaatt | cgcgtttcta | cggtagccgg | gcgctaatac | gactcactat | agggtgggag | 60 |
| ggcgatcgca | atctggctcc | cagttttgtg | gactttagaa | cagaggagat | aaagatgaca | 120 |
| aaactgggaa | cctggcggca | gcgcaagaag | atgaccatga | ttacggattc | actggccgtc | 180 |
| gttttacaac | gtcgtgactg | ggaaaaccct | ggcgttaccc | aacttaatcg | ccttgcagca | 240 |
| catcccctt | tcgccagctg | gcgtaatagc | gaagaggccc | gcaccgatcg | cccttcccaa | 300 |
| cagttgcgca | gcctgaatgg | cgaatggtaa | taatagcata | accccttggg | gcctctaaac | 360 |
| gggtcttgag | gggttttttg | ctgaaacctc | aggcatttga | gaagcacacg | gtcacactgc | 420 |
| ttccggtagt | caataaaccg | gtaaaccagc | aatagacata | agcggctatt | taacgaccct | 480 |
| gccctgaacc | gacgacaagc | tgacgaccgg | gtctccgcaa | gtggcacttt | tcggggaaat | 540 |
| gtgcgcggaa | cccctatttg | tttatttttc | taaatacatt | caaatatgta | tccgctcatg | 600 |
| aattaattct | tagaaaaact | catcgagcat | caaatgaaac | tgcaatttat | tcatatcagg | 660 |
| attatcaata | ccatattttt | gaaaaagccg | tttctgtaat | gaaggagaaa | actcaccgag | 720 |
| gcagttccat | aggatggcaa | gatcctggta | tcggtctgcg | attccgactc | gtccaacatc | 780 |
| aatacaacct | attaatttcc | cctcgtcaaa | aataaggtta | tcaagtgaga | aatcaccatg | 840 |
| agtgacgact | gaatccggtg | agaatggcaa | aagtttatgc | atttctttcc | agacttgttc | 900 |
| aacaggccag | ccattacgct | cgtcatcaaa | atcactcgca | tcaaccaaac | cgttattcat | 960 |
| tcgtgattgc | gcctgagcga | gacgaaatac | gcggtcgctg | ttaaaaggac | aattacaaac | 1020 |
| aggaatcgaa | tgcaaccggc | gcaggaacac | tgccagcgca | tcaacaatat | tttcacctga | 1080 |
| atcaggatat | tcttctaata | cctggaatgc | tgttttcccg | gggatcgcag | tggtgagtaa | 1140 |
| ccatgcatca | tcaggagtac | ggataaaatg | cttgatggtc | ggaagaggca | taaattccgt | 1200 |
| cagccagttt | agtctgacca | tctcatctgt | aacatcattg | gcaacgctac | ctttgccatg | 1260 |
| tttcagaaac | aactctggcg | catcgggctt | cccatacaat | cgatagattg | tcgcacctga | 1320 |
| ttgcccgaca | ttatcgcgag | cccatttata | cccatataaa | tcagcatcca | tgttggaatt | 1380 |
| taatcgcggc | ctagagcaag | acgtttcccg | ttgaatatgg | ctcatactct | tcctttttca | 1440 |
| atattattga | agcatttatc | agggttattg | tctcatgagc | ggatacatat | ttgaatgtat | 1500 |
| ttagaaaaat | aaacaaatag | gcatgctagc | gcagaaacgt | cctagaagat | gccaggagga | 1560 |
| tacttagcag | agagacaata | aggccggagc | gaagccgttt | ttccataggc | tccgcccccc | 1620 |
| tgacgaacat | cacgaaatct | gacgctcaaa | tcagtggtgg | cgaaacccga | caggactata | 1680 |
| aagataccag | gcgtttcccc | ctgatggctc | cctcttgcgc | tctcctgttc | ccgtcctgcg | 1740 |
| gcgtccgtgt | tgtggtggag | gctttaccca | aatcaccacg | tcccgttccg | tgtagacagt | 1800 |
| tcgctccaag | ctgggctgtg | tgcaagaacc | ccccgttcag | cccgactgct | gcgccttatc | 1860 |
| cggtaactat | catcttgagt | ccaacccgga | agacacgac | aaaacgccac | tggcagcagc | 1920 |
| cattggtaac | tgagaattag | tggatttaga | tatcgagagt | cttgaagtgg | tggcctaaca | 1980 |
| gaggctacac | tgaaaggaca | gtatttggta | tctgcgctcc | actaaagcca | gttaccaggt | 2040 |
| taagcagttc | cccaactgac | ttaaccttcg | atcaaaccgc | ctccccaggc | ggttttttcg | 2100 |

```
tttacagagc aggagattac gacgatcgta aaaggatctc aagaagatcc tttacggatt    2160
cccgacacca tcactctaga tttcagtgca atttatctct tcaaatgtag cacctgaagt    2220
cagccccata cgatataagt tgtaattctc atgttagtca tgccccgcgc ccaccggaag    2280
gagctgactg ggttgaaggc tctcaagggc atcggtcgag atcccggtgc ctaatgagtg    2340
agctaactta cattaattgc gttgcgctca ctgcccgctt tccagtcggg aaacctgtcg    2400
tgccagctgc attaatgaat cggccaacgc gcggggagag gcggtttgcg tattgggcgc    2460
cagggtggtt tttcttttca ccagtgagac gggcaacagc tgattgccct tcaccgcctg    2520
gccctgagag agttgcagca agcggtccac gctggtttgc cccagcaggc gaaaatcctg    2580
tttgatggtg gttaacggcg ggatataaca tgagctgtct tcggtatcgt cgtatcccac    2640
taccgagatg tccgcaccaa cgcgcagccc ggactcggta tggcgcgca ttgcgcccag    2700 cgccatctga tcgttggcaa ccagcatcgc agtgggaacg atgccctcat tcagcatttg    2760
catggtttgt tgaaaaccgg acatggcact ccagtcgcct tcccgttccg ctatcggctg    2820
aatttgattg cgagtgagat atttatgcca gccagccaga cgcagacgcg ccgagacaga    2880
acttaatggg cccgctaaca gcgcgatttg ctggtgaccc aatgcgacca gatgctccac    2940
gcccagtcgc gtaccgtctt catgggagaa ataatactg ttgatgggtg tctggtcaga    3000
gacatcaaga ataacgccg gaacattagt gcaggcagct tccacagcaa tggcatcctg    3060
gtcatccagc ggatagttaa tgatcagccc actgacgcgt tgcgcgagaa gattgtgcac    3120
cgccgcttta caggcttcga cgccgcttcg ttctaccatc gacaccacca cgctggcacc    3180
cagttgatcg gcgcgagatt taatcgccgc gacaatttgc gacggcgcgt gcagggccag    3240
actggaggtg gcaacgccaa tcagcaacga ctgtttgccc gccagttgtt gtgccacgcg    3300
gttgggaatg taattcagct ccgccatcgc cgcttccact ttttcccgcg ttttcgcaga    3360
aacgtggctg gcctggttca ccacgcggga aacggtctga taagagacac cggcatactc    3420
tgcgacatcg tataacgtta ctggtttcac attcaccacc ctgaattgac tctcttccgg    3480
gcgctatcat gccataccgc gaaaggtttt gcgccattcg atggtgtccg ggatctcgac    3540
gctctccctt atg                                                      3553

<210> SEQ ID NO 73
<211> LENGTH: 3554
<212> TYPE: DNA
<213> ORGANISM: Artificial Sequence
<220> FEATURE:
<223> OTHER INFORMATION: synthetic

<400> SEQUENCE: 73
ctagtaaatt cgcgtttcta cggtagccgg gcgctaatac gactcactat agggtgtgaa      60
tgaagatggc gtcgaatgac gccaacccat ggactttaga acagaggaga taaagatgat     120
gggttggcga acctggcggc agcgcaagaa gatgaccatg attacggatt cactggccgt     180
cgttttacaa cgtcgtgact gggaaaaccc tggcgttacc caacttaatc gccttgcagc     240
acatccccct ttcgccagct ggcgtaatag cgaagaggcc cgcaccgatc gcccttccca     300
acagttcgcg agcctgaatg gcgaatggta ataatagcat aaccccttgg ggcctctaaa     360
cgggtcttga ggggtttttt gctgaaacct caggcatttg agaagcacac ggtcacactg     420
cttccggtag tcaataaacc ggtaaaccag caatagacat aagcggctat ttaacgaccc     480
tgccctgaac cgacgacaag ctgacgaccg ggtctccgca agtggcactt tcggggaaa      540
```

```
tgtgcgcgga acccctattt gtttattttt ctaaatacat tcaaatatgt atccgctcat    600
gaattaattc ttagaaaaac tcatcgagca tcaaatgaaa ctgcaattta ttcatatcag    660
gattatcaat accatatttt tgaaaaagcc gtttctgtaa tgaaggagaa aactcaccga    720
ggcagttcca taggatggca agatcctggt atcggtctgc gattccgact cgtccaacat    780
caatacaacc tattaatttc ccctcgtcaa aaataaggtt atcaagtgag aaatcaccat    840
gagtgacgac tgaatccggt gagaatggca aaagtttatg catttctttc cagacttgtt    900
caacaggcca gccattacgc tcgtcatcaa aatcactcgc atcaaccaaa ccgttattca    960
ttcgtgattg cgcctgagcg agacgaaata cgcggtcgct gttaaaagga caattacaaa   1020
caggaatcga atgcaaccgg cgcaggaaca ctgccagcgc atcaacaata ttttcacctg   1080
aatcaggata ttcttctaat acctggaatg ctgttttccc ggggatcgca gtggtgagta   1140
accatgcatc atcaggagta cggataaaat gcttgatggt cggaagaggc ataaattccg   1200
tcagccagtt tagtctgacc atctcatctg taacatcatt ggcaacgcta cctttgccat   1260
gtttcagaaa caactctggc gcatcgggct tcccatacaa tcgatagatt gtcgcacctg   1320
attgcccgac attatcgcga gcccatttat acccatataa atcagcatcc atgttggaat   1380
ttaatcgcgg cctagagcaa gacgtttccc gttgaatatg gctcatactc ttccttttc    1440
aatattattg aagcatttat cagggttatt gtctcatgag cggatacata tttgaatgta   1500
tttagaaaaa taaacaaata ggcatgctag cgcagaaacg tcctagaaga tgccaggagg   1560
atacttagca gagagacaat aaggccggag cgaagccgtt tttccatagg ctccgccccc   1620
ctgacgaaca tcacgaaatc tgacgctcaa atcagtggtg cgaaacccg acaggactat    1680
aaagatacca ggcgtttccc cctgatggct ccctcttgcg ctctcctgtt cccgtcctgc   1740
ggcgtccgtg ttgtggtgga ggctttaccc aaatcaccac gtcccgttcc gtgtagacag   1800
ttcgctccaa gctgggctgt gtgcaagaac cccccgttca gcccgactgc tgcgccttat   1860
ccggtaacta tcatcttgag tccaacccgg aaagacacga caaaacgcca ctggcagcag   1920
ccattggtaa ctgagaatta gtggatttag atatcgagag tcttgaagtg gtggcctaac   1980
agaggctaca ctgaaaggac agtatttggt atctgcgctc cactaaagcc agttaccagg   2040
ttaagcagtt ccccaactga cttaaccttc gatcaaaccg cctccccagg cggttttttc   2100
gtttacagag caggagatta cgacgatcgt aaaaggatct caagaagatc ctttacggat   2160
tcccgacacc atcactctag atttcagtgc aatttatctc ttcaaatgta gcacctgaag   2220
tcagccccat acgatataag ttgtaattct catgttagtc atgccccgcg cccaccggaa   2280
ggagctgact gggttgaagg ctctcaaggg catcggtcga gatcccggtg cctaatgagt   2340
gagctaactt acattaattg cgttgcgctc actgcccgct ttccagtcgg gaaacctgtc   2400
gtgccagctg cattaatgaa tcggccaacg cgcgggagaa ggcggtttgc gtattgggcg   2460
ccagggtggt ttttcttttc accagtgaga cgggcaacag ctgattgccc ttcaccgcct   2520
ggccctgaga gagttgcagc aagcggtcca cgctggtttg cccagcagg cgaaaatcct    2580
gtttgatggt ggttaacggc gggatataac atgagctgtc ttcggtatcg tcgtatccca   2640
ctaccgagat gtccgcacca acgcgcagcc cggactcggt aatggcgcgc attgcgccca   2700
gcgccatctg atcgttggca accagcatcg cagtgggaac gatgccctca ttcagcattt   2760
gcatggtttg ttgaaaaccg gacatggcac tccagtcgcc ttcccgttcc gctatcggct   2820
gaatttgatt gcgagtgaga tatttatgcc agccagccag acgcagacgc gccgagacag   2880
aacttaatgg gcccgctaac agcgcgattt gctggtgacc caatgcgacc agatgctcca   2940
```

```
cgcccagtcg cgtaccgtct tcatgggaga aaataatact gttgatgggt gtctggtcag    3000
agacatcaag aaataacgcc ggaacattag tgcaggcagc ttccacagca atggcatcct    3060
ggtcatccag cggatagtta atgatcagcc cactgacgcg ttgcgcgaga agattgtgca    3120
ccgccgcttt acaggcttcg acgccgcttc gttctaccat cgacaccacc acgctggcac    3180
ccagttgatc ggcgcgagat taatcgccg cgacaatttg cgacggcgcg tgcagggcca    3240
gactggaggt ggcaacgcca atcagcaacg actgtttgcc cgccagttgt tgtgccacgc    3300
ggttgggaat gtaattcagc tccgccatcg ccgcttccac ttttcccgc gttttcgcag    3360 aaacgtggct ggcctggttc accacgcggg aaacggtctg ataagagaca ccggcatact    3420
ctgcgacatc gtataacgtt actggtttca cattcaccac cctgaattga ctctcttccg    3480
ggcgctatca tgcctaccg cgaaaggttt tgcgccattc gatggtgtcc gggatctcga    3540
cgctctccct tatg                                                      3554
```

<210> SEQ ID NO 74
<211> LENGTH: 3554
<212> TYPE: DNA
<213> ORGANISM: Artificial Sequence
<220> FEATURE:
<223> OTHER INFORMATION: synthetic

<400> SEQUENCE: 74

```
ctagtaaatt cgcgtttcta cggtagccgg gcgctaatac gactcactat agggagatct     60
gagcacgtgg gagggcgatc gcaatctggc ggactttaga acagaggaga taaagatggc    120
cagattgcga acctggcggc agcgcaagaa gatgaccatg attacggatt cactggccgt    180
cgttttacaa cgtcgtgact gggaaaaccc tggcgttacc caacttaatc gccttgcagc    240
acatccccct ttcgccagct ggcgtaatag cgaagaggcc cgcaccgatc gcccttccca    300
acagttgcgc agcctgaatg gcgaatggta ataatagcat aacccttgg ggcctctaaa    360 cgggtcttga ggggttttt gctgaaacct caggcatttg agaagcacac ggtcacactg    420
cttccggtag tcaataaacc ggtaaaccag caatagacat aagcggctat ttaacgaccc    480 tgcccctgaac cgacgacaag ctgacgaccg ggtctccgca agtggcactt tcggggaaa    540 tgtgcgcgga accctatt gtttattttt ctaaatacat tcaaatatgt atccgctcat    600
gaattaattc ttagaaaaac tcatcgagca tcaaatgaaa ctgcaattta ttcatatcag    660
gattatcaat accatatttt tgaaaaagcc gtttctgtaa tgaaggagaa aactcaccga    720
ggcagttcca taggatggca agatcctggt atcggtctgc gattccgact cgtccaacat    780
caatacaacc tattaatttc ccctcgtcaa aaataaggtt atcaagtgag aaatcaccat    840
gagtgacgac tgaatccgt gagaatggca aaagtttatg catttctttc cagacttgtt    900
caacaggcca gccattacgc tcgtcatcaa atcactcgc atcaaccaaa ccgttattca    960
ttcgtgattg cgcctgagcg agacgaaata cgcggtcgct gttaaaagga caattacaaa   1020
caggaatcga atgcaaccgg cgcaggaaca ctgccagcgc atcaacaata ttttcacctg   1080
aatcaggata ttcttctaat acctggaatg ctgttttccc ggggatcgca gtggtgagta   1140
accatgcatc atcaggagta cggataaaat gcttgatggt cggaagaggc ataaattccg   1200
tcagccagtt tagtctgacc atctcatctg taacatcatt ggcaacgcta cctttgccat   1260
gtttcagaaa caactctggc gcatcgggct tcccatacaa tcgatagatt gtcgcacctg   1320
attgcccgac attatcgcga gcccatttat acccatataa atcagcatcc atgttggaat   1380
```

```
ttaatcgcgg cctagagcaa gacgtttccc gttgaatatg gctcatactc ttccttttc      1440
aatattattg aagcatttat cagggttatt gtctcatgag cggatacata tttgaatgta      1500
tttagaaaaa taaacaaata ggcatgctag cgcagaaacg tcctagaaga tgccaggagg      1560
atacttagca gagagacaat aaggccggag cgaagccgtt tttccatagg ctccgccccc      1620
ctgacgaaca tcacgaaatc tgacgctcaa atcagtggtg gcgaaacccg acaggactat      1680
aaagatacca ggcgtttccc cctgatggct ccctcttgcg ctctcctgtt cccgtcctgc      1740
ggcgtccgtg ttgtggtgga ggctttaccc aaatcaccac gtcccgttcc gtgtagacag      1800
ttcgctccaa gctgggctgt gtgcaagaac ccccgttca gcccgactgc tgcgccttat       1860
ccggtaacta tcatcttgag tccaacccgg aaagacacga caaaacgcca ctggcagcag      1920
ccattggtaa ctgagaatta gtggatttag atatcgagag tcttgaagtg gtggcctaac      1980
agaggctaca ctgaaaggac agtatttggt atctgcgctc cactaaagcc agttaccagg      2040
ttaagcagtt ccccaactga cttaaccttc gatcaaaccg cctccccagg cggttttttc      2100
gtttacagag caggagatta cgacgatcgt aaaaggatct caagaagatc ctttacggat      2160
tcccgacacc atcactctag atttcagtgc aatttatctc ttcaaatgta gcacctgaag      2220
tcagccccat acgatataag ttgtaattct catgttagtc atgccccgcg cccaccggaa      2280
ggagctgact gggttgaagg ctctcaaggg catcggtcga gatcccggtg cctaatgagt      2340
gagctaactt acattaattg cgttgcgctc actgcccgct ttccagtcgg gaaacctgtc      2400
gtgccagctg cattaatgaa tcggccaacg cgcggggaga ggcggtttgc gtattgggcg      2460
ccagggtggt ttttcttttc accagtgaga cgggcaacag ctgattgccc ttcaccgcct      2520
ggccctgaga gagttgcagc aagcggtcca cgctggtttg ccccagcagg cgaaaatcct      2580
gtttgatggt ggttaacggc gggatataac atgagctgtc ttcggtatcg tcgtatccca      2640
ctaccgagat gtccgcacca acgcgcagcc cggactcggt aatggcgcgc attgcgccca      2700
gcgccatctg atcgttggca accagcatcg cagtgggaac gatgccctca ttcagcattt      2760
gcatggtttg ttgaaaaccg gacatggcac tccagtcgcc ttcccgttcc gctatcggct      2820
gaatttgatt gcgagtgaga tatttatgcc agccagccag acgcagacgc gccgagacag      2880
aacttaatgg gcccgctaac agcgcgattt gctggtgacc caatgcgacc agatgctcca      2940
cgcccagtcg cgtaccgtct tcatgggaga aaataatact gttgatgggt gtctggtcag      3000
agacatcaag aaataacgcc ggaacattag tgcaggcagc ttccacagca atggcatcct      3060
ggtcatccag cggatagtta atgatcagcc cactgacgcg ttgcgcgaga agattgtgca      3120
ccgccgcttt acaggcttcg acgccgcttc gttctaccat cgacaccacc acgctggcac      3180
ccagttgatc ggcgcgagat ttaatcgccg cgacaatttg cgacggcgcg tgcagggcca      3240
gactggaggt ggcaacgcca atcagcaacg actgtttgcc cgccagttgt tgtgccacgc      3300
ggttgggaat gtaattcagc tccgccatcg ccgcttccac ttttccgc gttttcgcag      3360
aaacgtggct ggcctggttc accacgcggg aaacggtctg ataagagaca ccggcatact      3420
ctgcgacatc gtataacgtt actggtttca cattcaccac cctgaattga ctctcttccg      3480
ggcgctatca tgccataccg cgaaaggttt tgcgccattc gatggtgtcc gggatctcga      3540
cgctctccct tatg                                                        3554

<210> SEQ ID NO 75
<211> LENGTH: 3554
<212> TYPE: DNA
<213> ORGANISM: Artificial Sequence
```

<220> FEATURE:
<223> OTHER INFORMATION: synthetic

<400> SEQUENCE: 75

```
ctagtaaatt cgcgtttcta cggtagccgg gcgctaatac gactcactat agggatcgca      60
atctggctcc cagtttttgtg aatgaagatg ggactttaga acagaggaga taaagatgca    120
tcttcattca acctggcggc agcgcaagaa gatgaccatg attacggatt cactggccgt    180
cgttttacaa cgtcgtgact gggaaaaccc tggcgttacc caacttaatc gccttgcagc    240
acatccccct ttcgccagct ggcgtaatag cgaagaggcc cgcaccgatc gcccttccca    300
acagttgcgc agcctgaatg gcgaatggta ataatagcat aacccttgg ggcctctaaa     360
cgggtcttga ggggtttttt gctgaaacct caggcatttg agaagcacac ggtcacactg    420
cttccggtag tcaataaacc ggtaaaccag caatagacat aagcggctat ttaacgaccc    480
tgccctgaac cgacgacaag ctgacgaccg ggtctccgca agtggcactt tcggggaaa     540
tgtgcgcgga accccatttt gtttattttt ctaaatacat tcaaatatgt atccgctcat    600
gaattaattc ttagaaaaac tcatcgagca tcaaatgaaa ctgcaattta ttcatatcag    660
gattatcaat accatatttt tgaaaaagcc gtttctgtaa tgaaggagaa aactcaccga    720
ggcagttcca taggatggca agatcctggt atcggtctgc gattccgact cgtccaacat    780
caatacaacc tattaatttc ccctcgtcaa aaataaggtt atcaagtgag aaatcaccat    840
gagtgacgac tgaatccggt gagaatggca aaagtttatg catttctttc cagacttgtt    900
caacaggcca gccattacgc tcgtcatcaa aatcactcgc atcaaccaaa ccgttattca    960
ttcgtgattg cgcctgagcg agacgaaata cgcggtcgct gttaaaagga caattacaaa   1020
caggaatcga atgcaaccgg cgcaggaaca ctgccagcgc atcaacaata ttttcacctg   1080
aatcaggata ttcttctaat acctggaatg ctgttttccc ggggatcgca gtggtgagta   1140
accatgcatc atcaggagta cggataaaat gcttgatggt cggaagaggc ataaattccg   1200
tcagccagtt tagtctgacc atctcatctg taacatcatt ggcaacgcta cctttgccat   1260
gtttcagaaa caactctggc gcatcgggct tcccatacaa tcgatagatt gtcgcacctg   1320
attgcccgac attatcgcga gcccatttat acccatataa atcagcatcc atgttggaat   1380
ttaatcgcgg cctagagcaa gacgtttccc gttgaatatg gctcatactc ttcctttttc   1440
aatattattg aagcatttat cagggttatt gtctcatgag cggatacata tttgaatgta   1500
tttagaaaaa taaacaaata ggcatgctag cgcagaaacg tcctagaaga tgccaggagg   1560
atacttagca gagagacaat aaggccggag cgaagccgtt tttccatagg ctccgccccc   1620
ctgacgaaca tcacgaaatc tgacgctcaa atcagtggtg gcgaaacccg acaggactat   1680
aaagatacca ggcgtttccc cctgatggct ccctcttgcg ctctcctgtt cccgtcctgc   1740
ggcgtccgtg ttgtggtgga ggctttaccc aaatcaccac gtcccgttcc gtgtagacag   1800
ttcgctccaa gctgggctgt gtgcaagaac ccccgttca gcccgactgc tgcgccttat    1860
ccggtaacta tcatcttgag tccaacccgg aaagacacga caaaacgcca ctggcagcag   1920
ccattggtaa ctgagaatta gtggatttag atatcgagag tcttgaagtg gtggcctaac   1980
agaggctaca ctgaaaggac agtatttggt atctgcgctc cactaaagcc agttaccagg   2040
ttaagcagtt ccccaactga cttaaccttc gatcaaaccg cctccccagg cggttttttc   2100
gtttacagag caggagatta cgacgatcgt aaaaggatct caagaagatc ctttacggat   2160
tcccgacacc atcactctag atttcagtgc aatttatctc ttcaaatgta gcacctgaag   2220
```

```
tcagccccat acgatataag ttgtaattct catgttagtc atgccccgcg cccaccggaa    2280
ggagctgact gggttgaagg ctctcaaggg catcggtcga gatcccggtg cctaatgagt    2340
gagctaactt acattaattg cgttgcgctc actgcccgct ttccagtcgg gaaacctgtc    2400
gtgccagctg cattaatgaa tcggccaacg cgcggggaga ggcggtttgc gtattgggcg    2460
ccagggtggt ttttcttttc accagtgaga cgggcaacag ctgattgccc ttcaccgcct    2520
ggccctgaga gagttgcagc aagcggtcca cgctggtttg ccccagcagg cgaaaatcct    2580
gtttgatggt ggttaacggc gggatataac atgagctgtc ttcggtatcg tcgtatccca    2640
ctaccgagat gtccgcacca acgcgcagcc cggactcggt aatggcgcgc attgcgccca    2700
gcgccatctg atcgttggca accagcatcg cagtgggaac gatgccctca ttcagcattt    2760
gcatggtttg ttgaaaaccg gacatggcac tccagtcgcc ttcccgttcc gctatcggct    2820
gaatttgatt gcgagtgaga tatttatgcc agccagccag acgcagacgc gccgagacag    2880
aacttaatgg gcccgctaac agcgcgattt gctggtgacc caatgcgacc agatgctcca    2940
cgcccagtcg cgtaccgtct tcatgggaga aaataatact gttgatgggt gtctggtcag    3000
agacatcaag aaataacgcc ggaacattag tgcaggcagc ttccacagca atggcatcct    3060
ggtcatccag cggatagtta atgatcagcc cactgacgcg ttgcgcgaga agattgtgca    3120
ccgccgcttt acaggcttcg acgccgcttc gttctaccat cgacaccacc acgctggcac    3180
ccagttgatc ggcgcgagat ttaatcgccg cgacaatttg cgacggcgcg tgcagggcca    3240
gactggaggt ggcaacgcca atcagcaacg actgtttgcc cgccagttgt tgtgccacgc    3300
ggttgggaat gtaattcagc tccgccatcg ccgcttccac tttttcccgc gttttcgcag    3360
aaacgtggct ggcctggttc accacgcggg aaacggtctg ataagagaca ccggcatact    3420
ctgcgacatc gtataacgtt actggtttca cattcaccac cctgaattga ctctcttccg    3480
ggcgctatca tgccataccg cgaaaggttt tgcgccattc gatggtgtcc gggatctcga    3540
cgctctccct tatg                                                      3554

<210> SEQ ID NO 76
<211> LENGTH: 3554
<212> TYPE: DNA
<213> ORGANISM: Artificial Sequence
<220> FEATURE:
<223> OTHER INFORMATION: synthetic

<400> SEQUENCE: 76
ctagtaaatt cgcgtttcta cggtagccgg gcgctaatac gactcactat agggtcgaat      60
gacgccaacc catctgatgg gtccgcagcc ggactttaga acagaggaga taaagatggg     120
ctgcggacca acctggcggc agcgcaagaa gatgaccatg attacggatt cactggccgt     180
cgttttacaa cgtcgtgact gggaaaaccc tggcgttacc caacttaatc gccttgcagc     240
acatccccct ttcgccagct ggcgtaatag cgaagaggcc cgcaccgatc gcccttccca     300
acagttgcgc agcctgaatg gcgaatggta ataatagcat aaccccttgg ggcctctaaa     360
cgggtcttga ggggtttttt gctgaaacct caggcatttg agaagcacac ggtcacactg     420
cttccggtag tcaataaacc ggtaaaccag caatagacat aagcggctat ttaacgaccc     480
tgccctgaac cgacgacaag ctgacgaccg gtctccgcaa agtggcactt tcggggaaa      540
tgtgcgcgga acccctattt gtttattttt ctaaatacat tcaaatatgt atccgctcat     600
gaattaattc ttagaaaaac tcatcgagca tcaaatgaaa ctgcaattta ttcatatcag     660
gattatcaat accatatttt tgaaaaagcc gtttctgtaa tgaaggagaa aactcaccga     720
```

```
ggcagttcca taggatggca agatcctggt atcggtctgc gattccgact cgtccaacat    780
caatacaacc tattaatttc ccctcgtcaa aataaggtt atcaagtgag aaatcaccat     840
gagtgacgac tgaatccggt gagaatggca aaagtttatg catttctttc cagacttgtt   900
caacaggcca gccattacgc tcgtcatcaa aatcactcgc atcaaccaaa ccgttattca    960
ttcgtgattg cgcctgagcg agacgaaata cgcggtcgct gttaaaagga caattacaaa  1020
caggaatcga atgcaaccgg cgcaggaaca ctgccagcgc atcaacaata ttttcacctg  1080
aatcaggata ttcttctaat acctggaatg ctgttttccc ggggatcgca gtggtgagta  1140
accatgcatc atcaggagta cggataaaat gcttgatggt cggaagaggc ataaattccg  1200
tcagccagtt tagtctgacc atctcatctg taacatcatt ggcaacgcta cctttgccat  1260
gtttcagaaa caactctggc gcatcgggct tcccatacaa tcgatagatt gtcgcacctg  1320
attgcccgac attatcgcga gcccatttat acccatataa atcagcatcc atgttggaat  1380
ttaatcgcgg cctagagcaa gacgtttccc gttgaatatg gctcatactc ttcctttttc  1440
aatattattg aagcatttat cagggttatt gtctcatgag cggatacata tttgaatgta  1500
tttagaaaaa taaacaaata ggcatgctag cgcagaaacg tcctagaaga tgccaggagg  1560
atacttagca gagagacaat aaggccggag cgaagccgtt tttccatagg ctccgccccc  1620
ctgacgaaca tcacgaaatc tgacgctcaa atcagtggtg gcgaaacccg acaggactat  1680
aaagatacca ggcgtttccc cctgatggct ccctcttgcg ctctcctgtt cccgtcctgc  1740
ggcgtccgtg ttgtggtgga ggctttaccc aaatcaccac gtcccgttcc gtgtagacag  1800
ttcgctccaa gctgggctgt gtgcaagaac cccccgttca gcccgactgc tgcgccttat  1860
ccggtaacta tcatcttgag tccaacccgg aaagacacga caaaacgcca ctggcagcag  1920
ccattggtaa ctgagaatta gtggatttag atatcgagag tcttgaagtg gtggcctaac  1980
agaggctaca ctgaaaggac agtatttggt atctgcgctc cactaaagcc agttaccagg  2040
ttaagcagtt ccccaactga cttaaccttc gatcaaaccg cctccccagg cggttttttc  2100
gtttacagag caggagatta cgacgatcgt aaaaggatct caagaagatc ctttacggat  2160
tcccgacacc atcactctag atttcagtgc aatttatctc ttcaaatgta gcacctgaag  2220
tcagccccat acgatataag ttgtaattct catgttagtc atgccccgcg cccaccggaa  2280
ggagctgact gggttgaagg ctctcaaggg catcggtcga gatcccggtg cctaatgagt  2340
gagctaactt acattaattg cgttgcgctc actgcccgct ttccagtcgg gaaacctgtc  2400
gtgccagctg cattaatgaa tcggccaacg cgcggggaga gcggtttgc gtattgggcg  2460 ccagggtggt ttttcttttc accagtgaga cgggcaacag ctgattgccc ttcaccgcct  2520
ggccctgaga gagttgcagc aagcggtcca cgctggtttg cccagcagg cgaaaatcct  2580 gtttgatggt ggttaacggc gggatataac atgagctgtc ttcggtatcg tcgtatccca  2640
ctaccgagat gtccgcacca acgcgcagcc cggactcgt aatggcgcgc attgcgccca  2700
gcgccatctg atcgttggca accagcatcg cagtgggaac gatgccctca ttcagcattt  2760
gcatggtttg ttgaaaaccg gacatggcac tccagtcgcc ttcccgttcc gctatcggct  2820
gaatttgatt gcgagtgaga tatttatgcc agccagccag acgcagacgc gccgagacag  2880
aacttaatgg gcccgctaac agcgcgattt gctggtgacc caatgcgacc agatgctcca  2940
cgcccagtcg cgtaccgtct tcatgggaga aataatact gttgatgggt gtctggtcag  3000
agacatcaag aaataacgcc ggaacattag tgcaggcagc ttccacagca atggcatcct  3060
```

```
ggtcatccag cggatagtta atgatcagcc cactgacgcg ttgcgcgaga agattgtgca      3120
ccgccgcttt acaggcttcg acgccgcttc gttctaccat cgacaccacc acgctggcac      3180
ccagttgatc ggcgcgagat ttaatcgccg cgacaatttg cgacggcgcg tgcagggcca      3240
gactggaggt ggcaacgcca atcagcaacg actgtttgcc cgccagttgt tgtgccacgc      3300
ggttgggaat gtaattcagc tccgccatcg ccgcttccac ttttttcccgc gttttcgcag      3360 aaacgtggct ggcctggttc accacgcggg aaacggtctg ataagagaca ccggcatact      3420
ctgcgacatc gtataacgtt actggtttca cattcaccac cctgaattga ctctcttccg      3480
ggcgctatca tgccataccg cgaaaggttt tgcgccattc gatggtgtcc gggatctcga      3540
cgctctccct tatg                                                        3554

<210> SEQ ID NO 77
<211> LENGTH: 3554
<212> TYPE: DNA
<213> ORGANISM: Artificial Sequence
<220> FEATURE:
<223> OTHER INFORMATION: synthetic

<400> SEQUENCE: 77
ctagtaaatt cgcgtttcta cggtagccgg gcgctaatac gactcactat agggccatct        60
tcattcacaa aactgggagc cagattgcga ggactttaga acagaggaga taaagatgtc       120
gcaatctgga acctggcggc agcgcaagaa gatgaccatg attacggatt cactggccgt       180
cgttttacaa cgtcgtgact gggaaaaccc tggcgttacc caacttaatc gccttgcagc       240
acatccccct ttcgccagct ggcgtaatag cgaagaggcc cgcaccgatc gcccttccca       300
acagttgcgc agcctgaatg gcgaatggta ataatagcat aaccccttgg ggcctctaaa       360
cgggtcttga ggggttttt gctgaaacct caggcatttg agaagcacac ggtcacactg       420
cttccggtag tcaataaacc ggtaaaccag caatagacat aagcggctat ttaacgaccc       480
tgccctgaac cgacgacaag ctgacgaccg gtctccgca agtggcactt tcggggaaa       540 tgtgcgcgga acccctattt gtttattttt ctaaatacat tcaaatatgt atccgctcat       600
gaattaattc ttagaaaaac tcatcgagca tcaaatgaaa ctgcaattta ttcatatcag       660
gattatcaat accatatttt tgaaaaagcc gtttctgtaa tgaaggagaa aactcaccga       720
ggcagttcca taggatggca agatcctggt atcggtctgc gattccgact cgtccaacat       780
caatacaacc tattaatttc ccctcgtcaa aaataaggtt atcaagtgag aaatcaccat       840
gagtgacgac tgaatccggt gagaatggca aaagtttatg catttctttc cagacttgtt       900
caacaggcca gccattacgc tcgtcatcaa aatcactcgc atcaaccaaa ccgttattca       960
ttcgtgattg cgcctgagcg agacgaaata cgcggtcgct gttaaaagga caattacaaa      1020
caggaatcga atgcaaccgg cgcaggaaca ctgccagcgc atcaacaata ttttcacctg      1080
aatcaggata ttcttctaat acctggaatg ctgtttttcc ggggatcgca gtggtgagta      1140
accatgcatc atcaggagta cggataaaat gcttgatggt cggaagaggc ataaattccg      1200
tcagccagtt tagtctgacc atctcatctg taacatcatt ggcaacgcta cctttgccat      1260
gtttcagaaa caactctggc gcatcgggct tcccatacaa tcgatagatt gtcgcacctg      1320
attgcccgac attatcgcga gcccatttat acccatataa atcagcatcc atgttggaat      1380
ttaatcgcgg cctagagcaa gacgtttccc gttgaatatg gctcatactc ttcctttttc      1440
aatattattg aagcatttat cagggttatt gtctcatgag cggatacata tttgaatgta      1500
tttagaaaaa taaacaaata ggcatgctag cgcagaaacg tcctagaaga tgccaggagg      1560
```

```
atacttagca gagagacaat aaggccggag cgaagccgtt tttccatagg ctccgccccc   1620
ctgacgaaca tcacgaaatc tgacgctcaa atcagtggtg gcgaaacccg acaggactat   1680
aaagatacca ggcgtttccc cctgatggct ccctcttgcg ctctcctgtt cccgtcctgc   1740
ggcgtccgtg ttgtggtgga ggctttaccc aaatcaccac gtcccgttcc gtgtagacag   1800
ttcgctccaa gctgggctgt gtgcaagaac ccccgttca gcccgactgc tgcgccttat    1860
ccggtaacta tcatcttgag tccaacccgg aaagacacga caaaacgcca ctggcagcag   1920
ccattggtaa ctgagaatta gtggatttag atatcgagag tcttgaagtg gtggcctaac   1980
agaggctaca ctgaaaggac agtatttggt atctgcgctc cactaaagcc agttaccagg   2040
ttaagcagtt ccccaactga cttaaccttc gatcaaaccg cctccccagg cggttttttc   2100
gtttacagag caggagatta cgacgatcgt aaaaggatct caagaagatc ctttacggat   2160
tcccgacacc atcactctag atttcagtgc aatttatctc ttcaaatgta gcacctgaag   2220
tcagccccat acgatataag ttgtaattct catgttagtc atgccccgcg cccaccggaa   2280
ggagctgact gggttgaagg ctctcaaggg catcggtcga gatcccggtg cctaatgagt   2340
gagctaactt acattaattg cgttgcgctc actgcccgct ttccagtcgg gaaacctgtc   2400
gtgccagctg cattaatgaa tcggccaacg cgcggggaga ggcggtttgc gtattgggcg   2460
ccagggtggt ttttcttttc accagtgaga cgggcaacag ctgattgccc ttcaccgcct   2520
ggccctgaga gagttgcagc aagcggtcca cgctggtttg cccagcagg cgaaaatcct    2580 gtttgatggt ggttaacggc gggatataac atgagctgtc ttcggtatcg tcgtatccca   2640
ctaccgagat gtccgcacca acgcgcagcc cggactcggt aatggcgcgc attgcgccca   2700
gcgccatctg atcgttggca accagcatcg cagtgggaac gatgccctca ttcagcattt   2760
gcatggtttg ttgaaaaccg gacatggcac tccagtcgcc ttcccgttcc gctatcggct   2820
gaatttgatt gcgagtgaga tatttatgcc agccagccag acgcagacgc gccgagacag   2880
aacttaatgg gcccgctaac agcgcgattt gctggtgacc caatgcgacc agatgctcca   2940
cgcccagtcg cgtaccgtct tcatgggaga aaataatact gttgatgggt gtctggtcag   3000
agacatcaag aaataacgcc ggaacattag tgcaggcagc ttccacagca atggcatcct   3060
ggtcatccag cggatagtta atgatcagcc cactgacgcg ttgcgcgaga agattgtgca   3120
ccgccgcttt acaggcttcg acgccgcttc gttctaccat cgacaccacc acgctggcac   3180
ccagttgatc ggcgcgagat ttaatcgccg cgacaatttg cgacggcgcg tgcagggcca   3240
gactggaggt ggcaacgcca atcagcaacg actgtttgcc cgccagttgt tgtgccacgc   3300
ggttgggaat gtaattcagc tccgccatcg ccgcttccac tttttcccgc gttttcgcag   3360
aaacgtggct ggcctggttc accacgcggg aaacggtctg ataagagaca ccggcatact   3420
ctgcgacatc gtataacgtt actggtttca cattcaccac cctgaattga ctctcttccg   3480
ggcgctatca tgccataccg cgaaaggttt tgcgccattc gatggtgtcc gggatctcga   3540
cgctctccct tatg                                                    3554
```

<210> SEQ ID NO 78
<211> LENGTH: 3554
<212> TYPE: DNA
<213> ORGANISM: Artificial Sequence
<220> FEATURE:
<223> OTHER INFORMATION: synthetic

<400> SEQUENCE: 78

```
ctagtaaatt cgcgtttcta cggtagccgg gcgctaatac gactcactat agggatcgcc    60
ctcccacgtg ctcagatctg agaatctcat ggactttaga acagaggaga taaagatgat   120
gagattctca acctggcggc agcgcaagaa gatgaccatg attacggatt cactggccgt   180
cgttttacaa cgtcgtgact gggaaaaccc tggcgttacc caacttaatc gccttgcagc   240
acatccccct ttcgccagct ggcgtaatag cgaagaggcc cgcaccgatc gcccttccca   300
acagttgcgc agcctgaatg gcgaatggta ataatagcat aaccccttgg ggcctctaaa   360
cgggtcttga ggggttttt gctgaaacct caggcatttg agaagcacac ggtcacactg    420
cttccggtag tcaataaacc ggtaaaccag caatagacat aagcggctat ttaacgaccc   480
tgccctgaac cgacgacaag ctgacgaccg ggtctccgca agtggcactt tcggggaaa    540 tgtgcgcgga acccctattt gtttatttt ctaaatacat tcaaatatgt atccgctcat    600
gaattaattc ttagaaaaac tcatcgagca tcaaatgaaa ctgcaattta ttcatatcag   660
gattatcaat accatatttt tgaaaagcc gtttctgtaa tgaaggagaa aactcaccga    720
ggcagttcca taggatggca agatcctggt atcggtctgc gattccgact cgtccaacat   780
caatacaacc tattaatttc ccctcgtcaa aaataaggtt atcaagtgag aaatcaccat   840
gagtgacgac tgaatccggt gagaatggca aaagtttatg catttctttc cagacttgtt   900
caacaggcca gccattacgc tcgtcatcaa aatcactcgc atcaaccaaa ccgttattca   960
ttcgtgattg cgcctgagcg agacgaaata cgcggtcgct gttaaaagga caattacaaa  1020
caggaatcga atgcaaccgg cgcaggaaca ctgccagcgc atcaacaata ttttcacctg  1080
aatcaggata ttcttctaat acctggaatg ctgttttccc ggggatcgca gtggtgagta  1140
accatgcatc atcaggagta cggataaaat gcttgatggt cggaagaggc ataaattccg  1200
tcagccagtt tagtctgacc atctcatctg taacatcatt ggcaacgcta cctttgccat  1260
gtttcagaaa caactctggc gcatcgggct tcccatacaa tcgatagatt gtcgcacctg  1320
attgcccgac attatcgcga gcccatttat acccatataa atcagcatcc atgttggaat  1380
ttaatcgcgg cctagagcaa gacgtttccc gttgaatatg gctcatactc ttccttttc   1440 aatattattg aagcatttat cagggttatt gtctcatgag cggatacata tttgaatgta  1500
tttagaaaaa taaacaaata ggcatgctag cgcagaaacg tcctagaaga tgccaggagg  1560
atacttagca gagagacaat aaggccggag cgaagccgtt tttccatagg ctccgccccc  1620
ctgacgaaca tcacgaaatc tgacgctcaa atcagtggtg gcgaaacccg acaggactat  1680
aaagatacca ggcgtttccc cctgatggct ccctcttgcg ctctcctgtt cccgtcctgc  1740
ggcgtccgtg ttgtggtgga ggctttaccc aaatcaccac gtcccgttcc gtgtagacag  1800
ttcgctccaa gctgggctgt gtgcaagaac ccccgttca gcccgactgc tgcgccttat   1860
ccggtaacta tcatcttgag tccaacccgg aaagacacga caaaacgcca ctggcagcag  1920
ccattggtaa ctgagaatta gtggatttag atatcgagag tcttgaagtg gtggcctaac  1980
agaggctaca ctgaaaggac agtatttggt atctgcgctc cactaaagcc agttaccagg  2040
ttaagcagtt ccccaactga cttaaccttc gatcaaaccg cctccccagg cggttttttc  2100
gtttacagag caggagatta cgacgatcgt aaaaggatct caagaagatc ctttacggat  2160
tcccgacacc atcactctag atttcagtgc aatttatctc ttcaaatgta gcacctgaag  2220
tcagccccat acgatataag ttgtaattct catgttagtc atgccccgcg cccaccggaa  2280
ggagctgact gggttgaagg ctctcaaggg catcggtcga gatcccggtg cctaatgagt  2340
gagctaactt acattaattg cgttgcgctc actgcccgct ttccagtcgg gaaacctgtc  2400
```

```
gtgccagctg cattaatgaa tcggccaacg cgcggggaga ggcggtttgc gtattgggcg    2460
ccagggtggt ttttctttc accagtgaga cgggcaacag ctgattgccc ttcaccgcct    2520
ggccctgaga gagttgcagc aagcggtcca cgctggtttg ccccagcagg cgaaaatcct    2580
gtttgatggt ggtaacggc gggatataac atgagctgtc ttcggtatcg tcgtatccca    2640
ctaccgagat gtccgcacca acgcgcagcc cggactcggt aatggcgcgc attgcgccca    2700
gcgccatctg atcgttggca accagcatcg cagtgggaac gatgccctca ttcagcattt    2760
gcatggtttg ttgaaaaccg gacatggcac tccagtcgcc ttcccgttcc gctatcggct    2820
gaatttgatt gcgagtgaga tatttatgcc agccagccag acgcagacgc gccgagacag    2880
aacttaatgg gcccgctaac agcgcgattt gctggtgacc caatgcgacc agatgctcca    2940
cgcccagtcg cgtaccgtct tcatgggaga aaataatact gttgatgggt gtctggtcag    3000
agacatcaag aaataacgcc ggaacattag tgcaggcagc ttccacagca atggcatcct    3060
ggtcatccag cggatagtta atgatcagcc cactgacgcg ttgcgcgaga agattgtgca    3120
ccgccgcttt acaggcttcg acgccgcttc gttctaccat cgacaccacc acgctggcac    3180
ccagttgatc ggcgcgagat ttaatcgccg cgacaatttg cgacggcgcg tgcagggcca    3240
gactggaggt ggcaacgcca atcagcaacg actgtttgcc cgccagttgt tgtgccacgc    3300
ggttgggaat gtaattcagc tccgccatcg ccgcttccac tttttcccgc gttttcgcag    3360
aaacgtggct ggcctggttc accacgcggg aaacggtctg ataagagaca ccggcatact    3420
ctgcgacatc gtataacgtt actggtttca cattcaccac cctgaattga ctctcttccg    3480
ggcgctatca tgccataccg cgaaaggttt tgcgccattc gatggtgtcc gggatctcga    3540
cgctctccct tatg                                                      3554
```

<210> SEQ ID NO 79
<211> LENGTH: 3554
<212> TYPE: DNA
<213> ORGANISM: Artificial Sequence
<220> FEATURE:
<223> OTHER INFORMATION: synthetic

<400> SEQUENCE: 79

```
ctagtaaatt cgcgtttcta cggtagccgg gcgctaatac gactcactat agggacaaaa     60
ctgggagcca gattgcgatc gccctcccac ggactttaga acagaggaga taaagatggt    120
gggagggcga acctggcggc agcgcaagaa gatgaccatg attacggatt cactggccgt    180
cgttttacaa cgtcgtgact gggaaaaccc tggcgttacc caacttaatc gccttgcagc    240
acatccccct ttcgccagct ggcgtaatag cgaagaggcc cgcaccgatc gcccttccca    300
acagttgcgc agcctgaatg gcgaatggta ataatagcat aacccccttgg ggcctctaaa    360 cgggtcttga ggggttttt gctgaaacct caggcatttg agaagcacac ggtcacactg    420
cttccggtag tcaataaacc ggtaaaccag caatagacat aagcggctat taacgaccc    480 tgccctgaac cgacgacaag ctgacgaccg ggtctccgca agtggcactt tcggggaaa    540 tgtgcgcgga accctatt gtttattttt ctaaatacat tcaaatatgt atccgctcat    600
gaattaattc ttagaaaaac tcatcgagca tcaaatgaaa ctgcaattta ttcatatcag    660
gattatcaat accatatttt tgaaaaagcc gtttctgtaa tgaaggagaa aactcaccga    720
ggcagttcca taggatggca agatcctggt atcggtctgc gattccgact cgtccaacat    780
caatacaacc tattaatttc ccctcgtcaa aataaggtt atcaagtgag aaatcaccat    840
```

```
gagtgacgac tgaatccggt gagaatggca aaagtttatg catttctttc cagacttgtt    900
caacaggcca gccattacgc tcgtcatcaa aatcactcgc atcaaccaaa ccgttattca    960
ttcgtgattg cgcctgagcg agacgaaata cgcggtcgct gttaaaagga caattacaaa   1020
caggaatcga atgcaaccgg cgcaggaaca ctgccagcgc atcaacaata ttttcacctg   1080
aatcaggata ttcttctaat acctggaatg ctgttttccc ggggatcgca gtggtgagta   1140
accatgcatc atcaggagta cggataaaat gcttgatggt cggaagaggc ataaattccg   1200
tcagccagtt tagtctgacc atctcatctg taacatcatt ggcaacgcta cctttgccat   1260
gtttcagaaa caactctggc gcatcgggct tcccatacaa tcgatagatt gtcgcacctg   1320
attgcccgac attatcgcga gcccatttat acccatataa atcagcatcc atgttggaat   1380
ttaatcgcgg cctagagcaa gacgtttccc gttgaatatg gctcatactc ttcctttttc   1440
aatattattg aagcatttat cagggttatt gtctcatgag cggatacata tttgaatgta   1500
tttagaaaaa taaacaaata ggcatgctag cgcagaaacg tcctagaaga tgccaggagg   1560
atacttagca gagagacaat aaggccggag cgaagccgtt tttccatagg ctccgccccc   1620
ctgacgaaca tcacgaaatc tgacgctcaa atcagtggtg gcgaaacccg acaggactat   1680
aaagatacca ggcgtttccc cctgatggct ccctcttgcg ctctcctgtt cccgtcctgc   1740
ggcgtccgtg ttgtggtgga ggctttaccc aaatcaccac gtcccgttcc gtgtagacag   1800
ttcgctccaa gctgggctgt gtgcaagaac cccccgttca gcccgactgc tgcgccttat   1860
ccggtaacta tcatcttgag tccaacccgg aaagacacga caaaacgcca ctggcagcag   1920
ccattggtaa ctgagaatta gtggatttag atatcgagag tcttgaagtg gtggcctaac   1980
agaggctaca ctgaaaggac agtatttggt atctgcgctc cactaaagcc agttaccagg   2040
ttaagcagtt ccccaactga cttaaccttc gatcaaaccg cctccccagg cggttttttc   2100
gtttacagag caggagatta cgacgatcgt aaaaggatct caagaagatc ctttacggat   2160
tcccgacacc atcactctag atttcagtgc aatttatctc ttcaaatgta gcacctgaag   2220
tcagccccat acgatataag ttgtaattct catgttagtc atgccccgcg cccaccggaa   2280
ggagctgact gggttgaagg ctctcaaggg catcggtcga gatcccggtg cctaatgagt   2340
gagctaactt acattaattg cgttgcgctc actgcccgct ttccagtcgg gaaacctgtc   2400
gtgccagctg cattaatgaa tcggccaacg cgcggggaga ggcggtttgc gtattgggcg   2460
ccagggtggt ttttctttc accagtgaga cgggcaacag ctgattgccc ttcaccgcct   2520
ggccctgaga gagttgcagc aagcggtcca cgctggtttg ccccagcagg cgaaaatcct   2580
gtttgatggt ggttaacggc gggatataac atgagctgtc ttcggtatcg tcgtatccca   2640
ctaccgagat gtccgcacca cgcgcagcc cggactcgt aatggcgcgc attgcgccca   2700
gcgccatctg atcgttggca accagcatcg cagtgggaac gatgccctca ttcagcattt   2760
gcatggtttg ttgaaaaccg gacatggcac tccagtcgcc ttcccgttcc gctatcggct   2820
gaatttgatt gcgagtgaga tatttatgcc agccagccag acgcagacgc gccgagacag   2880
aacttaatgg gcccgctaac agcgcgattt gctggtgacc caatgcgacc agatgctcca   2940
cgcccagtcg cgtaccgtct tcatgggaga aaataatact gttgatgggt gtctggtcag   3000
agacatcaag aaataacgcc ggaacattag tgcaggcagc ttccacagca atggcatcct   3060
ggtcatccag cggatagtta atgatcagcc cactgacgcg ttgcgcgaga agattgtgca   3120
ccgccgcttt acaggcttcg acgccgcttc gttctaccat cgacaccacc acgctggcac   3180
ccagttgatc ggcgcgagat ttaatcgccg cgacaatttg cgacggcgcg tgcagggcca   3240
```

```
gactggaggt ggcaacgcca atcagcaacg actgtttgcc cgccagttgt tgtgccacgc   3300
ggttgggaat gtaattcagc tccgccatcg ccgcttccac ttttccccgc gttttcgcag   3360
aaacgtggct ggcctggttc accacgcggg aaacggtctg ataagagaca ccggcatact   3420
ctgcgacatc gtataacgtt actggtttca cattcaccac cctgaattga ctctcttccg   3480
ggcgctatca tgccataccg cgaaaggttt tgcgccattc gatggtgtcc gggatctcga   3540
cgctctccct tatg                                                     3554
```

<210> SEQ ID NO 80
<211> LENGTH: 3554
<212> TYPE: DNA
<213> ORGANISM: Artificial Sequence
<220> FEATURE:
<223> OTHER INFORMATION: synthetic

<400> SEQUENCE: 80

```
ctagtaaatt cgcgtttcta cggtagccgg gcgctaatac gactcactat agggctggga     60
cgaggttggc tgcggaccca tcagatgggt ggactttaga acagaggaga taaagatgac    120
ccatctgata acctggcggc agcgcaagaa gatgaccatg attacggatt cactggccgt    180
cgttttacaa cgtcgtgact gggaaaaccc tggcgttacc caacttaatc gccttgcagc    240
acatccccct ttcgccagct ggcgtaatag cgaagaggcc cgcaccgatc gcccttccca    300
acagttgcgc agcctgaatg gcgaatggta ataatagcat aaccccttgg ggcctctaaa    360
cgggtcttga ggggttttt gctgaaacct caggcatttg agaagcacac ggtcacactg     420
cttccggtag tcaataaacc ggtaaaccag caatagacat aagcggctat ttaacgaccc    480
tgccctgaac cgacgacaag ctgacgaccg ggtctccgca agtggcactt tcggggaaa     540 tgtgcgcgga acccctattt gtttattttt ctaaatacat tcaaatatgt atccgctcat    600
gaattaattc ttagaaaaac tcatcgagca tcaaatgaaa ctgcaattta ttcatatcag    660
gattatcaat accatatttt tgaaaaagcc gtttctgtaa tgaaggagaa aactcaccga    720
ggcagttcca taggatggca agatcctggt atcggtctgc gattccgact cgtccaacat    780
caatacaacc tattaatttc ccctcgtcaa aaataaggtt atcaagtgag aaatcaccat    840
gagtgacgac tgaatccggt gagaatggca aaagtttatg catttctttc cagacttgtt    900
caacaggcca gccattacgc tcgtcatcaa atcactcgc atcaaccaaa ccgttattca     960
ttcgtgattg cgcctgagcg agacgaaata cgcggtcgct gttaaaagga caattacaaa   1020
caggaatcga atgcaaccgg cgcaggaaca ctgccagcgc atcaacaata tttttcacctg  1080 aatcaggata ttcttctaat acctggaatg ctgttttccc ggggatcgca gtggtgagta   1140
accatgcatc atcaggagta cggataaaat gcttgatggt cggaagaggc ataaattccg   1200
tcagccagtt tagtctgacc atctcatctg taacatcatt ggcaacgcta cctttgccat   1260
gtttcagaaa caactctggc gcatcgggct tcccatacaa tcgatagatt gtcgcacctg   1320
attgcccgac attatcgcga gcccatttat acccatataa atcagcatcc atgttggaat   1380
ttaatcgcgg cctagagcaa gacgtttccc gttgaatatg gctcatactc ttccttttc    1440 aatattattg aagcatttat cagggttatt gtctcatgag cggatacata tttgaatgta   1500
tttagaaaaa taaacaaata ggcatgctag cgcagaaacg tcctagaaga tgccaggagg   1560
atacttagca gagagacaat aaggccggag cgaagccgtt tttccatagg ctccgccccc   1620
ctgacgaaca tcacgaaatc tgacgctcaa atcagtggtg gcgaaacccg acaggactat   1680
```

| | | | | |
|---|---|---|---|---|
| aaagatacca | ggcgtttccc | cctgatggct | ccctcttgcg | ctctcctgtt | cccgtcctgc | 1740 |
| ggcgtccgtg | ttgtggtgga | ggctttaccc | aaatcaccac | gtcccgttcc | gtgtagacag | 1800 |
| ttcgctccaa | gctgggctgt | gtgcaagaac | ccccgttca | gcccgactgc | tgcgccttat | 1860 |
| ccggtaacta | tcatcttgag | tccaacccgg | aaagacacga | caaaacgcca | ctggcagcag | 1920 |
| ccattggtaa | ctgagaatta | gtggatttag | atatcgagag | tcttgaagtg | gtggcctaac | 1980 |
| agaggctaca | ctgaaaggac | agtatttggt | atctgcgctc | cactaaagcc | agttaccagg | 2040 |
| ttaagcagtt | ccccaactga | cttaaccttc | gatcaaaccg | cctccccagg | cggttttttc | 2100 |
| gtttacagag | caggagatta | cgacgatcgt | aaaaggatct | caagaagatc | ctttacggat | 2160 |
| tcccgacacc | atcactctag | atttcagtgc | aatttatctc | ttcaaatgta | gcacctgaag | 2220 |
| tcagccccat | acgatataag | ttgtaattct | catgttagtc | atgccccgcg | cccaccggaa | 2280 |
| ggagctgact | gggttgaagg | ctctcaaggg | catcggtcga | gatcccggtg | cctaatgagt | 2340 |
| gagctaactt | acattaattg | cgttgcgctc | actgcccgct | ttccagtcgg | gaaacctgtc | 2400 |
| gtgccagctg | cattaatgaa | tcggccaacg | cgcgggaga | ggcggtttgc | gtattgggcg | 2460 |
| ccagggtggt | ttttctttc | accagtgaga | cgggcaacag | ctgattgccc | ttcaccgcct | 2520 |
| ggccctgaga | gagttgcagc | aagcggtcca | cgctggtttg | ccccagcagg | cgaaaatcct | 2580 |
| gtttgatggt | ggttaacggc | gggatataac | atgagctgtc | ttcggtatcg | tcgtatccca | 2640 |
| ctaccgagat | gtccgcacca | acgcgcagcc | cggactcggt | aatggcgcgc | attgcgccca | 2700 |
| gcgccatctg | atcgttggca | accagcatcg | cagtgggaac | gatgccctca | ttcagcattt | 2760 |
| gcatggtttg | ttgaaaaccg | gacatggcac | tccagtcgcc | ttcccgttcc | gctatcggct | 2820 |
| gaatttgatt | gcgagtgaga | tatttatgcc | agccagccag | acgcagacgc | gccgagacag | 2880 |
| aacttaatgg | gcccgctaac | agcgcgattt | gctggtgacc | caatgcgacc | agatgctcca | 2940 |
| cgcccagtcg | cgtaccgtct | tcatgggaga | aaataatact | gttgatgggt | gtctggtcag | 3000 |
| agacatcaag | aaataacgcc | ggaacattag | tgcaggcagc | ttccacagca | atggcatcct | 3060 |
| ggtcatccag | cggatagtta | atgatcagcc | cactgacgcg | ttgcgcgaga | agattgtgca | 3120 |
| ccgccgcttt | acaggcttcg | acgccgcttc | gttctaccat | cgacaccacc | acgctggcac | 3180 |
| ccagttgatc | ggcgcgagat | ttaatcgccg | cgacaatttg | cgacggcgcg | tgcagggcca | 3240 |
| gactggaggt | ggcaacgcca | atcagcaacg | actgtttgcc | cgccagttgt | tgtgccacgc | 3300 |
| ggttgggaat | gtaattcagc | tccgccatcg | ccgcttccac | ttttcccgc | gttttcgcag | 3360 |
| aaacgtggct | ggcctggttc | accacgcggg | aaacggtctg | ataagagaca | ccggcatact | 3420 |
| ctgcgacatc | gtataacgtt | actggtttca | cattcaccac | cctgaattga | ctctcttccg | 3480 |
| ggcgctatca | tgccataccg | cgaaaggttt | tgcgccattc | gatggtgtcc | gggatctcga | 3540 |
| cgctctccct | tatg | | | | | 3554 |

<210> SEQ ID NO 81
<211> LENGTH: 3553
<212> TYPE: DNA
<213> ORGANISM: Artificial Sequence
<220> FEATURE:
<223> OTHER INFORMATION: synthetic

<400> SEQUENCE: 81

| | | | | | | |
|---|---|---|---|---|---|---|
| ctagtaaatt | cgcgtttcta | cggtagccgg | gcgctaatac | gactcactat | agggtcattc | 60 |
| gacgccatct | tcattcacaa | aactgggagg | gactttagaa | cagaggagat | aaagatgctc | 120 |
| ccagttttaa | cctggcggca | gcgcaagaag | atgaccatga | ttacggattc | actggccgtc | 180 |

```
gttttacaac gtcgtgactg ggaaaaccct ggcgttaccc aacttaatcg ccttgcagca      240
catccccctt tcgccagctg gcgtaatagc gaagaggccc gcaccgatcg cccttcccaa      300
cagttgcgca gcctgaatgg cgaatggtaa taatagcata accccttggg gcctctaaac      360
gggtcttgag gggttttttg ctgaaacctc aggcatttga aagcacacg gtcacactgc       420 ttccggtagt caataaaccg gtaaaccagc aatagacata agcggctatt taacgaccct      480
gccctgaacc gacgacaagc tgacgaccgg gtctccgcaa gtggcacttt tcggggaaat      540
gtgcgcggaa cccctatttg tttatttttc taaatacatt caaatatgta tccgctcatg      600
aattaattct tagaaaaact catcgagcat caaatgaaac tgcaatttat tcatatcagg      660
attatcaata ccatattttt gaaaaagccg tttctgtaat gaaggagaaa actcaccgag      720
gcagttccat aggatggcaa gatcctggta tcggtctgcg attccgactc gtccaacatc      780
aatacaacct attaatttcc cctcgtcaaa aataaggtta tcaagtgaga atcaccatg       840 agtgacgact gaatccggtg agaatggcaa aagtttatgc atttctttcc agacttgttc      900
aacaggccag ccattacgct cgtcatcaaa atcactcgca tcaaccaaac cgttattcat      960
tcgtgattgc gcctgagcga gacgaaatac gcggtcgctg ttaaaaggac aattacaaac     1020
aggaatcgaa tgcaaccggc gcaggaacac tgccagcgca tcaacaatat tttcacctga     1080
atcaggatat tcttctaata cctggaatgc tgttttcccg gggatcgcag tggtgagtaa     1140
ccatgcatca tcaggagtac ggataaaatg cttgatggtc ggaagaggca taaattccgt     1200
cagccagttt agtctgacca tctcatctgt aacatcattg gcaacgctac ctttgccatg     1260
tttcagaaac aactctggcg catcgggctt cccatacaat cgatagattg tcgcacctga     1320
ttgcccgaca ttatcgcgag cccatttata cccatataaa tcagcatcca tgttggaatt     1380
taatcgcggc ctagagcaag acgtttcccg ttgaatatgg ctcatactct cctttttca     1440 atattattga agcatttatc agggttattg tctcatgagc ggatacatat ttgaatgtat     1500
ttagaaaaat aaacaaatag gcatgctagc gcagaaacgt cctagaagat gccaggagga     1560
tacttagcag agagacaata aggccggagc gaagccgttt ttccataggc tccgcccccc     1620
tgacgaacat cacgaaatct gacgctcaaa tcagtggtgg cgaaacccga caggactata     1680
aagataccag gcgtttcccc ctgatggctc cctcttgcgc tctcctgttc ccgtcctgcg     1740
gcgtccgtgt tgtggtggag gctttaccca aatcaccacg tcccgttccg tgtagacagt     1800
tcgctccaag ctgggctgtg tgcaagaacc ccccgttcag cccgactgct gcgccttatc     1860
cggtaactat catcttgagt ccaacccgga aagacacgac aaaacgccac tggcagcagc     1920
cattggtaac tgagaattag tggatttaga tatcgagagt cttgaagtgg tggcctaaca     1980
gaggctacac tgaaaggaca gtatttggta tctgcgctcc actaaagcca gttaccaggt     2040
taagcagttc cccaactgac ttaaccttcg atcaaaccgc ctccccaggc ggttttttcg     2100
tttacagagc aggagattac gacgatcgta aaaggatctc aagaagatcc tttacggatt     2160
cccgacacca tcactctaga tttcagtgca atttatctct tcaaatgtag cacctgaagt     2220
cagccccata cgatataagt tgtaattctc atgttagtca tgccccgcgc ccaccggaag     2280
gagctgactg ggttgaaggc tctcaagggc atcggtcgag atcccggtgc ctaatgagtg     2340
agctaactta cattaattgc gttgcgctca ctgcccgctt tccagtcggg aaacctgtcg     2400
tgccagctgc attaatgaat cggccaacgc gcggggagag gcggtttgcg tattgggcgc     2460
cagggtggtt tttcttttca ccagtgagac gggcaacagc tgattgccct tcaccgcctg     2520
```

```
gccctgagag agttgcagca agcggtccac gctggtttgc cccagcaggc gaaaatcctg    2580
tttgatggtg gttaacggcg ggatataaca tgagctgtct tcggtatcgt cgtatcccac    2640
taccgagatg tccgcaccaa cgcgcagccc ggactcggta atggcgcgca ttgcgcccag    2700
cgccatctga tcgttggcaa ccagcatcgc agtgggaacg atgccctcat tcagcatttg    2760
catggtttgt tgaaaaccgg acatggcact ccagtcgcct tcccgttccg ctatcggctg    2820
aatttgattg cgagtgagat atttatgcca gccagccaga cgcagacgcg ccgagacaga    2880
acttaatggg cccgctaaca gcgcgatttg ctggtgaccc aatgcgacca gatgctccac    2940
gcccagtcgc gtaccgtctt catgggagaa aataatactg ttgatgggtg tctggtcaga    3000
gacatcaaga aataacgccg gaacattagt gcaggcagct tccacagcaa tggcatcctg    3060
gtcatccagc ggatagttaa tgatcagccc actgacgcgt tgcgcgagaa gattgtgcac    3120
cgccgcttta caggcttcga cgccgcttcg ttctaccatc gacaccacca cgctggcacc    3180
cagttgatcg gcgcgagatt taatcgccgc gacaatttgc gacggcgcgt gcagggccag    3240
actggaggtg gcaacgccaa tcagcaacga ctgtttgccc gccagttgtt gtgccacgcg    3300
gttgggaatg taattcagct ccgccatcgc cgcttccact tttcccgcg ttttcgcaga    3360 aacgtggctg gcctggttca ccacgcggga acggtctga taagagacac cggcatactc    3420
tgcgacatcg tataacgtta ctggtttcac attcaccacc ctgaattgac tctcttccgg    3480
gcgctatcat gccataccgc gaaaggtttt gcgccattcg atggtgtccg ggatctcgac    3540
gctctccctt atg                                                       3553
```

<210> SEQ ID NO 82
<211> LENGTH: 3554
<212> TYPE: DNA
<213> ORGANISM: Artificial Sequence
<220> FEATURE:
<223> OTHER INFORMATION: synthetic

<400> SEQUENCE: 82

```
ctagtaaatt cgcgtttcta cggtagccgg gcgctaatac gactcactat agggagccag     60
attgcgatcg ccctcccacg tgctcagatc ggactttaga acagaggaga taaagatgga    120
tctgagcaca acctggcggc agcgcaagaa gatgaccatg attacggatt cactggccgt    180
cgttttacaa cgtcgtgact gggaaaaccc tggcgttacc caacttaatc gccttgcagc    240
acatccccct ttcgccagct ggcgtaatag cgaagaggcc cgcaccgatc gcccttccca    300
acagttgcgc agcctgaatg gcgaatggta ataatagcat aaccccttgg ggcctctaaa    360
cgggtcttga ggggtttttt gctgaaacct caggcatttg agaagcacac ggtcacactg    420
cttccggtag tcaataaacc ggtaaaccag caatagacat aagcggctat ttaacgaccc    480
tgccctgaac cgacgacaag ctgacgaccg ggtctccgca agtggcactt tcggggaaa    540 tgtgcgcgga acccctattt gtttattttt ctaaatacat tcaaatatgt atccgctcat    600
gaattaattc ttagaaaaac tcatcgagca tcaaatgaaa ctgcaattta ttcatatcag    660
gattatcaat accatatttt tgaaaaagcc gtttctgtaa tgaaggagaa aactcaccga    720
ggcagttcca taggatggca agatcctggt atcggtctgc gattccgact cgtccaacat    780
caatacaacc tattaatttc ccctcgtcaa aaataaggtt atcaagtgag aaatcaccat    840
gagtgacgac tgaatccggt gagaatggca aaagtttatg catttctttc cagacttgtt    900
caacaggcca gccattacgc tcgtcatcaa aatcactcgc atcaaccaaa ccgttattca    960
ttcgtgattg cgcctgagcg agacgaaata cgcggtcgct gttaaaagga caattacaaa   1020
```

```
caggaatcga atgcaaccgg cgcaggaaca ctgccagcgc atcaacaata ttttcacctg   1080
aatcaggata ttcttctaat acctggaatg ctgttttccc ggggatcgca gtggtgagta   1140
accatgcatc atcaggagta cggataaaat gcttgatggt cggaagaggc ataaattccg   1200
tcagccagtt tagtctgacc atctcatctg taacatcatt ggcaacgcta cctttgccat   1260
gtttcagaaa caactctggc gcatcgggct tcccatacaa tcgatagatt gtcgcacctg   1320
attgcccgac attatcgcga gcccatttat acccatataa atcagcatcc atgttggaat   1380
ttaatcgcgg cctagagcaa gacgtttccc gttgaatatg gctcatactc ttcctttttc   1440
aatattattg aagcatttat cagggttatt gtctcatgag cggatacata tttgaatgta   1500
tttagaaaaa taaacaaata ggcatgctag cgcagaaacg tcctagaaga tgccaggagg   1560
atacttagca gagagacaat aaggccggag cgaagccgtt tttccatagg ctccgccccc   1620
ctgacgaaca tcacgaaatc tgacgctcaa atcagtggtg gcgaaacccg acaggactat   1680
aaagatacca ggcgtttccc cctgatggct ccctcttgcg ctctcctgtt cccgtcctgc   1740
ggcgtccgtg ttgtggtgga ggctttaccc aaatcaccac gtcccgttcc gtgtagacag   1800
ttcgctccaa gctgggctgt gtgcaagaac cccccgttca gcccgactgc tgcgccttat   1860
ccggtaacta tcatcttgag tccaacccgg aaagacacga caaaacgcca ctggcagcag   1920
ccattggtaa ctgagaatta gtggatttag atatcgagag tcttgaagtg gtggcctaac   1980
agaggctaca ctgaaaggac agtatttggt atctgcgctc cactaaagcc agttaccagg   2040
ttaagcagtt ccccaactga cttaaccttc gatcaaaccg cctccccagg cggttttttc   2100
gtttacagag caggagatta cgacgatcgt aaaaggatct caagaagatc ctttacggat   2160
tcccgacacc atcactctag atttcagtgc aatttatctc ttcaaatgta gcacctgaag   2220
tcagccccat acgatataag ttgtaattct catgttagtc atgccccgcg cccaccggaa   2280
ggagctgact gggttgaagg ctctcaaggg catcggtcga gatcccggtg cctaatgagt   2340
gagctaactt acattaattg cgttgcgctc actgcccgct ttccagtcgg gaaacctgtc   2400
gtgccagctg cattaatgaa tcggccaacg cgcgggagag gcggtttgc gtattgggcg   2460 ccagggtggt ttttcttttc accagtgaga cgggcaacag ctgattgccc ttcaccgcct   2520
ggccctgaga gagttgcagc aagcggtcca cgctggtttg ccccagcagg cgaaaatcct   2580
gtttgatggt ggttaacggc gggatataac atgagctgtc ttcggtatcg tcgtatccca   2640
ctaccgagat gtccgcacca acgcgcagcc cggactcggt aatggcgcgc attgcgccca   2700
gcgccatctg atcgttggca accagcatcg cagtgggaac gatgccctca ttcagcattt   2760
gcatggtttg ttgaaaaccg gacatggcac tccagtcgcc ttcccgttcc gctatcggct   2820
gaatttgatt gcgagtgaga tatttatgcc agccagccag acgcagacgc gccgagacag   2880
aacttaatgg gcccgctaac agcgcgattt gctggtgacc caatgcgacc agatgctcca   2940
cgcccagtcg cgtaccgtct tcatgggaga aataatact gttgatgggt gtctggtcag   3000
agacatcaag aaataacgcc ggaacattag tgcaggcagc ttccacagca atggcatcct   3060
ggtcatccag cggatagtta atgatcagcc cactgacgcg ttgcgcgaga agattgtgca   3120
ccgccgcttt acaggcttcg acgccgcttc gttctaccat cgacaccacc acgctggcac   3180
ccagttgatc ggcgcgagat ttaatcgccg cgacaatttg cgacggcgcg tgcagggcca   3240
gactggaggt ggcaacgcca atcagcaacg actgtttgcc cgccagttgt tgtgccacgc   3300
ggttgggaat gtaattcagc tccgccatcg ccgcttccac ttttcccgc gttttcgcag   3360
```

-continued

```
aaacgtggct ggcctggttc accacgcggg aaacggtctg ataagagaca ccggcatact    3420
ctgcgacatc gtataacgtt actggtttca cattcaccac cctgaattga ctctcttccg    3480
ggcgctatca tgccataccg cgaaaggttt tgcgccattc gatggtgtcc gggatctcga    3540
cgctctccct tatg                                                     3554
```